(12) United States Patent
Batchelor et al.

(10) Patent No.: US 9,452,011 B2
(45) Date of Patent: Sep. 27, 2016

(54) COMBINATION ELECTROSURGICAL DEVICE

(71) Applicant: GYRUS ACMI, INC., Southborough, MA (US)

(72) Inventors: Kester J. Batchelor, Mound, MN (US); Nikhil M. Murdeshwar, Maple Grove, MN (US); Jyue Boon (Jonas) Lim, New Brighton, MN (US); Dennis G. Lamser, Marlborough, MA (US); Tsuyoshi Hayashida, Maple Grove, MN (US); Richard J. Curtis, Maple Grove, MN (US); Ryan Windgassen, Nowthen, MN (US); Theodore Blus, Shoreview, MN (US); Riyad Moe, Madison, WI (US)

(73) Assignee: GYRUS ACMI, INC. MA (US)

( * ) Notice: Subject to any disclaimer, the term of this patent is extended or adjusted under 35 U.S.C. 154(b) by 210 days.

(21) Appl. No.: 14/205,598

(22) Filed: Mar. 12, 2014

(65) Prior Publication Data
US 2014/0276795 A1 Sep. 18, 2014

Related U.S. Application Data

(60) Provisional application No. 61/845,664, filed on Jul. 12, 2013, provisional application No. 61/787,731, filed on Mar. 15, 2013.

(51) Int. Cl.
*A61B 18/14* (2006.01)
*A61B 18/16* (2006.01)
(Continued)

(52) U.S. Cl.
CPC ....... *A61B 18/1445* (2013.01); *A61B 18/1233* (2013.01); *A61B 18/1442* (2013.01);
(Continued)

(58) Field of Classification Search
CPC .......... A61B 2018/00916; A61B 2018/00922; A61B 2018/00958; A61B 2018/00952; A61B 2018/00946; A61B 18/1447
See application file for complete search history.

(56) References Cited

U.S. PATENT DOCUMENTS

| 1,198,958 A | 9/1916 | Risely |
| 2,042,985 A | 6/1936 | Gardella |

(Continued)

FOREIGN PATENT DOCUMENTS

| EP | 0392548 A1 | 10/1994 |
| EP | 1089664 | 4/2001 |

(Continued)

OTHER PUBLICATIONS

Potentially related U.S. Appl. No. 14/829,725, filed Aug. 19, 2015.
(Continued)

*Primary Examiner* — Ronald Hupczey, Jr.
*Assistant Examiner* — Bo Ouyang
(74) *Attorney, Agent, or Firm* — The Dobrusin Law Firm, P.C.; Daniel P. Aleksynas

(57) ABSTRACT

An electrosurgical device comprising: (a) forceps including: (i) a first working arm and (ii) a second working arm; (b) a blade electrode; wherein the electrosurgical device is capable of being switched between a first electrical configuration so that the electrosurgical device delivers a first therapy current through the first working arm, the second working arm, or both, and a second electrical configuration so that the electrosurgical device delivers a second therapy current through the blade electrode; and wherein the first working arm and the second working arm of the forceps are immobilized in the second electrical configuration so that both the forceps and the first therapy current are disabled.

15 Claims, 27 Drawing Sheets

(51) Int. Cl.
*A61B 18/04* (2006.01)
*A61B 18/12* (2006.01)
*A61B 18/00* (2006.01)

(52) U.S. Cl.
CPC ............. *A61B2018/00589* (2013.01); *A61B 2018/00595* (2013.01); *A61B 2018/00601* (2013.01); *A61B 2018/00607* (2013.01); *A61B 2018/1412* (2013.01); *A61B 2018/1462* (2013.01)

(56) References Cited

U.S. PATENT DOCUMENTS

| | | |
|---|---|---|
| 2,214,984 A | 9/1940 | Bachmann |
| 2,381,084 A | 8/1945 | Slad |
| 2,575,652 A | 11/1951 | Bovee |
| 2,894,424 A | 7/1959 | Vaughan |
| 3,399,583 A | 9/1968 | Hall |
| 3,417,752 A | 12/1968 | Butler |
| 3,465,621 A | 9/1969 | Ladd |
| 3,576,072 A | 4/1971 | Foster |
| 3,643,663 A | 2/1972 | Sutter |
| 3,685,518 A | 8/1972 | Beuerle et al. |
| 3,699,632 A | 10/1972 | Anhalt |
| 3,818,784 A | 6/1974 | McClure |
| 3,913,586 A | 10/1975 | Baumgarten |
| 4,041,952 A | 8/1977 | Morrison, Jr. et al. |
| 4,154,226 A | 5/1979 | Hennig et al. |
| 4,171,700 A | 10/1979 | Farin |
| 4,202,337 A | 5/1980 | Hren et al. |
| 4,318,313 A | 3/1982 | Tartaglia |
| 4,375,218 A | 3/1983 | DiGeronimo |
| 4,407,069 A | 10/1983 | Conners |
| 4,418,692 A | 12/1983 | Guay |
| 4,463,759 A | 8/1984 | Garito et al. |
| 4,492,231 A | 1/1985 | Auth |
| 4,492,832 A | 1/1985 | Taylor |
| 4,494,543 A | 1/1985 | Hart |
| 4,504,707 A | 3/1985 | Ochiai |
| 4,524,648 A | 6/1985 | Chung |
| 4,552,143 A | 11/1985 | Lottick |
| 4,669,470 A | 6/1987 | Brandfield |
| 4,686,980 A | 8/1987 | Williams et al. |
| 4,713,885 A | 12/1987 | Keklak et al. |
| 4,757,612 A | 7/1988 | Peyrot |
| 4,784,136 A | 11/1988 | Klein |
| 4,860,745 A | 8/1989 | Farin et al. |
| 4,896,661 A | 1/1990 | Bogert et al. |
| 4,935,027 A | 6/1990 | Yoon |
| 5,021,616 A | 6/1991 | Hardt |
| 5,035,695 A | 7/1991 | Weber, Jr. et al. |
| 5,071,426 A | 12/1991 | Dolgin et al. |
| 5,104,397 A | 4/1992 | Vasconcelos et al. |
| 5,108,392 A | 4/1992 | Spingler |
| 5,147,378 A | 9/1992 | Markham |
| 5,176,702 A | 1/1993 | Bales et al. |
| 5,190,541 A | 3/1993 | Abele et al. |
| 5,196,009 A | 3/1993 | Kirwan, Jr. |
| 5,207,691 A | 5/1993 | Nardella |
| 5,207,696 A | 5/1993 | Matwijcow |
| 5,208,983 A | 5/1993 | Masse |
| 5,226,904 A | 7/1993 | Gentelia et al. |
| 5,281,216 A | 1/1994 | Klicek |
| 5,290,286 A | 3/1994 | Parins |
| 5,293,878 A | 3/1994 | Bales et al. |
| 5,318,589 A | 6/1994 | Lichtman |
| 5,342,359 A | 8/1994 | Rydell |
| 5,370,659 A | 12/1994 | Sakashita |
| 5,403,312 A | 4/1995 | Yates et al. |
| 5,413,575 A | 5/1995 | Haenggi |
| 5,423,814 A | 6/1995 | Zhu et al. |
| 5,425,743 A | 6/1995 | Nicholas |
| 5,440,813 A | 8/1995 | Roskam |
| 5,441,498 A | 8/1995 | Perkins |
| 5,443,463 A | 8/1995 | Stern et al. |
| 5,456,695 A | 10/1995 | Herve Dallemagne |
| 5,458,598 A | 10/1995 | Feinberg et al. |
| 5,472,442 A | 12/1995 | Klicek |
| 5,483,952 A | 1/1996 | Aranyi |
| 5,484,435 A | 1/1996 | Fleenor et al. |
| 5,499,998 A | 3/1996 | Meade |
| 5,531,744 A | 7/1996 | Nardella et al. |
| 5,540,685 A | 7/1996 | Parins et al. |
| 5,562,503 A | 10/1996 | Ellman et al. |
| 5,573,424 A | 11/1996 | Poppe |
| 5,626,577 A | 5/1997 | Harris |
| 5,658,281 A | 8/1997 | Heard |
| 5,702,390 A | 12/1997 | Austin et al. |
| 5,709,680 A | 1/1998 | Yates et al. |
| 5,735,849 A | 4/1998 | Baden et al. |
| 5,779,701 A | 7/1998 | McBrayer et al. |
| 5,810,805 A | 9/1998 | Sutcu et al. |
| 5,827,281 A | 10/1998 | Levin |
| 5,884,954 A | 3/1999 | Trozera |
| 5,891,140 A | 4/1999 | Ginn et al. |
| 5,902,301 A | 5/1999 | Olig |
| 5,922,001 A | 7/1999 | Yoon |
| 5,951,545 A | 9/1999 | Schilling et al. |
| 6,024,741 A | 2/2000 | Williamson, IV et al. |
| 6,030,384 A | 2/2000 | Nezhat |
| 6,039,734 A | 3/2000 | Goble |
| 6,050,996 A | 4/2000 | Schmaltz et al. |
| 6,053,908 A | 4/2000 | Crainich et al. |
| 6,074,386 A | 6/2000 | Goble et al. |
| 6,102,909 A | 8/2000 | Chen et al. |
| 6,110,171 A | 8/2000 | Rydell |
| 6,113,596 A | 9/2000 | Hooven et al. |
| 6,117,158 A | 9/2000 | Measamer et al. |
| 6,117,169 A | 9/2000 | Moe |
| 6,152,923 A | 11/2000 | Ryan |
| 6,190,386 B1 | 2/2001 | Rydell |
| 6,270,497 B1 | 8/2001 | Sekino et al. |
| 6,273,887 B1 | 8/2001 | Yamauchi et al. |
| 6,325,795 B1 | 12/2001 | Lindemann et al. |
| 6,355,032 B1 | 3/2002 | Hovda et al. |
| 6,358,268 B1 | 3/2002 | Hunt et al. |
| 6,402,747 B1 | 6/2002 | Lindemann et al. |
| 6,428,538 B1 | 8/2002 | Blewett et al. |
| 6,458,128 B1 | 10/2002 | Schulze |
| 6,464,704 B2 | 10/2002 | Schmaltz et al. |
| 6,486,419 B2 | 11/2002 | Horiguchi et al. |
| 6,494,886 B1 | 12/2002 | Wilk et al. |
| 6,514,252 B2 | 2/2003 | Nezhat et al. |
| 6,551,313 B1 | 4/2003 | Levin |
| 6,585,735 B1 | 7/2003 | Frazier et al. |
| 6,619,038 B2 | 9/2003 | Takada et al. |
| 6,623,499 B1 | 9/2003 | Andreini et al. |
| 6,641,595 B1 | 11/2003 | Moran et al. |
| 6,652,514 B2 | 11/2003 | Ellman et al. |
| 6,679,882 B1 | 1/2004 | Kornerup |
| 6,689,130 B2 | 2/2004 | Arai et al. |
| 6,695,840 B2 | 2/2004 | Schulze |
| 6,726,686 B2 | 4/2004 | Buysse et al. |
| 6,749,610 B2 | 6/2004 | Kirwan, Jr. et al. |
| 6,752,767 B2 | 6/2004 | Turovskiy et al. |
| 6,773,434 B2 | 8/2004 | Ciarrocca |
| 6,808,525 B2 | 10/2004 | Latterell et al. |
| 6,827,717 B2 | 12/2004 | Brommersma et al. |
| 6,860,882 B2 | 3/2005 | Battles et al. |
| 6,926,716 B2 | 8/2005 | Baker et al. |
| 6,942,662 B2 | 9/2005 | Goble et al. |
| 7,083,613 B2 | 8/2006 | Treat |
| 7,094,231 B1 | 8/2006 | Ellman et al. |
| 7,108,694 B2 | 9/2006 | Miura et al. |
| 7,112,199 B2 | 9/2006 | Cosmescu |
| 7,147,637 B2 | 12/2006 | Goble |
| 7,150,749 B2 | 12/2006 | Dycus et al. |
| 7,156,846 B2 | 1/2007 | Dycus et al. |
| 7,232,440 B2 | 6/2007 | Dumbauld et al. |
| 7,244,257 B2 | 7/2007 | Podhajsky et al. |
| 7,252,667 B2 | 8/2007 | Moses et al. |
| 7,344,536 B1 | 3/2008 | Lunsford et al. |
| 7,367,976 B2 | 5/2008 | Lawes et al. |
| 7,377,902 B2 | 5/2008 | Burbank |

(56) References Cited

U.S. PATENT DOCUMENTS

| | | | |
|---|---|---|---|
| 7,481,810 B2 | 1/2009 | Dumbauld et al. |
| 7,503,917 B2 | 3/2009 | Sartor et al. |
| 7,604,635 B2 | 10/2009 | McClurken et al. |
| 7,625,391 B2 | 12/2009 | Kebel et al. |
| 7,674,261 B2 | 3/2010 | Garito et al. |
| 7,686,827 B2 | 3/2010 | Hushka |
| 7,722,607 B2 | 5/2010 | Dumbauld et al. |
| 7,753,909 B2 | 7/2010 | Chapman et al. |
| 7,758,577 B2 | 7/2010 | Nobis et al. |
| 7,789,878 B2 | 9/2010 | Dumbauld et al. |
| 7,879,035 B2 | 2/2011 | Garrison et al. |
| 7,896,875 B2 | 3/2011 | Heim et al. |
| 7,909,820 B2 | 3/2011 | Lipson et al. |
| 7,922,718 B2 | 4/2011 | Moses et al. |
| 7,931,649 B2 | 4/2011 | Couture et al. |
| 7,931,668 B2 | 4/2011 | Sloat |
| 7,938,469 B2 | 5/2011 | Ait-Mani |
| 7,942,872 B2 | 5/2011 | Ein-Gal |
| 7,955,331 B2 | 6/2011 | Truckai et al. |
| 8,062,292 B1 | 11/2011 | Slater |
| 8,100,894 B2 | 1/2012 | Mucko et al. |
| 8,162,940 B2 | 4/2012 | Johnson et al. |
| 8,216,231 B2 | 7/2012 | Behl et al. |
| 8,226,649 B2 | 7/2012 | Falkenstein et al. |
| 8,246,094 B2 | 8/2012 | Long et al. |
| 8,251,989 B1 | 8/2012 | Newton et al. |
| 8,262,655 B2 | 9/2012 | Ghabrial et al. |
| 8,328,170 B2 | 12/2012 | Wasinger |
| 8,485,413 B2 | 7/2013 | Scheib et al. |
| 8,491,626 B2 | 7/2013 | Roy et al. |
| 8,496,603 B2 | 7/2013 | Mamourian |
| 8,568,411 B2 | 10/2013 | Falkenstein et al. |
| 8,628,529 B2 | 1/2014 | Aldridge et al. |
| 8,702,691 B2 | 4/2014 | Weber et al. |
| 8,882,756 B2 | 11/2014 | Greeley et al. |
| 8,939,972 B2 | 1/2015 | Twomey |
| 9,023,035 B2 | 5/2015 | Allen et al. |
| 9,204,879 B2 | 12/2015 | Shelton |
| 2002/0106609 A1 | 8/2002 | Palermo et al. |
| 2002/0107517 A1 | 8/2002 | Witt et al. |
| 2002/0115997 A1 | 8/2002 | Truckai et al. |
| 2003/0018329 A1 | 1/2003 | Hooven |
| 2003/0050633 A1 | 3/2003 | Ellman |
| 2003/0097126 A1 | 5/2003 | Woloszko |
| 2003/0109876 A1 | 6/2003 | Yamauchi |
| 2003/0114850 A1 | 6/2003 | McClurken et al. |
| 2003/0144652 A1 | 7/2003 | Baker et al. |
| 2003/0181904 A1 | 9/2003 | Levine et al. |
| 2004/0030330 A1 | 2/2004 | Brassell et al. |
| 2004/0082946 A1 | 4/2004 | Malis |
| 2004/0097117 A1 | 5/2004 | Gonnering |
| 2005/0113824 A1 | 5/2005 | Sartor |
| 2005/0113825 A1 | 5/2005 | Cosmescu |
| 2005/0113827 A1* | 5/2005 | Dumbauld ......... A61B 18/1445 606/45 |
| 2005/0187512 A1 | 8/2005 | Isola et al. |
| 2005/0216019 A1* | 9/2005 | Eckman ............. A61B 17/1671 606/79 |
| 2006/0084973 A1* | 4/2006 | Hushka .............. A61B 18/1445 606/42 |
| 2006/0190035 A1 | 8/2006 | Hushka et al. |
| 2006/0217701 A1 | 9/2006 | Young et al. |
| 2007/0093857 A1 | 4/2007 | Rogers et al. |
| 2007/0123855 A1 | 5/2007 | Morley et al. |
| 2007/0129716 A1 | 6/2007 | Daw |
| 2007/0179491 A1 | 8/2007 | Kratoska et al. |
| 2008/0033428 A1 | 2/2008 | Artale et al. |
| 2008/0147092 A1 | 6/2008 | Rogge et al. |
| 2008/0154300 A1 | 6/2008 | Jabbour |
| 2008/0236860 A1 | 10/2008 | Howe |
| 2008/0287948 A1 | 11/2008 | Newton et al. |
| 2009/0062786 A1 | 3/2009 | Garito et al. |
| 2009/0062792 A1 | 3/2009 | Vakharia et al. |
| 2009/0062830 A1* | 3/2009 | Hiraoka ............. A61B 10/0233 606/185 |
| 2009/0093804 A1 | 4/2009 | Newton |
| 2009/0138003 A1 | 5/2009 | DeVille et al. |
| 2009/0138013 A1 | 5/2009 | Thorne et al. |
| 2009/0192509 A1 | 7/2009 | Curtis |
| 2010/0042096 A1 | 2/2010 | Ellman |
| 2010/0069940 A1* | 3/2010 | Miller ............... A61B 17/32006 606/169 |
| 2010/0087814 A1 | 4/2010 | Desinger et al. |
| 2010/0137854 A1 | 6/2010 | Hosier |
| 2010/0228249 A1 | 9/2010 | Mohr |
| 2011/0045680 A1 | 2/2011 | Beller |
| 2011/0054462 A1 | 3/2011 | Ellman |
| 2011/0077648 A1 | 3/2011 | Lee et al. |
| 2011/0112530 A1 | 5/2011 | Keller |
| 2011/0178515 A1 | 7/2011 | Bloom et al. |
| 2011/0224669 A1 | 9/2011 | Podany |
| 2011/0251613 A1 | 10/2011 | Guerra et al. |
| 2011/0319892 A1 | 12/2011 | Blomeyer |
| 2012/0022530 A1 | 1/2012 | Woodruff et al. |
| 2012/0078292 A1 | 3/2012 | Banju |
| 2012/0095460 A1* | 4/2012 | Rooks .................... A61B 17/28 606/45 |
| 2012/0101501 A1 | 4/2012 | Nishimura et al. |
| 2012/0123405 A1 | 5/2012 | Moua et al. |
| 2012/0150165 A1 | 6/2012 | Conley |
| 2012/0202388 A1 | 8/2012 | Selig |
| 2013/0023874 A1 | 1/2013 | Lawes et al. |
| 2013/0066317 A1 | 3/2013 | Evans et al. |
| 2013/0079762 A1 | 3/2013 | Twomey et al. |
| 2013/0138096 A1* | 5/2013 | Benn .................. A61B 18/1477 606/33 |
| 2013/0178852 A1 | 7/2013 | Allen, IV et al. |
| 2013/0237982 A1* | 9/2013 | Rencher ............. A61B 18/1402 606/39 |
| 2014/0236202 A1 | 8/2014 | Palmer et al. |
| 2014/0276772 A1 | 9/2014 | Batchelor et al. |
| 2014/0276785 A1 | 9/2014 | Batchelor et al. |
| 2014/0276786 A1 | 9/2014 | Batchelor |
| 2014/0276794 A1 | 9/2014 | Batchelor et al. |
| 2014/0276796 A1 | 9/2014 | Batchelor et al. |
| 2014/0276797 A1 | 9/2014 | Batchelor et al. |
| 2014/0276798 A1 | 9/2014 | Batchelor et al. |
| 2014/0276799 A1 | 9/2014 | Batchelor et al. |
| 2014/0276800 A1 | 9/2014 | Batchelor et al. |
| 2014/0276804 A1 | 9/2014 | Batchelor |
| 2015/0119885 A1 | 4/2015 | Windgassen et al. |
| 2015/0148798 A1 | 5/2015 | Windgassen et al. |

FOREIGN PATENT DOCUMENTS

| | | |
|---|---|---|
| EP | 1530952 A1 | 5/2005 |
| EP | 1810629 A2 | 7/2007 |
| EP | 1977706 A1 | 10/2008 |
| EP | 2403422 | 1/2012 |
| WO | 9966850 | 12/1999 |
| WO | 2006/122279 | 11/2006 |
| WO | 2007/002545 | 1/2007 |
| WO | 2007/093857 | 8/2007 |
| WO | 2010/101897 | 9/2010 |
| WO | 2014/096815 A2 | 6/2014 |

OTHER PUBLICATIONS

Potentially related U.S. Appl. No. 14/830,069, filed Aug. 19, 2015.
Potentially related U.S. Appl. No. 14/830,255, filed Aug. 19, 2015.
International Preliminary Report on Patentability Application No. PCT/US2014/023958, mailed Mar. 5, 2015.
International Search Report and Written Opinion for Application No. PCT/US2014/023958 dated Jul. 21, 2014.
International Search Report and Written Opinion for Application No. PCT/US2014/024134 dated Apr. 30, 2014.
International Search Report and Written Opinion for Application No. PCT/US2014/024197 dated Jul. 21, 2014.
Potentially related U.S. Appl. No. 14/177,780, filed Feb. 11, 2014.
Potentially related U.S. Appl. No. 14/178,411, filed Feb. 12, 2014.
Potentially related U.S. Appl. No. 14/209,071, filed Mar. 13, 2014.
Potentially related U.S. Appl. No. 14/205,919, filed Mar. 12, 2014.
Potentially related to U.S. Appl. No. 14/206,010, filed Mar. 12, 2014.

(56) References Cited

OTHER PUBLICATIONS

Potentially related U.S. Appl. No. 14/210,535, filed Mar. 14, 2014.
Potentially related U.S. Appl. No. 14/210,741, filed Mar. 14, 2014.
Potentially related U.S. Appl. No. 14/211,042, filed Mar. 14, 2014.
Potentially related U.S. Appl. No. 14/178,569, filed Feb. 12, 2014.
Potentially related U.S. Appl. No. 14/178,577, filed Feb. 12, 2014.
315MHZ sliding remote cover, available at website : http://www.aliexpress.com/item/Sliding-Cover-Gate-Remote-Control-Duplicator-Adjustable-Frequency-Remote-Copy-100pCS-lot-Free-Shipping-by-DHL/566451354.html?tracelog=back_to_detail_a (accessed on Feb. 21, 2013).
Sliding Gate Remote Control Duplicator, available at website: http://www.aliexpress.com/item/315MHZ-sliding-cover-remote-controller-duplicating-remote-controller-sliding-gate-remote-garager-door-remote/491795542.html (accessed on Feb. 21, 2013).
Office Action from European Patent Office for Application No. 14722009.9 dated May 10, 2016.

* cited by examiner

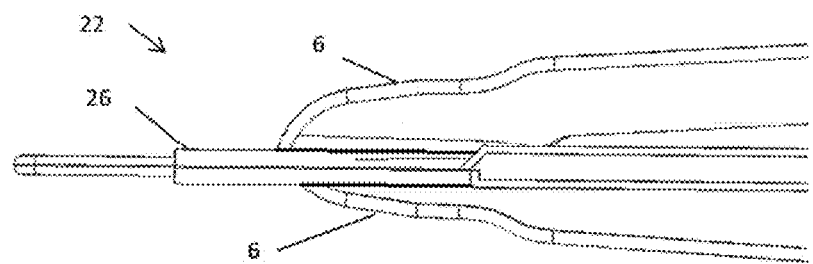
Figure 2B
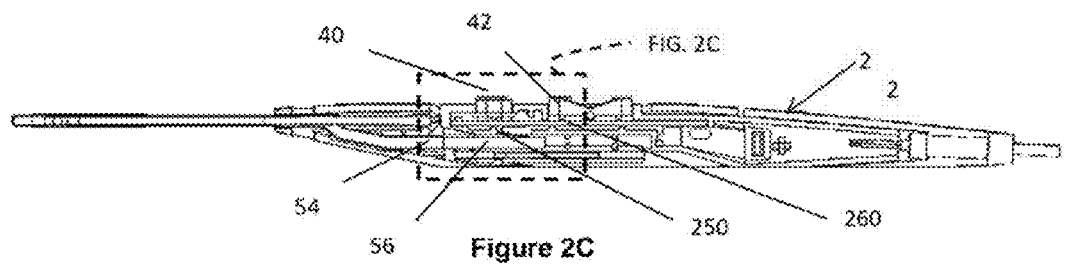
Figure 2C
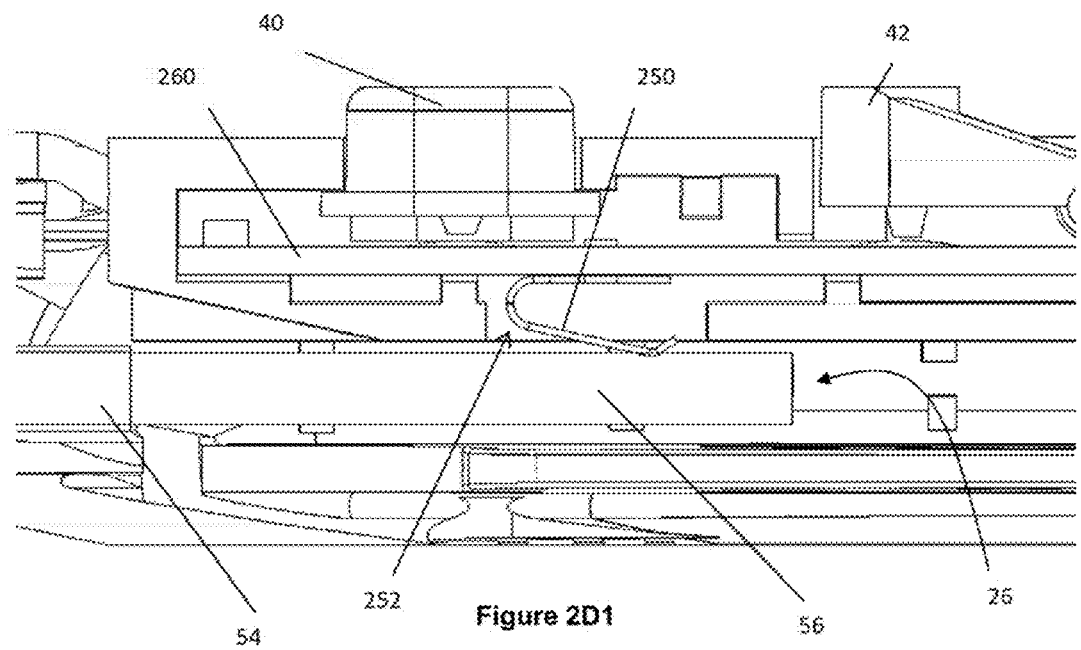
Figure 2D1

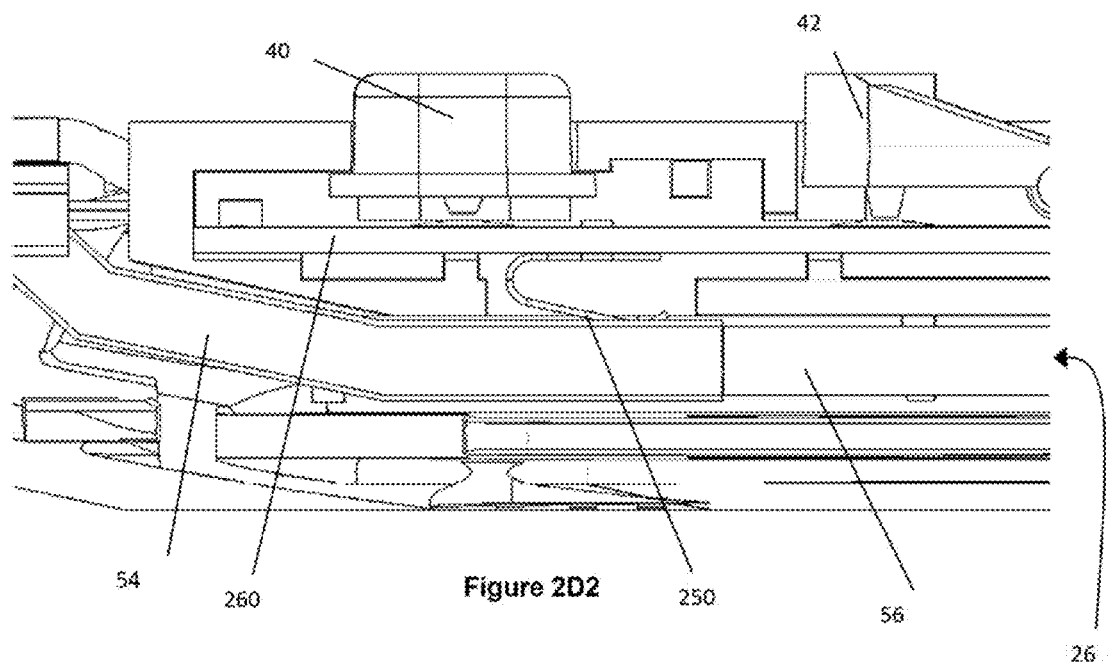
Figure 2D2
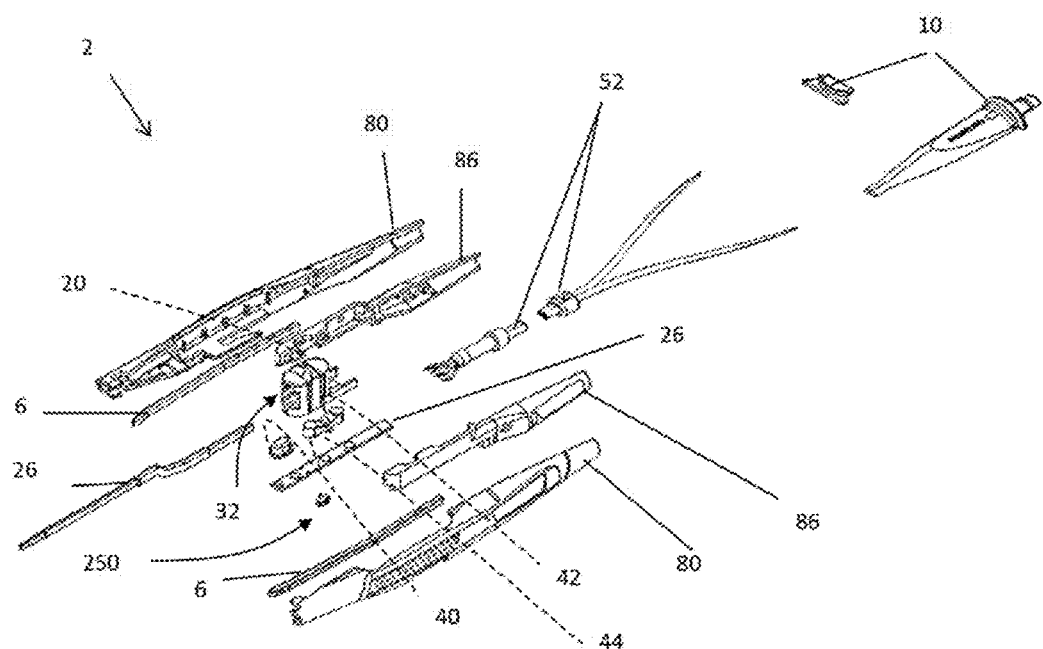
Figure 3A

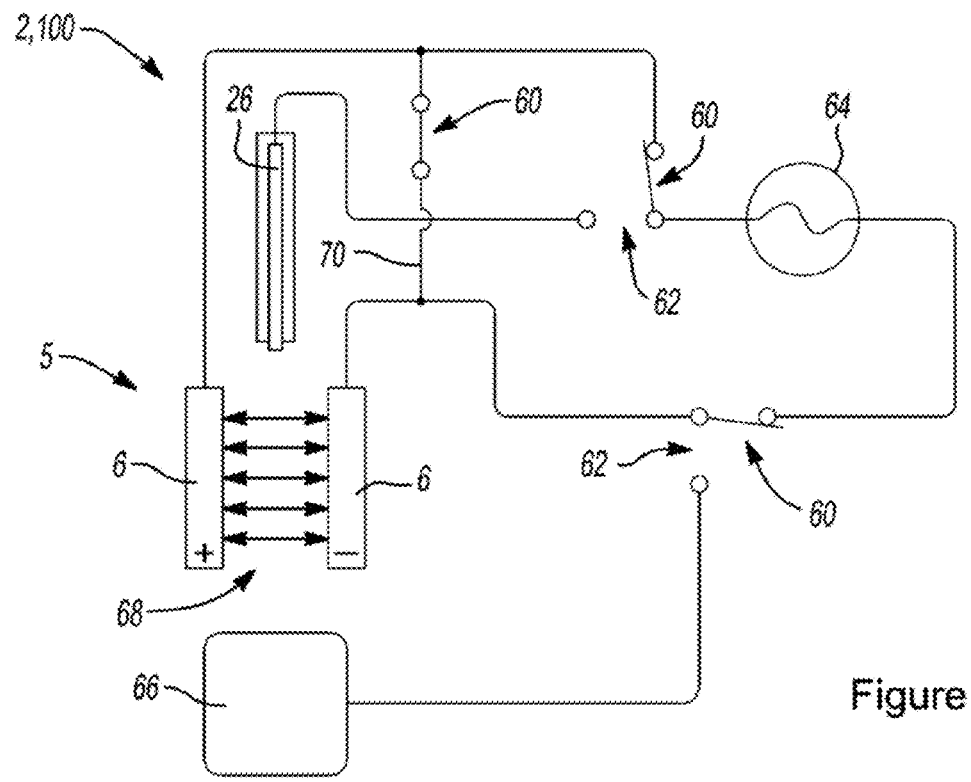
Figure 20A1
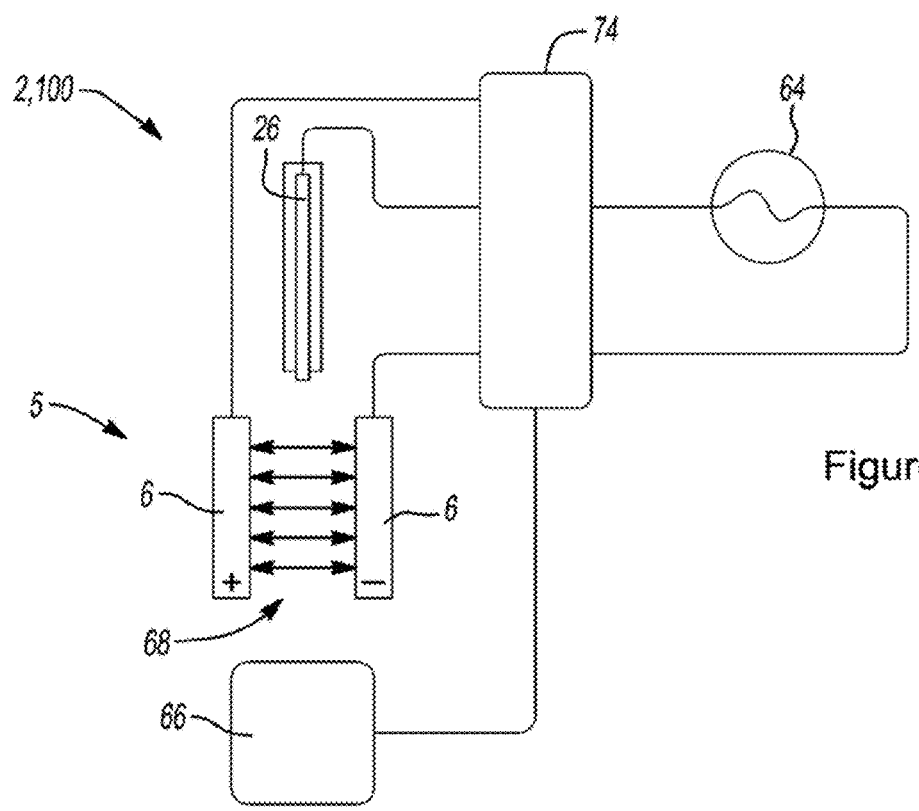
Figure 20A2

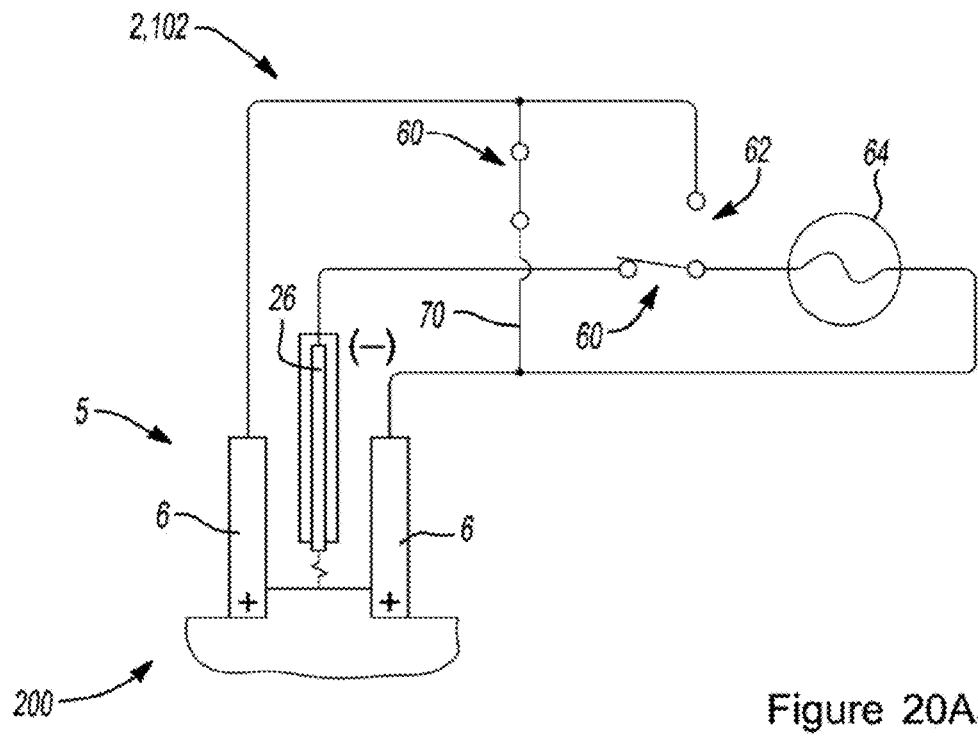
Figure 20A3
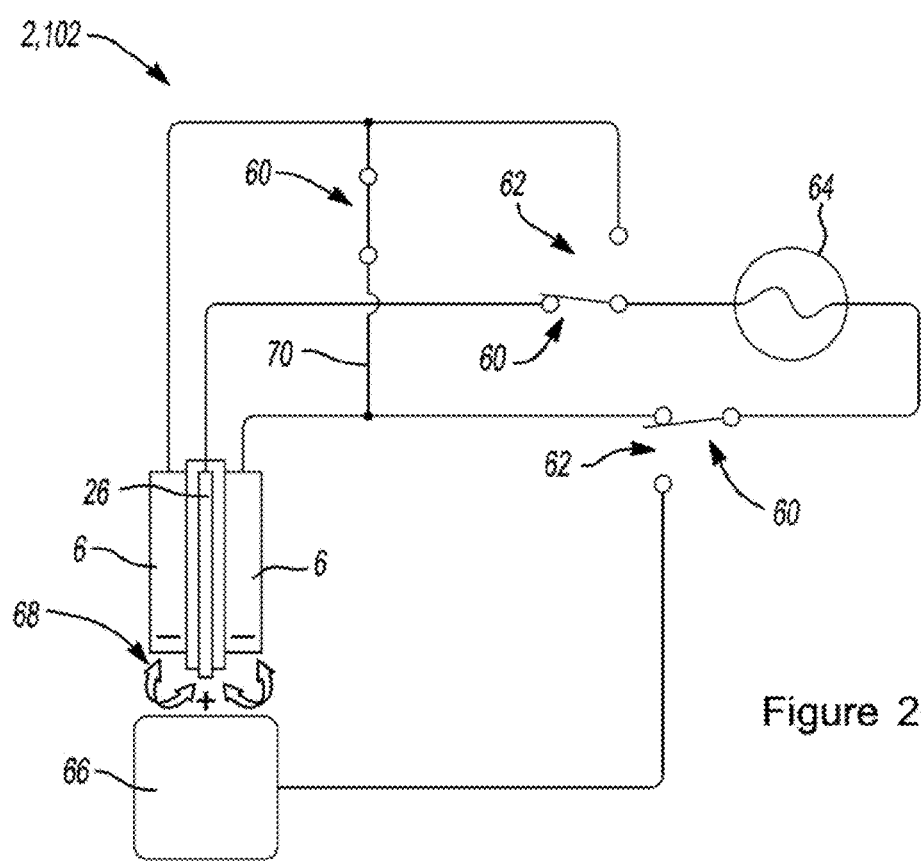
Figure 20B

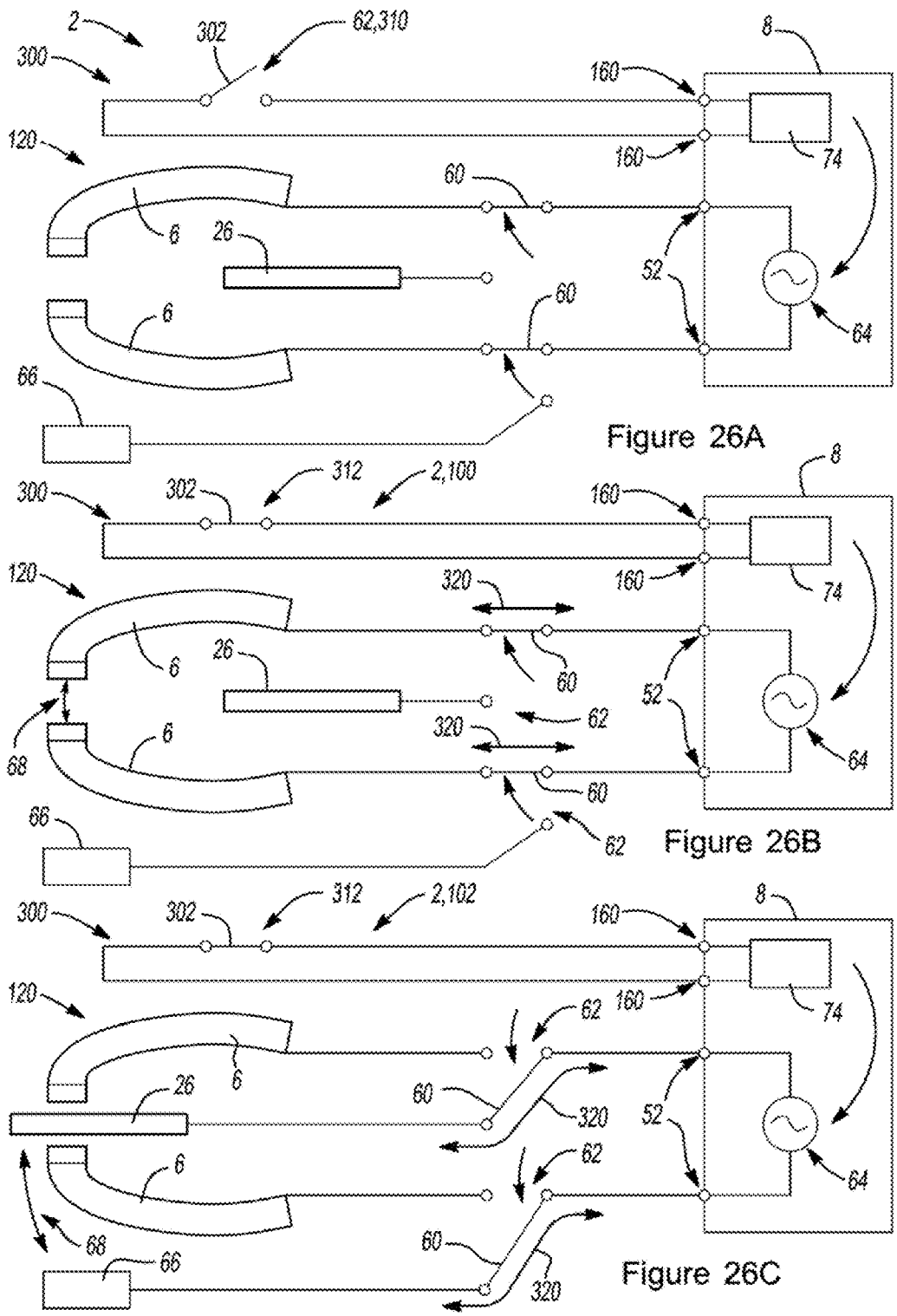

COMBINATION ELECTROSURGICAL DEVICE

FIELD

The present teachings generally relate to an electrosurgical device that can supply both monopolar power and bipolar power during a surgical procedure, and specifically to electrical forceps that can be mechanically reconfigured and/or electronically reconfigured to provide both monopolar power and bipolar power during open surgery.

BACKGROUND

Typically, electrosurgical devices have stand-alone monopolar capabilities or bipolar capabilities. Thus, a surgeon before a procedure begins may select either a device with monopolar capabilities or a device with bipolar capabilities and the surgeon can use the device to apply either monopolar power or bipolar power. For example, if the surgeon selects a monopolar device and monopolar power is not desired for the surgical procedure the surgeon may use either the device that supplies monopolar power to perform the procedure or switch to a device with bipolar capabilities. Both of these devices may be used to perform the procedure, however, switching between devices and/or using a device that may be better suited for a different purpose may disturb the procedure flow, cause unnecessary delays in the procedure, and in some cases result in less than optimal energy sources being used.

Generally, electrosurgical devices are connected to a generator that produces a therapy signal and provides power to the electrosurgical device so that a therapy current is produced. However, the therapy currents that may be used are limited by the generator and thus if the generator is only capable of producing a single therapy current then only one therapy current can be applied through the electrosurgical device. Additionally, a generator may be capable of producing two therapy circuits, but the electrosurgical device may only be capable of controlling and applying a single therapy current. Thus, the electrosurgical device may only apply a single therapy current. Some attempts have been made to produce a device that includes both monopolar capabilities and bipolar capabilities in a single device.

Examples of some electrosurgical instruments may be found in U.S. Pat. Nos. 6,110,171; 6,113,596; 6,180,386; 6,358,268; and 7,232,440; and U.S. Patent Application Publication Nos. 2005/0113827; 2006/0187512; 2006/0084973; and 2012/0123406 all of which are incorporated by reference herein for all purposes. It would be attractive to have an electrosurgical device that may be switched between a monopolar configuration and a bipolar configuration with one hand so that a user can easily perform a desired task without the need to disrupt the flow of a procedure. It would be attractive to have an electrosurgical device that may be used in open surgery as forceps and may be used for electrical cutting and/or hemostasis. What is needed is an electrosurgical device with both monopolar capabilities and bipolar capabilities where the monopolar capabilities are deactivated during use as a bipolar device and where the forceps are immobilized during use as a monopolar device. What is needed is an electrosurgical device that produces more therapy currents than a generator supplies signals (i.e., generator modes) to the electrosurgical device. What is needed is an electrosurgical device that is electrically reconfigurable so that the electrosurgical device has fewer activation buttons then signals that the generator supplies (i.e., generator modes) yet is capable of being electrically reconfigured to apply all of the signals from the generator.

SUMMARY

The present teachings meet one or more of the present needs by providing: an electrosurgical device comprising: (a) forceps including: (i) a first working arm and (ii) a second working arm; (b) a blade electrode; wherein the electrosurgical device is capable of being switched between a first electrical configuration so that the electrosurgical device delivers a first therapy current through the first working arm, the second working arm, or both, and a second electrical configuration so that the electrosurgical device delivers a second therapy current through the blade electrode; and wherein the first working arm and the second working arm of the forceps are immobilized in the second electrical configuration so that both the forceps and the first therapy current are disabled.

Another possible embodiment of the present teachings comprises: an electrosurgical system comprising: a handpiece including: (a) a first working arm, (b) a second working arm, and (c) a blade electrode; and an activation circuit having a first switch state and a second switch state, wherein a therapy current is conducted between the first working arm and the second working arm when the activation circuit is in the second switch state and the handpiece is in a first position; wherein the therapy current is conducted between the blade electrode, the first working arm, the second working arm, or a combination thereof and an adjacent handpiece component when the activation circuit is in the second switch state and the handpiece is in a second position; and wherein the therapy current is not conducted when the activation circuit is in the first switch state.

Yet another possible embodiment of the present teachings provides: an electrosurgical system comprising: a handpiece including: (a) a first power connector; (b) a second power connector; and (c) one or more moveable members having a first position and a second position; and an activation circuit having a first switch state and a second switch state, wherein the activation circuit in the first switch state does not allow either a first electrosurgical therapy signal or a second electrosurgical therapy signal to exit the handpiece; wherein when the activation circuit is in the second state and the one or more moveable members are in the first position the activation circuit allows the first electrosurgical therapy signal to exit the handpiece so that a first therapy current extends between the first power connector and the second power connector, and wherein when the activation circuit is in the second state and the one or more moveable members are in the second position the activation circuit allows the second electrosurgical therapy signal to exit the handpiece so that a second therapy current extends between the first power connector and the second power connector.

Another possible embodiment of the present teachings provides: a surgical device comprising: (a) a handpiece (b) forceps including: (i) a first arm and (ii) a second arm; (c) a blade; wherein the surgical device is changeable between a first configuration so that the first arm and second are configured as forceps and a second configuration so that the forceps are mobilized and the blade extends beyond the distal ends of the first arm and the second arm so the extendable blade is configured as a scalpel.

The teachings herein provide: an electrosurgical device comprising: (a) forceps including: (i) a first working arm and (ii) a second working arm; (b) a blade electrode that is movable between a first position and a second position;

wherein the electrosurgical device is capable of being switched between a first electrical configuration so that the electrosurgical device delivers a first therapy current through the first working arm, the second working arm, or both, and a second electrical configuration so that the electrosurgical device delivers a second therapy current through the blade electrode; and wherein the blade electrode includes a slider that moves the blade electrode between the first position and the second position.

The teachings herein provide: an electrosurgical device comprising: a handpiece including: (i) a first working arm and (ii) a second working arm; wherein the handpiece is covered by a movable housing that secures the first working arm to the second working arm; wherein the proximal and where the two arms are secured together form a concave cross-section that creates a cavity when the arms are closed; and wherein the handpiece is configured as forceps that are movable between an open position and a closed position.

The teachings herein provide: an electrosurgical device comprising: a blade electrode that is movable between a first position and a second position; wherein the electrosurgical device is capable of being switched between a first configuration, and a second configuration so that the electrosurgical device delivers a therapy current through the blade electrode; and wherein the electrosurgical device include a spring pin that extends into contact with the blade electrode so that power is provided to the blade electrode through the spring pin when the blade electrode is in the second position.

The teachings herein provide an electrosurgical device that may be switched between a monopolar configuration and a bipolar configuration with one hand so that a user can easily perform a desired task without the need to disrupt the flow of a procedure. The teachings herein provide an electrosurgical device that may be used in open surgery as forceps and may be used for electrical cutting and/or hemostasis. The teachings herein provide an electrosurgical device with both monopolar capabilities and bipolar capabilities where the monopolar capabilities are deactivated during use as a bipolar device and where the forceps are immobilized during use as a monopolar device. The teachings herein provide an electrosurgical device that produces more therapy currents than a generator supplies signals (i.e., generator modes) to the electrosurgical device. The present teachings provide an electrosurgical device that is electrically reconfigurable so that the electrosurgical device has fewer activation buttons then signals that the generator supplies (i.e., generator modes) yet is capable of being electrically reconfigured to apply all of the signals from the generator.

BRIEF DESCRIPTION OF THE DRAWINGS

FIG. 2B illustrates a close-up view of the blade electrode immobilized between the working arms;

FIG. 2C illustrates a cross-sectional view of the electrosurgical device of FIG. 2A;

FIG. 2D1 illustrates a close-up view of a spring pin in FIG. 2C when the blade electrode is extended;

FIG. 2D2 illustrates a close-up view of a spring pin when the blade electrode is retracted;

FIG. 3A illustrates an exploded view of the electrosurgical device of FIG. 1;

FIG. 20A1 illustrates a schematic of a bipolar configuration with switches and power passing between working arms;

FIG. 20A2 illustrates a schematic of a bipolar configuration with a central processing unit and power passing between working arms:

FIG. 20A3 illustrates a schematic of a bipolar configuration:

FIG. 20B illustrates a schematic of the electrosurgical device with power passing between the blade electrode and the working arms;

FIG. 26A illustrates a circuit diagram of the electrosurgical device in the off position and the electrosurgical device including a ground pad;

FIG. 26B illustrates a circuit diagram of the electrosurgical device in bipolar configuration with the ground pad in an off state;

FIG. 26C illustrates a circuit diagram of the electrosurgical device in a monopolar configuration with the ground pad in an on state;

DETAILED DESCRIPTION

Figure 1:
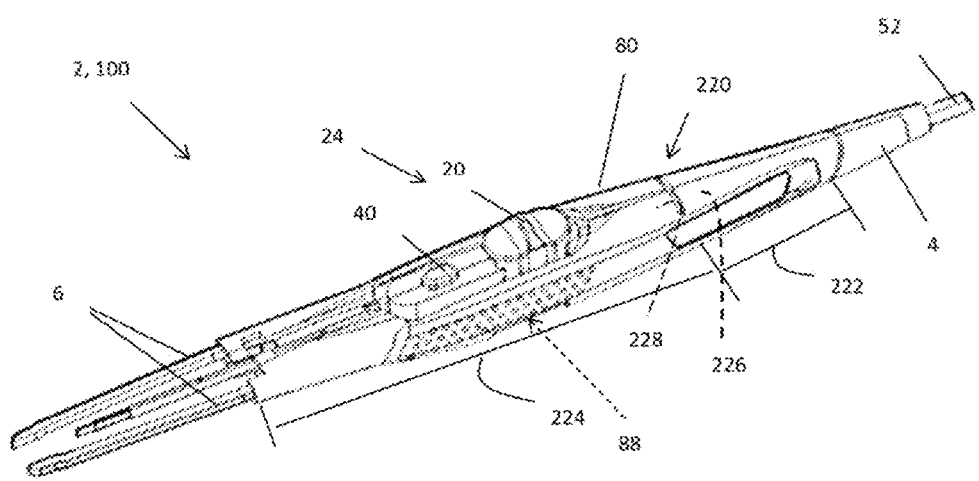
FIG. 1 illustrates an electrosurgical device in a bipolar configuration.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present application claims priority to U.S. Provisional Patent Application Ser. Nos. 61/787,731, filed on Mar. 15, 2013 and 61/845,664, filed on Jul. 12, 2013, the contents of which are both incorporated by reference herein in their entirety for all reasons. The present teachings relate to an electrosurgical device. Preferably, the present teachings relate to an electrosurgical device and associated componentry that form an electrosurgical system. The electrosurgical system may be any system that includes one or more of the devices taught herein. Preferably, the electrical surgical system includes at least an electrosurgical device. The electrosurgical system may include one or more handpieces as taught herein, one or more ground pads, one or more generators, one or more electrosurgical devices, one or more adjacent handpiece components, or a combination thereof and the teachings herein of each device which are incorporated into the electrosurgical system. The electrosurgical device may be any device that may be used by a surgeon to perform a surgical procedure. The electrosurgical device may function to be switched between two or more configurations, two or more states, or both. For example, the electrosurgical device may be switched between a monopolar configuration, a bipolar configuration, a non-electrosurgical configuration, or a combination of the three. The electrosurgical device may be any device that may be switched between two or more configurations with one hand so that a user may switch between the configurations without the need for a second hand, without disrupting the procedure, or both. The electrosurgical device may be any device and/or configuration that may be used ambidextrously, ambidextrously switched between configurations, or both. The electrosurgical device may be used to cut, perform hemostasis, coagulate, desiccate, fulgrate, electrocautery, or a combination thereof. The electrosurgical device may be any device that includes bipolar capabilities, monopolar capabilities, non-electrosurgical capabilities, or a combination thereof. The electrosurgical device may be used in open surgery. In addition to its electrosurgical capabilities the electrosurgical device may be used for non-electrosurgical purposes. For example, the electrosurgical device may be used as forceps, tweezers, or both that may be used to grip an object, an omen, a vein, skin, tissue, the like, or a combination thereof. In another example, one or more parts of the device may include a sharp edge and may be used to cut, similar to that of a scalpel. The electrosurgical device may include a handpiece and a generator. The electrosurgical device may have one or more therapy signals that extend between the handpiece and the generator.

The one or more therapy signals may be a signal, power, continuity, or a combination thereof. The one or more therapy signals may extend from the handpiece to the generator or vice versa. The one or more therapy signals may be formed by the handpiece, formed by the generator, or both. The electrosurgical therapy signals may be a therapy current. Preferably, the electrosurgical therapy signals indicate that a user has performed a step and a signal is being transmitted so that therapy current, energy, or both is generated. The electrosurgical therapy signals may provide a signal so that one or more therapy currents are produced and the therapy currents may be used for electrosurgery. The electrosurgical therapy signal may be conducted when the activation circuit is in the first switch state, the second switch state, a third switch state, the handpiece is in a first position, a second position, a third position, or a combination of switch states and handpiece positions. Preferably, a therapy signal is not generated, does not exit the handpiece, or both when the activation circuit is in the first switch state. The electrosurgical therapy signal may be a monopolar therapy signal, a bipolar therapy signal, or both. The electrosurgical therapy signal may be a monopolar therapy signal, a bipolar therapy signal, or both. The monopolar therapy signal may be any signal that has a voltage differential between a return port and an active port in the generator. The monopolar therapy signal may be any signal that when applied by the electrosurgical device extends from one pole of an electrosurgical device to another pole located at a remote location, off of the electrosurgical device, off the handpiece, or a combination thereof. The bipolar therapy signal may be any signal that has a voltage differential between two leads that are connected to the electrosurgical device, that are located in the generator, or both. The bipolar therapy signal may be any signal that when applied by the electrosurgical device extends from one component of a handpiece to another component of the handpiece (e.g., between two working arms, from a blade electrode to one or both working arms, or both). An electrosurgical therapy signal, when the activation circuit is in the second state, may exit the handpiece so that a therapy current extends from a blade electrode, between the first working arm and the second working arm, between the blade electrode and one or both of the working arms, or a combination thereof. The therapy signal may be generated and conducted from the handpiece to the generator.

The generator may be any device that supplies power, a therapy current, control signals, an electrosurgical therapy signal, electronically reconfigures itself in response to a signal from the user, physically reconfigures in response to adjustments by the user, or a combination thereof. The generator may function to be electrically connected to a handpiece to provide and/or receive electrosurgical therapy signals, power, therapy current, or a combination thereof. The generator may be capable of producing only a single therapy current. The generator may be capable of producing two therapy currents. The generator may include two or more power connections, three or more power connections, or four or more power connections. The power connections may be any port in the generator so that one or more power connectors of the handpiece may be plugged into so that power, control signals, therapy currents, or a combination thereof are supplied to the electrosurgical device. The generator may include one or more switches that may be switched between one or more of the power connections so that power, signals, or both may be selectively applied to the electrosurgical device based upon a desired configuration of the electrosurgical device. The generator may include a central processing unit (CPU), a series of internal switching, or both. The internal switching may provide a signal from an activation circuit to the voltage source so that the voltage source is supplied to the electrosurgical device and preferably the handpiece. The CPU may be interchanged with the internal switching and the switching may perform the same functions as the CPU. The CPU may be any device that provides power, signals, electrical reconfiguration, a switch between two or more therapy currents, a switch between two or more configurations, a switch between two or more therapy signals, or a combination thereof to the electrosurgical device so that the electrosurgical device may be used to perform a desired function as is discussed herein. The CPU may be used to switch the electrosurgical device between a first configuration, a second configuration, a third configuration, a monopolar configuration, a bipolar configuration, a non-electrosurgical configuration, or a combination thereof.

The first configuration, second configuration, and third configuration may be any configuration such that the electrosurgical device is mechanically reconfigured, electrically reconfigured, signally reconfigured and/or different, or a combination thereof. The first configuration, second configuration, and third configuration may be any of the various configurations discussed herein. The first configuration may provide a first therapy current. The first therapy current may be monopolar energy and/or monopolar current. Preferably, the first therapy current is bipolar energy and/or bipolar current. Bipolar energy may be any power source that during application extends from one pole of an electrosurgical device to another pole on the electrosurgical device. Stated another way, bipolar energy is energy that extends from one component of the handpiece to another component of the handpiece. For example, energy that extends between two working arms on the handpiece is bipolar energy, or energy that extends from a blade electrode to a working arm is a bipolar energy. The first electrical configuration may be deactivated by electrically disconnecting the one or more first activation buttons, electrically disconnecting all or a portion of an activation circuit, covering the one or more first activation buttons, electrically disconnecting the blade electrode, electrically disconnecting one or both of the working arms, shorting the blade electrode with a return pad, or a combination thereof. The second configuration may provide a second therapy current. The second therapy current may be bipolar energy (e.g., bipolar current or bipolar power). Preferably, the second therapy current may be monopolar energy (e.g., monopolar current or monopolar power). Monopolar energy may be any power source that during application extends from one pole of an electrosurgical device to another pole located at a remote location, off of the electrosurgical device, off the handpiece, or a combination thereof. Stated another way, bipolar energy is energy that extends from one component of the handpiece to a component that is not part of the handpiece. For example, energy that extends from a blade electrode to a ground pad is monopolar energy, or energy that extends from one or both working arms to a ground pad is monopolar energy. The second electrical configuration may be deactivated by electrically disconnecting the one or more second activation buttons, electrically disconnecting all or a portion of an activation circuit, covering the one or more second activation buttons, electrically disconnecting one or both working arms, electrically disconnecting the blade electrode, shorting the first working arm with the second working arm, or a combination thereof. The third configuration may be an electrosurgical configuration, a non-electrosurgical configuration, or both. Preferably, the third configuration is a non-electrosurgical configuration. The therapy current that extends through the handpiece may be effected by a signal and or current from the generator; a switch state of the activation circuit (e.g. first switch state, second switch state, third switch state, etc. . . . ); a hand piece position (e.g., first position second position, third position, etc. . . . ). For example, the therapy current may be monopolar energy when the handpiece is in the second position and the activation circuit is in the second switch state. However, the therapy current may be bipolar energy when the handpiece is in the second position. In another example, the therapy current may be a bipolar energy when the handpiece is in the first position and the activation circuit is in the first switch state. The first configuration, second configuration, and third configuration may be any configuration and/or may perform one or more of the functions as discussed herein for the monopolar configuration, bipolar configuration, non-electrosurgical configuration and each of those functions is incorporated herein. Preferably, as discussed herein the first configuration is a bipolar configuration, the second configuration is a monopolar configuration, and the third configuration is a non-electrosurgical configuration.

The non-electrosurgical configuration may be any configuration where power is not supplied to the handpiece, the blade electrode, the two or more working arms, or a combination thereof. The non-electrosurgical configuration may be used when the electrosurgical device is being used as forceps, tweezers, a scalpel, a clamp, Kelley hemostat forceps, or a combination thereof. In the non-electrosurgical configuration the working arms may be mobile. In the non-electrosurgical configuration the working arms may be immobilized, may immobilize the blade electrode, a cutting arm, an extendable arm, or a combination thereof. The cutting arm, the extendable arm, or both may be the blade electrode, may be a discrete arm that includes a sharp edge and may be alternated with the monopolar arm, or both. The non-electrosurgical configuration may be switched to a monopolar configuration or a bipolar configuration by pressing a button, turning a switch, advancing a cutting arm, advancing a blade electrode, advancing an extendable arm, or a combination thereof.

The device when in a monopolar configuration may supply power through a handpiece component (e.g., a blade electrode) and a return electrode that may be located at another location outside of the hand held portion of the electrosurgical device, through a handpiece component and an adjacent handpiece component, or both. The monopolar configuration may be any configuration where the electrosurgical device may be used to apply monopolar power. The monopolar configuration may be used to cut tissue, coagulate blood and/or fluids, electrical cutting, hemostasis, apply power to a large area, or a combination thereof. The monopolar configuration may be used to heat a specific area, heat an object between both electrodes, in contact with both electrodes, or a combination thereof. A monopolar configuration may be used so that power during use extends from a blade electrode to one or both bipolar electrodes, one or more immobilization arms, one or more working arms, one or more ground pads, or a combination thereof so that the blade electrode may be used for delicate electrosurgery localized electrosurgery, coagulation, cutting, or a combination thereof. The blade electrode may be used for less delicate procedures, less localized electrosurgery, or both when compared to bipolar electrosurgery.

The device when in a bipolar configuration may supply power from one portion of the device to a second portion of the device so that the return path for the power is relatively short when compared to the monopolar configuration. The bipolar configuration may be any configuration where the electrosurgical device may be used to apply bipolar power. The device when in the bipolar configuration may supply power between two localized handpiece components such as two working arms. The bipolar configuration may be used to coagulate, for hemostasis, cutting, fulguration, or a combination thereof. When in the bipolar configuration the electrosurgical device may include two opposing working arms. The two opposing working arms may be configured as forceps.

The forceps may function to grip, hold, squeeze, or a combination thereof one or more objects. The forceps may include one or more finger grips (i.e., configured like scissors) that may be used to move the forceps so that they may be used to grip one or more objects. The forceps may be free of finger grips and be actuated by direct pressure being applied to opposing sides of the forceps so that the forceps close and grip an object. The forceps include at least two working arms.

The working arms may function to grip, hold, squeeze, or a combination thereof an object when the object is between the two or more opposing working arms. The working arms may include one or more gripping features that may assist in gripping, holding, squeezing, or a combination thereof an object. The working arms may be movable between two or more positions. Preferably, the working arms are movable between at least a first position and a second position. For example, the working arms may be movable between a bipolar configuration (e.g., first position) and a monopolar configuration (e.g., second position). The working arms in the first position may be off, energized, one working arm may be energized, or a combination thereof. The working arms in the second position may be off, one or both of the working arms may be electrically disconnected, one or both of the working arms may be electrically connected, one working arm may be shorted by the other irking arm, or a combination thereof. More preferably, in the second position the working arms are immobilized so that the working arms cannot be used a forceps. The working arms may be longitudinally static and moveable relative to each other. The working arms may be longitudinally moveable and may be moveable relative to each other so that a gripping force may be created. For example, the working arms when in a bipolar configuration may both be extended and then retracted so that a blade electrode may be exposed forming a monopolar configuration. The working arms may be retractable and/or extendable simultaneously, or both. The working arms may be selectively retractable and/or extendable so that one or more tip regions are exposed.

The working arms may include a tip region. The tip region may include a portion that is configured to assist in facilitating gripping, holding, squeezing, or a combination thereof. Additionally, the tip region may be configured in one or more electrosurgical configurations (e.g., a monopolar configuration, bipolar configuration, or a combination of both). The tip region may include teeth, serrations, mouse teeth, be free of teeth (i.e., smooth), or a combination thereof. The tip region may be fully and/or partially insulated. Preferably, the tip region includes insulation on the non-contact portions of the working arms so that electrosurgical energy is not transferred through incidental contact. The working arms may include an active portion and an inactive portion (i.e., an insulated portion).

The active portion may function to apply power. The active portion may be the same portion as the contact regions of the forceps. Thus, for example, when tissue is grasped between the contact portions of the forceps, power may be supplied to the tissue through this contact portion. The active portion of the working arms preferably is between the two opposing working arms and the active portion of the blade electrode is the portion that extends beyond the working arms, out of the channel, or both. The active portions may be substantially surrounded by inactive portions or portions that are insulated. The inactive portion may be any portion that does not supply power, that is insulated, or both. The inactive portion may be any portion that may transfer power through incidental contact and thus are insulated so that incidental transfer of power does not occur and/or stray current is prevented. For example, an outside of the working arms may be coated with an insulating material so that if the working arms accidentally contact tissue proximate to the tissue of interest the proximate tissue is not subjected to a transfer of power. The inactive portion and the active portion may be made of different materials, coated with different materials, or both.

The working arms may be made of any material that may be used to grip, hold, squeeze, or a combination thereof and provide monopolar power, bipolar power, a therapy current, a gripping force, or a combination thereof to a desired location. The working arms may be made of one material and the tip region of each working arm may include, be coated with, or both one or more materials that may be insulating, a higher conductivity than the base material, a lower conductivity than the base material, or a combination thereof. The one or more working arms may include one or more materials along the length of the working arm. For example, the working arms may be entirely made of stainless steel. Preferably, each working arm includes two or more materials. For example, the working arms may have a base material of stainless steel and the working arms may be coated with an insulating material such as silicone or polytetrafluoroethylene (PTFE). The working arms may include any material that is safe for use in a surgical procedure, and preferably and electrosurgical procedure. The working arms may include metals, plastics, a polymer, an elastomer, gold, silver, copper, titanium, aluminum, iron based metals, stainless steel, silicone, polytetrafluoroethylene), insulating polymers, rubber, or a combination thereof. Preferably, each working arm is substantially coated with an insulating material except for a contact region between the two working arms where the working arms contact each other. The working arms may be coated in regions where the user contacts the working arms. The working arms may have an active portion and a passive portion, an inactive portion, or both. For example, the active portion may be the metal that extends through the working arms and is used to provide monopolar energy, bipolar energy, gripping capabilities, holding capabilities, squeezing capabilities, or a combination thereof. The passive portion may be a portion that houses the active portion. The passive portion may be a housing.

The working arms may be located within a housing. The housing may be any part of the device that may include one or more working arms and be gripped by a user during use. The housing may electrically connect, mechanically connect, or both the two working arms. The housing may be a pivot point so that the two working arms may be moved when the housing is compressed. The housing may substantially surround the working arms so that only the tip region extends out of the housing and are exposed. The housing may surround an outer side of the working arms and an inner side of the working arms may be exposed so that as the blade electrode is extended between the two working arms, the blade electrode contacts one or both of the working arms. The housing may include a gripping portion. The gripping portion, upon and application of pressure, may close the working arms and upon a release of pressure the working arms may return to an open position. The gripping portion may assist the user in holding the electrosurgical device like a pencil. The electrosurgical device may include an outer housing and an internal housing. The internal housing may include, surround, encapsulate, encase, house, or a combination thereof, one or more internal features of the electrosurgical device. The internal housing may house electrical components such as wires, terminals, plugs, printed circuit boards, spring pins, or a combination thereof. The internal housing may function to provide water resistance to the electrical components. The internal housing may extend through a through hole in the shuttle; provide a guide for the shuttle to move along, or a combination thereof. The internal housing may be an integral part of the outer housing. The internal housing may be one or more discrete parts. The internal housing may be two or more pieces that are connected together. The internal housing may be connected to the external housing, housing one or more of the activation buttons discussed herein, or a combination thereof. The housing may be electrically connected to a power source and provide power to each of the working arms. The housing may be electrically insulating. The housing may include one or more hinges and/or one or more hinge portions.

The one or more hinges may function to connect to rigid pieces, impart flexibility into the working arms, the handpiece, the electrosurgical device, or a combination thereof. The one or more hinges may function to impart movement into the housing while allowing the housing to substantially cover the components of the handpiece. There may be a hinge on only one working arm or a hinge on each working arm. The housing may include a rigid stationary section, a movable section, a flexible hinge section, or a combination thereof. The rigid stationary section may be on a proximal end of the electrosurgical device (i.e., closest to the user). The rigid portion may not move when the working arms are moved about the hinge. The hinge may create a pivot point for a movable section to rotate about. The movable section may function to move so that a gripping force, a gripping movement, or both are created. The movable section may cover all or a portion of the working arms. Only a tip of the working arm may extend beyond the movable section of the housing. The movable section may be substantially rigid but may pivot about the hinge so that the section is movable and/or flexible. For example, the movable section of the working arm itself may not be flexible but the arm may be movable such that the movable section moves with the arm. The movable section may be on the distal side of the hinge (i.e., the side of the hinge farthest from the user). The movable section, the rigid stationary section, or both may form a movable connection, a rigid connection, or both with the hinge. Preferably, the movable section forms a movable connection and the rigid stationary section forms a rigid connection. The movable connection may function to allow a hinging action, movement back and forth, or both. The movable connection may create a force that opposes a gripping of the forceps so that the forceps default open. The movable connection may create a pivot point that opposes a rigid connection. The rigid connection may remain static while the movable connection moves about the rigid connection. The rigid connection may form a side of the hinge that anchors the hinge so that the hinge may move, flex, pivot, allow the arms to move, or a combination thereof. The hinge may be any shape so that the hinge moves. The rigid stationary section of the housing may have a general C-shaped cross-section to provide a shell to surround (the inner components of the forceps). Likewise the rigid moveable section may also have a C-shaped cross-section to provide a shell to surround (the inner components of the forceps. The hinge section may have slots in the outer portions of the C-shaped cross-section so that the cross-section of the hinge portion is substantially planar. The substantially planar cross-section may have tower bend resistance so that the hinge section is relatively flexible compared to the rigid stationary section and the rigid movable section. The hinge section may form a generally "T" shape. The housing may include one or more activation buttons, one or more activation circuits, one or more printed circuit boards and associated controls, one or more blade electrodes, one or more shuttles, one or re channels, one or more immobilization arms, one or more immobilizing features, one or re wires, one or more conductors, or a combination thereof.

The one or more immobilization arms, one or more immobilization features, or both may be any feature of the housing, the working arms, or both that may immobilize one or both working arms when the electrosurgical device is in the monopolar configuration. The immobilization arms may be connected to the housing and extend between one or both of the working arms and when the blade electrode is advanced the immobilization arms are separated and the working arms are moved into contact with each other. The immobilization arms may be connected to the housing and extend between one or both of the working arms and when the blade electrode is advanced the immobilization arms are compressed, pushed together, or both and the working arms are moved into contact with each other. The immobilization arms may be generally parallel to the working arms, may extend: in the same direction as the working arms, may extend away from the working arms, towards an opposing working arm, towards the user, away from a user, or a combination thereof. Preferably, the working arms and the immobilization arms form generally an "X" shape so that when one side of the "X" is moved outward the opposing side of the "X" is moved inward. For example, as the blade electrode is moved forward the blade electrode may include a wedge and the wedge may act to force the immobilizing arms apart so that the working arms are moved together. The working arm and the immobilization arms may form generally two "V" shapes. The two generally "V" shapes may extend generally in the same direction so that as one V is widened the other V is narrowed. The immobilization arms may overlap. The overlap portion may form the "V" shape. For example, one immobilization arm may extend from the housing, a first working arm, or both towards the second working arm, the housing proximate the second working arm, or both, and a second immobilization arm may extend from the housing, a second working arm, or both towards the first working arm and as an immobilization feature such as a wedge is moved between the first immobilization arm and the second immobilization arm the immobilization arms may be moved closer to the opposing working arm so that the working arms are moved into contact and immobilized. The housing, the working arms, or both may be free of immobilization arms.

The two or more working arms may be immobilized by an immobilization feature. The immobilization feature may be any feature that connects the two or more working arms together so that the arms are immobilized in the monopolar configuration, so that the forceps are disabled, or both. The immobilization features may be part of the arms, part of the housing, all or a part of the shuttle, or a combination thereof. The immobilization features may be a track that extends along all or a portion of each arm and as the shuttle is moved forward or backward to the monopolar configuration, each track may extend into communication with the shuttle so that each of the working arms are moved into contact with each other and vice versa from the bipolar configuration. The immobilization feature may be a lock, a fastener, a piece that houses all or a portion of the working arms, or a combination thereof that locks the two working arms together. The immobilization feature may be a piece that slides and compresses the working arms, a piece that twists and radially compresses the working arms, or a combination of both. The immobilization feature while being moved and immobilizing may move a blade electrode, may extend a blade electrode out a channel, or a combination of both.

The housing, the one or more working arms, or a combination of both may include one or more channels. The channel may be located at any location within one or more of the working arms so that one or more features may be extended through the channel. The one or more channels may end at a distal end (i.e., an end used for electrosurgery, farthest from a user, or both) of the housing, a working arm, or both. The channel may be an absence of material so that a device may be located within the channel and extend from the channel. The channel may house any device that may be selectively used during electrosurgery. The channel may be any shape to house one or more electrosurgical devices. The channel may be round, square, oval, diamond, the like, or a combination thereof so that during use a device may be extended through the channel for use. The device extended from the channel may be a mechanical cutting device, a suction port, a smoke evacuation pot, a blade electrode, a moveable member, or a combination thereof. Preferably, a blade electrode is extended out of the channel so that the blade electrode may be used.

The blade electrode may be any device that may be used to apply monopolar power during a procedure, that may be longitudinally movable, rotationally movable, extendable, retractable, or a combination thereof. The blade electrode may be static. Preferably, in one embodiment the blade electrode may be static and the working arms moved relative to the blade electrode so that when the working arms are moved the blade electrode is exposed. More preferably, the blade electrode is a movable. The blade electrode may have a first position (e.g., retracted) and a second position (e.g., extended). The first position may be where the blade electrode is located relative to the working arms so that the working arms are past the blade electrode (e.g., the blade electrode is retracted so that the working arms extend past the blade electrode or the working arms are extended so that the working arms extend past the blade electrode). The first position may be where the blade electrode is electrically disconnected, electrically shorted relative to another handpiece component, electrically insulated so that power cannot pass from the blade electrode, or a combination thereof. The second position may be where the blade electrode is located relative to the working arms so that the blade electrode is extended beyond the working arms (e.g, the blade electrode is extended so that the working arms are located proximate to the user or the working arms are retracted so that the blade electrode is beyond the working arms). The second position may be where the blade electrode is electrically connected, supplies a therapy current, is electrically continuous, or a combination thereof. The blade electrode may be a separate piece that when activated may be used to supply monopolar power. The blade electrode may be formed by connecting the two working arms together and supplying power through only one working arm. The blade electrode may be used for electrically cutting, mechanically cutting, or both. The blade electrode may be a discrete third working arm that may extend from one of the working arms, between the working arms, or both.

The blade electrode may be made of the same material as one or both of the forking arms. Preferably, the working arms and the blade electrode are made of different materials. The blade electrode may be made of one material. Preferably, the blade electrode includes two or more materials. The blade electrode may be made of stainless steel, copper, silver, titanium, a metal, a surgical steel, a metal with good thermal dissipation properties, a metal with poor thermal dissipation properties, a material with high thermal conductivity, or a combination thereof. The blade electrode may include a material with a first thermal conductivity and the working arms may include a material with a second thermal conductivity. It is contemplated that the blade electrode, the working, arms, or both may include both a material with a first thermal conductivity and a second thermal conductivity. The materials with the first conductivity and the second conductivity may be any of the materials discussed herein. The material with the first thermal conductivity may have a lower thermal conductivity than the material with the second thermal conductivity. Preferably, the material with the first thermal conductivity has a higher thermal conductivity than the material with the second thermal conductivity. The blade electrode may include a coating. The coating may be any coating that provides insulating properties, provides improved thermal dissipation of a base material, prevents corrosion, or a combination thereof. The coating may be a polymer, an elastomeric, silicone, polytetrafluorethylene (PTFE) the like, or a combination thereof. The coating may extend over substantially all of the blade electrode except for an active region of the blade electrode. The blade electrode may include one or more insulator sleeves that cover all or a portion of the blade electrode, the blade electrode may be movable into and out of an insulator housing.

The insulator housing may function to prevent power and/or stray power from extending to and or from the blade electrode when the blade electrode is located within the insulator housing. The insulator housing may receive all or a portion of the blade electrode. The insulator housing may substantially surround all of the blade electrode when the blade electrode is in a retracted position, a bipolar configuration, or both. The insulator housing may insulate the blade electrode from stray current from the working arms, the ground pad, or both. The insulator housing may be a static component and the blade electrode may move relative to the insulator housing. The insulator housing may be made of insulative material so that the flow of current to and/or from the blade electrode is substantially prevented. The insulator housing may be made of and/or include rubber, plastic, silicone, an elastomer, silicone, PTFE, or a combination thereof. The insulator housing may be used instead of or in addition to an insulator sleeve so that the blade electrode is isolated and/or stray current is prevented.

The insulator sleeve may prevent power from passing to and/or from the blade electrode. Preferably, the insulator sleeve prevents power from passing to and/or from the blade electrode when the blade electrode is retracted so that the blade electrode is not powered, a circuit cannot be completed, or both. The insulator sleeve may be a sleeve that covers a portion of the blade electrode. The insulator sleeve may move with the blade electrode so that the same portions of the blade electrode are always covered and the same portions of the blade electrode are always exposed. The insulator sleeve may be an integral part of the blade electrode. The insulator sleeve may be fixedly connected to the blade electrode. The insulator sleeve may isolate portions of the blade electrode so that current and/or stray current are prevented from passing to and/or from the insulated portions of the blade electrode. The insulator sleeve may be located on the blade electrode so that when the blade electrode, the working arms, or both are in contact and/or immobilized the working arms contact the insulator sleeve. The insulator sleeve may located proximate to a contact portion. The contact portion may contact wiring, a pin, a spring pin, or a combination thereof when the blade electrode is extended so that power passes through the blade electrode. The contact portion may be free of the insulator sleeve. For example, the blade electrode may have an insulator sleeve and a contact portion that are adjacent each other and when the blade electrode is full extended a spring pin may contact the contact portion and when the blade electrode is fully retracted the spring pin may contact the insulator sleeve. The insulator sleeve may be made of any material that prevents power from passing into the blade electrode. The insulator sleeve may be any thickness so that power is prevented from entering the blade electrode thorough the insulator sleeve. The insulator sleeve may be connected to a monopolar insulator. The insulator sleeve may prevent a spring pin from providing power to the blade electrode when the blade electrode is retracted and the contact portion may allow the spring pin to power the blade electrode when the blade electrode is extended.

The spring pin may function to move (e.g., vertically) so that as a part of varying thickness is moved, a constant contact is created between two devices. The spring pin may create contact between one or more moving parts so that power may be transferred from one part to the one or more moving parts. The spring pin may include one or more springing portions that accommodate for a change in size and/or shape of a part. The one or more springing portions may create a movable connection. The one or more springing portions may allow for movement of one part relative to the other part. The springing portion may extend from a body portion. The body portion may assist in connecting the spring pin within a system, provide a connection point for one or more other components, or both. The body portion may include one or more connection arms that connect the spring pin to circuitry. Preferably, the body portion includes two connection arms that connect to a printed circuit board. The springing pin may extend when the insulator sleeve is extended and the contact portion is moved proximate to the spring pin. The spring pin may move out of the way when the blade electrode is retracted and the insulator sleeve is moved to a retracted position. The blade electrode may include a monopolar insulator.

The monopolar insulator may be any device that may insulate all or a portion of the active portions of the working arms. The monopolar insulator may prevent the working arms from contacting, the blade electrode when the electrosurgical device is in the bipolar configuration. The monopolar insulator may be moved into contact with one or both of the working arms amid immobilize the working arms so that the working arms cannot be used as forceps. The monopolar insulator may prevent power from being transferred from one or both of the working arms to the blade electrode. The monopolar insulator may prevent stray current from being conducted from the working arms to a surrounding area, the blade electrode, the ground pad, or a combination thereof. During a change from a bipolar configuration to a monopolar configuration the monopolar insulator may extend between the working arms and once past the working arms a bias device may act to retract the monopolar insulator so than the tips of the working arms are pressed into a portion of the monopolar insulator and immobilized.

The bias device may be any device that may act to retract and/or advance one or more components of the electrosurgical device. The bias device may act to separate the working arms of the electrosurgical device when in the bipolar configuration. The bias device may push the blade electrode and/or shuttle forward into a monopolar configuration, pull the blade electrode and/or shuttle back from a monopolar configuration, or a combination thereof. The bias device may ensure that the shuttle, blade electrode, working arms, monopolar electrode, blade, or a combination thereof are in a fully extended and/or fully retracted state. For example, if a user moves a shuttle towards a forward position and stops short, the bias device may complete the movement to a final position. The bias device may assist in moving any of the devices and/or features discussed herein so that the devices and/or features are bi-stable. For example, the bias device may ensure that the blade electrode is always either fully extended or fully retracted and not located therebetween. The bias device may be a spring, a piece of rubber, an elastomeric piece, a bend in metal that forms a bias surface, or a combination thereof. If the bias device is bent metal the metal may be bent forming more than one plane. The first plane may contact a first surface and the second arm may contact a second surface so that two opposing electrosurgical components are moved. The bias device may be connected to the blade electrode, a shuttle, between the working arms a device that extends through the channel, or a combination thereof.

The shuttle may function to cover one or more activation buttons, moves one or more activation arms, moves the blade electrode, moves one or both working arms, immobilizes and/or electrically disconnects one or more features of the electrosurgical device and/or activation circuit, immobilizes one or more activation buttons, impedes movement and/or depression of one or more activation buttons, move one or more immobilization arms, or a combination thereof. The shuttle may be a shield that covers the activation buttons that are not in use so that one or more of the activation buttons are protected from contact. For example, when the electrosurgical device is configured for bipolar use the shuttle may cover the monopolar activation buttons and expose the bipolar activation buttons or vice versa. The shuttle may be a solid piece. Preferably, the shuttle includes a through hole so that one or more components may extend through the through hole, be covered by the parts of the shuttle adjacent the through hole, guided by the through hole, or a combination thereof. The shuttle may include a device that extends under, around, through, or a combination thereof one or more activation buttons so that movement of the one or more activation buttons is impeded, prevented, or both. For example, when the shuttle is moved a portion of the shuttle may extend under one or more of the one or more activation buttons so that a user is unable to depress the button to provide power, electricity, a therapy current, or a combination thereof. The shuttle may include one or more positions. Preferably, the shuttle includes at least a first position and a second position a first electrical configuration and a second electrical configuration). The shuttle in the first position, the second position, or both may perform any of the functions discussed herein for the shuttle. The shuttle may be moved by sliding on a track. The shuttle may be a slider assembly that moves the blade electrode.

The slider assembly may function to move the shuttle in one direction and the blade electrode in an opposing direction. The slider assembly may have a gear ratio so that for every unit of measurement the slider assembly is moved the blade electrode moves two units of measurement. The slider assembly may include a rack and pinion system that is connected to the shuttle. The slider assembly may include one or more racks. The shuttle may be connected to one rack and there may be an opposing rack that is offset. The slider assembly may include one or more pinions and preferably two pinions that extend between and into contact with one or more racks. Preferably, one pinion contacts one rack and the other pinion contacts the second rack and the pinions are interconnected. The shuttle when moved in a first direction may rotate the first pinion and the first pinion may rotate the second pinion and the second pinion may drive the second rack in an opposing direction as the first rack and shuttle are moving. The pinions may have a gear ratio. The gear ratio may be 1:1, 1;1.1 or more, 1:1.5 or more, 1:2 or more or even 1:5 or more (i.e., on pinion moves 5 revolutions for every 1 revolution of the other pinion). The shuttle may not include a slider assembly and may be directly driven.

The shuttle may be connected to one or more other devices that may be retracted. For example, the shuttle may be connected to the blade electrode and the shuttle may be used to move the blade electrode into and/or between a monopolar configuration and a bipolar configuration. In another example, the shuttle may be connected to the working arms so that when the shuttle is moved the working arms are extended and/or retracted. The shuttle may be integrally connected to the blade electrode. The shuttle may include one or more electrical connectors. The one or more electrical connectors may function to pass power from a wire to am electrosurgical component. For example, a wire may connect to an electrical connector and the electrical connector may power the blade electrode. The one or more electrical connectors may move with the shuttle so that as the shuttle is extended or retracted the electrosurgical device is electrically reconfigured through the mechanical movement. In another example, movement of the shuttle in the forward position may electrically connect the ground pad to a power source and retraction of the shuttle may electrically disconnect the ground pad from the power source. The shuttle may have 2, 3, or even 4 electrical connectors. The shuttle may include an electrical connector for the first working arm, the second working arm, the ground pad, and the blade electrode. The shuttle may lock a device in a position, immobilize one or more working arms, or both. For example, the shuttle may lock the blade electrode in a retract position when the electrosurgical device is in a bipolar configuration, in another example, the shuttle may lock the blade electrode in a forward position and immobilize both of the working arms when the electrosurgical device is configured for monopolar use. The shuttle may lock by a detent, a projection that locks in a corresponding recess, a mechanical interlock, a friction fit, a mechanical lock, or a combination thereof. This shuttle may be connected to one or both working arms of the electrosurgical device. The shuttle may be connected to the housing and slide on a track so that when the shuttle is extended towards a monopolar position all or a portion of each working arm is contacted by the shuttle so that the arms are moved, immobilized, or both. The shuttle may include a wedge, a ring, or both.

The wedge, the ring, or both may be a device for moving one or both of the immobilizing arms, one or both of the working arms, or a combination thereof so that the working arms are immobilized in the monopolar configuration. The wedge may be any device that assists in immobilizing the working arms, moving the immobilization arms, or both. The wedge may have any shape so that the wedge when moved assists in moving one or more immobilizing arms without having a step of separating the immobilizing arms. The wedge may have a tapered shape with a point on one end so that the wedge fits between the two opposing immobilizing arms and as the wedge is gradually progressed between the immobilizing arms the wedge becomes wider moving the immobilizing arms apart. The wedge may be generally triangular in shape. The wedge may have a shape that is a mirror image to the shape formed between the immobilization arms so that when the tip of the wedge reaches the pointed portion between the immobilization arms the wedge is prevented from moving further forward. The wedge may be located at any location on the electrosurgical device, the shuttle, or both so that when the wedge is moved between the immobilization arms the wedge immobilizes the working arms. The shuttle may be free of a wedge and may include a ring.

The ring may be any device that assists in immobilizing the working arms. The ring may extend around all or a portion of the periphery, a perimeter, or both of the electrosurgical device, the working arms, the immobilization arms, or a combination thereof. The ring may move along the outside of the electrosurgical device so a portion of the electrosurgical device is located within an inner portion of the ring. The ring may be a complete circle, a partial circle, "U" shaped, fully surround a length of the device, partially surround a length of the device, or a combination thereof. The ring may be part of the shuttle, may be the shuttle, may be discrete from the shuttle, may assist in moving the blade electrode, may cover one or more of the activation buttons, may extend under the one or more activation buttons, may extend through one or more activation buttons, deactivate all or a portion of an activation circuit, may fully and/or partially surround one or more of the immobilization arms, or a combination thereof.

The activation circuit may be any part of the electrical surgical system, handpiece, or both that may be activated so that one or more therapy currents are generated, applied, supplied, prevented from being supplied, or a combination thereof. The activation circuit may electrically connect two or more components, electrically activate two or more components, provide a user interface, or a combination thereof. The activation circuit may have one or more switch states, two or more switch states, or three or more switch states. Preferably, the activation circuit has two switch states (e.g., on or off). The activation circuit, the switches, or both may have a neutral position where the activation switches are neither on nor off. The first switch state may be off, not provide a therapy signal, not provide a first therapy signal, not provide a second therapy signal, not provide a third therapy signal, or a combination thereof. The first switch state may prevent a therapy signal to be produced, prevent a therapy signal (e.g., a first therapy signal, a second therapy signal, etc. . . . ) from exiting a handpiece, prevent communication between the handpiece and the generator, or a combination thereof. The second switch state may be on, provide a therapy signal, provide a first therapy signal, provide a second therapy signal, provide a third therapy signal, or a combination thereof. The second switch state may provide a therapy current between the blade electrode, the first working arm, the second working arm, the ground pad, or a combination thereof; produce a therapy signal; allow a therapy signal to exit the handpiece; allow communication between the handpiece and a generator; or a combination thereof. For example, when the ground pad is electrically disconnected and the activation circuit is in the second switch state, a therapy current may be conducted between the blade electrode and the first working arm, the second working arm, or both working arms. In another example, when the activation circuit is in the second state and the blade electrode is in the second position the blade electrode may be electrically connected to a first power connector and a ground pad may be electrically connected to a second power connector. The activation circuit may include one or more switches that each include the switch states discussed herein. Preferably, the activation circuit includes one or more activation buttons and/or is one or more activation buttons that may be moved and/or activated into the one or more switch states discussed herein.

The one or more buttons may function to control one or more functions of the electrosurgical device. The one or more buttons may control the bipolar power, the monopolar power, a bipolar cut setting, bipolar coagulation setting, a therapy current, rotation of the blade electrode, rotation of the monopolar electrode, or a combination thereof. Preferably, a first button having a first color and/or configuration may be for applying bipolar power and a second button having a second color and/or configuration may be for applying monopolar power. The one or more buttons may be exposed and/or unlocked by the shuttle as the shuttle moves, the blade electrode moves, or both to and/or from a monopolar configuration to a bipolar configuration or vice versa. For example, the monopolar activation button may only be exposed when the shuttle, blade electrode, or both are in the monopolar configuration. The monopolar activation button, the bipolar activation button, or both may turn on power to the respective electrode so that power is supplied to the area of interest. The device may include only one activation button and may also include a selector.

The selector may function to select between one or more modes and/or one or more functions. Preferably, the selector allows a user to select between a plurality of different modes and/or functions. The selector may switch between one or more ports in the activation circuit and the one or more ports may communicate to a CPU the desired electrosurgical function to perform. The selector may be automatically moved when the blade electrode is extended and retracted. Preferably, the user may set the selector to a desired mode and/or function. The selector may power one or more functions and/or modes simultaneously. The electrosurgical device may include a button that locks the configuration of the blade electrode, allows the blade electrode to rotate, or both.

The blade electrode may be any part of the electrosurgical device that supplies power from one location and the power extends to a distal location. The blade electrode may be a combination of two or more devices that when combined may form a blade electrode. The blade electrode may be a discrete part that when electrically powered provides power. The blade electrode may be static, rotatable about its axis, longitudinally movable about its axis, or a combination thereof. The blade electrode may be blunt, have one or more sharpened edges, have dull edges, or a combination thereof. The blade electrode may rotate to any angle so that the blade electrode may be used to cut, be ergonomically oriented so that a user is not required to reposition their grip, used for vertical cutting, used for side to side cutting, or a combination thereof. The blade electrode may be rotated at an angle of about 15 degrees or more, about 30 degrees or more, about 45 degrees or more, about 60 degrees or more, or even about 90 degrees or more. The blade electrode may be rotated at an angle of about 275 degrees or less, about 225 degrees or less, about 205 degrees or less, or about 180 degrees or less. The blade electrode may maintain a complete circuit during rotation so that power may be applied through the blade electrode as the blade electrode is rotated.

The blade electrode, the bipolar electrode, or both may complete a circuit when in contact with tissue. The bipolar electrode may have two opposing working arms and the tissue may electrically connect the working arms, form an electrical bridge between the two arms, or both. The blade electrode may have a single blade electrode (i.e., a monopolar working arm) and the tissue may electrically connect the blade electrode with a return electrode, act as an electrical bridge between the blade electrode and the return electrode, act as an electrical bridge between the blade electrode and one or both of the bipolar electrodes, or a combination thereof. The blade electrode when extended may activate a circuit, a switch, or both.

The circuit may have a switch that switches between the monopolar configuration, the bipolar configuration, or both. The switch may activate one or more of the bipolar electrodes and deactivate the ground pad (i.e., return pad) or vice versa; activate one or more bipolar electrodes and deactivate the blade electrode or vice versa; deactivate one bipolar electrode and leave the bipolar electrode open (i.e., not powered); deactivate the blade electrode and leave the blade electrode open; deactivate bath bipolar electrodes and activate the blade electrode and the return electrode or vice versa, deactivate the ground pad; all of the bipolar electrodes, and the blade electrodes; or a combination thereof. The blade electrode, one or more of the bipolar electrodes, or a combination thereof may be connected to an alternating current power source, a direct current power source, or both. Preferably, the blade electrodes, the bipolar electrodes, or both are connected to an alternating current power source. The blade electrode may be free of a position between the bipolar electrodes when the electrosurgical device is in the bipolar configuration. The blade electrode may be positioned between the bipolar electrodes, extended beyond the bipolar electrodes, be static and the working arms retracted so that the blade electrode is extended beyond the working arms, or a combination thereof when in the monopolar configuration. The bipolar electrodes when in a monopolar configuration may act to electrically insulate the Wade electrode from the surrounding regions, the handpiece, or both.

The handpiece may be any part of the device that the user grips, that houses one or more of the control buttons, one or more switches, one or more electrical connectors, one or more diodes, one or more capacitors, or a combination thereof. The handpiece may house all or a portion of the control circuitry, a central processing unit, or both. The handpiece may electrically connect the electrosurgical device, the electrical system, or both to the generator. The handpiece may both physically connect the functional elements of the electrosurgical device and electrically connect the elements of the electrosurgical device. The handpiece may be a body portion of the electrosurgical device, a portion between the two or more working arms, a connector between the two or more working arms, that houses all or a portion of the circuitry, that includes an activation circuit, that includes one or more control buttons, or a combination thereof. Preferably, the handpiece is the portion that a surgeon grips and presses one or more buttons to apply power to a desired location. More preferably, the handpiece is a central portion that includes both buttons and one or more electrical connectors for supplying power to the electrosurgical device, the working arms, the blade electrode, or a combination thereof. The handpiece may include one or more movable members, one or more handpiece components, or both.

The one or more movable members may be any part of the handpiece that may be moved between two or more positions. The one or more movable members may be moved between a first position and a second position. The one or more movable members may be moved between a monopolar configuration and bipolar configuration. The one or more movable members may be any part of the electrosurgical device and/or electrosurgical system that may be electrically reconfigured, mechanically reconfigured, or both. The one or more movable members may be a monopolar electrode, a first working arm, a second working arm, a ground pad, or a combination thereof. The one or more movable members may be electrically connected to a first power connector, a second power connector, or both. The moveable member may be moved between one or more of the positions discussed herein for the monopolar electrode, the bipolar electrode, or both and the activation circuit between one or more switch states as discussed herein so that the moveable member is electrically configured, mechanically configured, or both in the same configuration as those respective components. The one or more movable members may be a handpiece component.

The one or more handpiece components may be any device that is directly electrically connected, physically connected, carried on, or a combination thereof to the handpiece. The one or more handpiece components may be any component that may mechanically reconfigure the handpiece, be mechanically reconfigured by the handpiece, moved along the handpiece, apply a therapy current from the handpiece, or a combination thereof. The one or more handpiece components may be electrically connected to the handpiece so that power, signals, therapy currents, or a combination thereof flow directly to and or from the handpiece from the handpiece component without travelling through an intervening device. The handpiece component may be located separate from the handpiece but electrically connected. The one or more handpiece components and handpiece may be electrically reconfigurable so that the handpiece and the handpiece component are electrically connected in some configurations and electrically disconnected in some configurations. The one or more handpiece components may be a blade electrode, the first working arm, the second working arm, the ground pad, the shuttle, a monopolar electrode, one or more bipolar electrodes, or a combination thereof. Preferably, in one configuration the ground pad is placed discretely from the handpiece but the ground pad is directly electrically connected to the handpiece such that when the handpiece is in a monopolar configuration the ground pad is electrically activated. The handpiece may provide power to the one or more handpiece components so that the handpiece components are not electrically connected directly to a power supply, a therapy current, a generator, or a combination thereof.

The power connectors may be any device that supplies power, a therapy current, or both from a power source to the electrosurgical system, the electrosurgical device, or both so that the electrosurgical system, electrosurgical device, or both may be used for electrosurgery. The electrosurgical system, electrosurgical device, the handpiece, or a combination thereof may include one or more, preferably two or more, or most preferably two power connectors supplying power to the electrosurgical system, electrosurgical device, the handpiece, or a combination thereof. The therapy current may be any current that is applied by the electrosurgical device and performs a predetermined function. The therapy current may be monopolar power, bipolar power, coagulation, cutting, hemostasis, or a combination thereof. The therapy current may be any application of power that is produced by the electrosurgical device. The therapy current may be any application of power that extends into and through the electrosurgical device from one or more power connectors. The therapy current may be supplied form a voltage source. The voltage source may be any supply of energy that performs one or more of the function discussed herein. The voltage source may be a direct current voltage source and preferably the voltage source is an alternating current voltage source. The power connectors may be wires, pieces of a conductor, or both. The electrosurgical device may include one or more power connectors, preferably two or more power connectors, more preferably three power connectors, or even four or more power connectors. For example, in a three power connector system the power connectors may be and/or connected to a positive pin, a negative pin, a return pin, or a combination thereof. In another example, in a four power connector system the power connectors may be and/or connected to a bipolar positive pin, a bipolar negative pin, a monopolar active pin, a monopolar return pin, or a combination thereof. Each of the power connectors may be directly connected to a power source, a generator, or both. For example, if the electrosurgical device has three power connectors and the generator has three power connections (e.g., a power port) each power connector may be plugged separately into its own power connection. Each power connector may be electrically connected to a single component of the electrosurgical device. Preferably, there are two power connectors supplying power to the electrosurgical device and the electrosurgical device is electrically reconfigured between a first position and a second position, a first switch state and a second switch state, or a combination of both so that a therapy current and/or power from one of the power connectors may be supplied to two or more components of the electrosurgical device. For example, when the handpiece is in the first position, power from the first power connector may be supplied to the first working arm and power from the second power connector may be supplied to the second working arm, and when the handpiece is moved into the second position, the first power connector may be electrically connected to the blade electrode and the second power connector may be electrically connected to the ground pad. One or more of the power connectors may be indirectly connected to the power source. For example, if the generator includes two power connections and the electrosurgical device includes three power connectors, two of the power connectors may be electrically connected together and plugged into a power connector. Two or more power connectors may be electrically connected by a jumper.

The jumper may function to electrically connect two or more power connectors so that the power connectors can be electrically connected, signally connected, or both to the generator. The jumper may be any device that connects two electrical connectors outside of the generator so that the two or more electrical connectors may be connected to the generator. The jumper may be any device that assists in connecting two or more electrical connectors to a power source a generator or both. The jumper may electrically connect to components, wires, connectors, or a combination thereof so that a single port may be used to power the components, wires, connectors, or a combination thereof. Two or more of the power connectors may be electrically connected inside of the handpiece, the generator, or both by one or more connectors.

The one or more connectors may be any device that internally connects two power connectors together. The one or more connectors may electrically connect the two or more working arms during use so that power may be applied through both working arms, so that a complete circuit is formed, or both. The one or more connectors may electrically connect both of the working arms together so that one electrical connector may be used to electrically connect both working arms and one electrical connector may extend to another component such as the ground pad, the blade electrode, or both.

The electrosurgical device, the activation buttons, the handpiece, activation circuit, or a combination thereof may include one or more diodes. The diodes may be in any configuration so that upon pressing of an activation button, movement of a switch, or both the generator, the electrosurgical device, or both measures a frequency, a change in frequency, or both so that the generator may determine the activation mode that is being powered. Preferably, the one or more diodes may be different so that the two or more different frequencies, shifts in frequency, or both are created so that a generator may determine which switches in the handpiece, the electrosurgical device, the activation buttons, or a combination thereof are open, closed, or both.

The electrosurgical device, generator, handpiece, or a combination thereof may include one or more transformers. The one or more transformers may be of any size and shape so that depending on the current path through the one or more transformers, around the one or more transformers, or both the voltage supplied through to the handpiece, the electrodes, the working arms, or a combination thereof may be varied. For example, when in a monopolar configuration the voltage may be directly delivered to the electrode and when in a bipolar configuration the transformer may step down the voltage delivered to the working arms. Conversely, the transformer may be used to increase voltage delivered to one or more electrodes.

As discussed herein various circuits may be created by electrically reconfiguring one or more components of the electrosurgical device, physically configuring one or more components of the electrosurgical device, or both. During use one or more switches may be opened and/or closed so that one or more open circuits, one or more closed circuits, or both may be formed. For example, a shuttle and blade electrode may be extended forward so that a connection is formed between the blade electrode and a power source and the ground pad and a power source so that a circuit is completed and an open circuit may be created between the power source and the working arms so that the working arms are not powered. The circuits may be configured so that a circuit is created between two or more components and the electrosurgical device may be used for a desired type of electrosurgery. The electrosurgical instrument may be configured so that power flows from the blade electrode to one or more working arms, both working arms, to the ground pad, or a combination thereof. The electrosurgical device may be configured so that power flows from one working arm to another working arm, from one or more working arms to the blade electrode, from one or more working arms to the ground pad, or a combination thereof. The electrosurgical device may be configured with one or more power connectors, preferably two or more power connectors, and more preferably three or more power connectors. Each of the power connectors may be connected to one or more components, two or more components, or even three or more components. Each power connector may be switched between one or more components, two or more components, or even three or more components. The method may include a step of immobilizing the blade electrode, a cutting arm, or both. The method may include a step of immobilizing one or more bipolar electrodes, one or more blade electrodes, or both simultaneously.

A method of switching the electrosurgical device between a bipolar configuration, a monopolar configuration, non-electrosurgical configuration, or a combination thereof. The method may include one or more of the steps discussed herein in virtually any order. The method may include a step of advancing a shuttle, advancing a blade electrode, retracting a shuttle, retracting a blade electrode, applying a ground pad, removing a ground pad, reconfiguring a circuit, or a combination thereof. The method may include a step of applying monopolar power and then immediately subsequently applying bipolar power. The method may include a step of cutting in a non-electrosurgical configuration and then applying either monopolar power or bipolar power to coagulate, cauterize, or both without a step of changing instruments. The method may include a step of cutting in a monopolar configuration and then coagulating, cauterizing, or both using bipolar energy without a step of changing instruments.

FIG. 1 illustrates an electrosurgical device 2. The electrosurgical device 2 includes a bipolar configuration 100 where the electrosurgical device is forceps 4. The forceps 4 include a housing 80 with a pair of working arms 6 that remain as forceps 4 in the bipolar configuration 100 when the shuttle 20 is in the bipolar position 24. The housing covers the active portions of the working arms 6 along at least a portion of their length so that power is not transferred through incidental contact. While the shuttle 20 remains in the bipolar position 24 (e.g., first position) the bipolar activation button 40 is exposed so that upon pressing the bipolar activation button 40 power travels into the forceps 4 via the power connectors 52 and the power extends between the pair of working arms 6. The housing 80 includes a hinge 220 that allows the working arms 6 to move relative to each other while the housing covers the electrodes of the working arms. The housing 80 is divided by the hinge 220 which has a rigid stationary section 222 on the proximal end of the electrosurgical device 2 and a movable section 224 on the distal end of the electrosurgical device 2 so that the working arms 6 are movable relative to each other. The hinge 220, as illustrated, is generally shaped and has a rigid connection 226 on the proximal end of the electrosurgical device 2 and a movable connection 228 on the distal end of the electrosurgical device 2. The hinge 220 allows the arms to move relative to each other while maintaining, the protection of the housing 80 over both working arms and a central portion of the electrosurgical device 2. As illustrated the movable section 224 of the housing 80 includes a gripping portion 88 so that a user, upon applying pressure to the gripping portion closes the working arms.

Figure 2A:
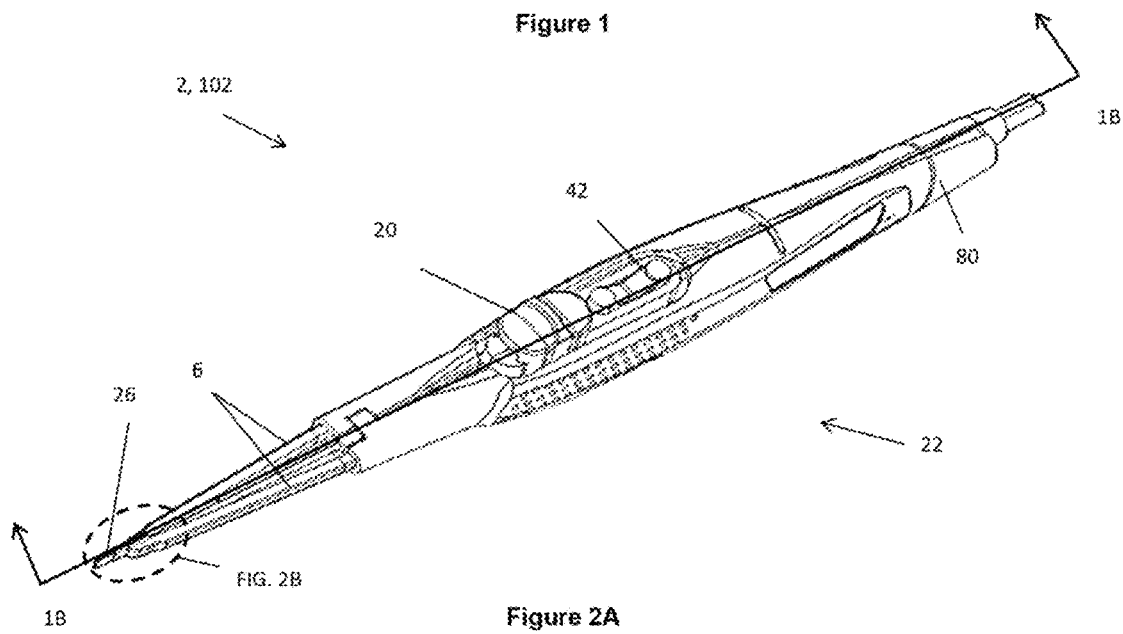
FIG. 2A illustrates the electrosurgical device of FIG. 1 in a monopolar configuration.

FIG. 2A illustrates the electrosurgical device 2 of FIG. 1 transformed into a monopolar configuration 102. The electrosurgical device 2 is changed into a monopolar configuration 102 when the blade electrode 26 is moved forward by the shuttle 20 sliding along the housing 80 and the blade electrode 26 is immobilized between the working arms 6. The shuttle 20 is ski forward into a monopolar position 22 (e.g., second position) so that one or more monopolar activation buttons 42 are exposed and the bipolar activation button is covered. When the monopolar activation button 42 is pressed power travels from the blade electrode 26 to a return electrode (not shown).

FIG. 2B illustrates a close-up view of the blade electrode 26 and working arms 6 immobilized in a monopolar position 22.

FIG. 2C illustrates a cross-sectional view of the electrosurgical device 2 of FIG. 2A with the blade electrode 26 in the extended position. The blade electrode 26 includes an insulator sleeve 54 that is extended forward with the blade electrode so that a contact portion 56 is aligned with the spring pin 250. The spring pin 250 is connected to a printed circuit board 260, which is in communication with the bipolar activation button 40 and the monopolar activation button 42. The spring pin 250 includes a springing portion 252 that maintains contact with the blade electrode 26 so that when the spring pin 250 contacts the contact portion 56 power is supplied through the blade electrode 26.

FIG. 2D1 illustrates a close-up view of a spring pin 250 in contact with a contact portion 56 of the blade electrode 26 when the blade electrode 26 is fully extended. The spring pin 250 transfers power from the printed circuit board 260 into the blade electrode 26 so that the blade electrode 26 is energized when the bipolar activation button 40, the monopolar activation button 42, or both are activated by a user.

FIG. 2D2 illustrates a close-up view of a spring pin 250 in contact with the insulator sleeve 54 of the blade electrode 26 when the blade electrode 26 is fully retracted (as is shown in FIG. 1). The spring pin 250 is prevented from transferring power from the printed circuit board 260 by the insulator sleeve 54 so that stray currents are not produced by the blade electrode 26 in the event that the bipolar activation button 40, the monopolar activation button 42, or both remain active and/or are activated by a user.

FIG. 3A illustrates an exploded view of the electrosurgical device 2 of FIGS. 2 and 3. The electrosurgical device 2 includes a housing 80 that when connected together retains all of the components so that the components are movable and function to produce therapy currents. The housing 80 substantially surrounds the working arms 6 so that only a portion is exposed for creating a therapy current. An internal housing 86 houses the power connectors 52 that supply power to the working arms 6 and the blade electrode 26. The internal housing 86, when assembled, extends through a through hole 32 in the shuttle 20 which is connected to the blade electrode 26. The internal housing 86 also contains a printed circuit board 260 with a plurality of sensors 44 that is electrically connected to the bipolar activation button 40 and the monopolar activation button 42 so that when the buttons are pressed power is supplied to a desired location via the spring pin 250 when the electrosurgical device 2 is in the monopolar configuration. The power connects 52 terminate at a pair of power connectors 10 that plug into a wall and/or generator (not shown).

Figure 3B:
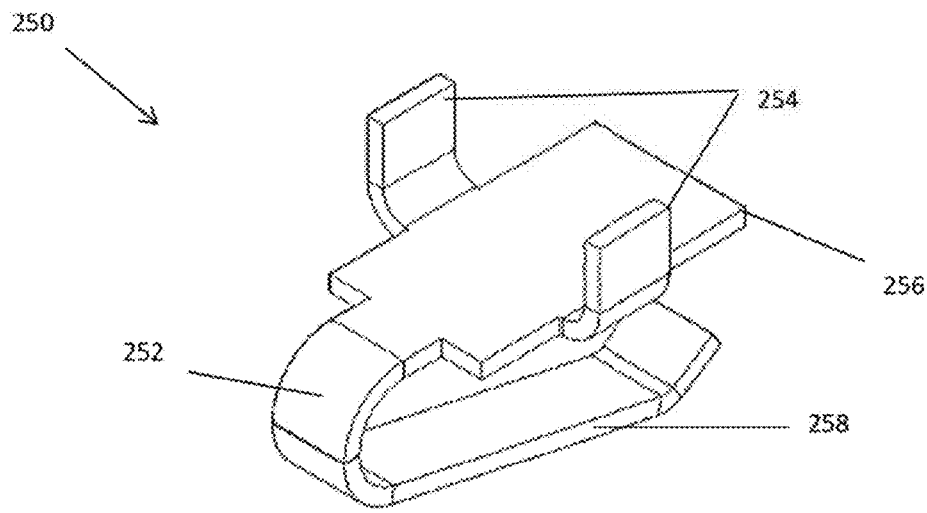
FIG. 3B illustrates a close-up view of the spring pin of FIG. 3A.

FIG. 3B illustrates a close-up view of the spring pin 250. The spring pin 250 includes a springing portion 252 that connects a body portion 256 to a contact arm 258. The contact arm 258 is moved into contact with and supplies power to a blade electrode (not shown) when the blade electrode is fully extended. The body portion 256 includes a pair of connection arm 254 that connect the spring pin 250 to a printed circuit board (not shown).

Figure 4:
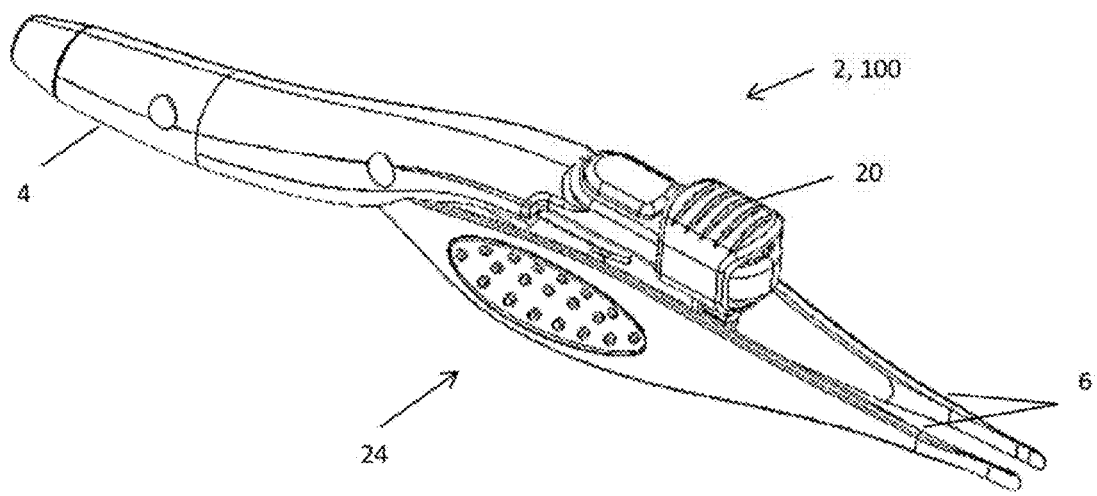
FIG. 4 illustrates a perspective view of an example of an electrosurgical device in a bipolar configuration.

FIG. 4 illustrates another electrosurgical device 2. The electrosurgical device 2 is in the bipolar configuration 100.

The electrosurgical device 2 as illustrated is configured as forceps 4 having a pair of working arms 6. A shuttle 20 as shown is forward in a bipolar position 24 and connected to one working arm 6 so that both of the working arms 6 are free and the working arms 6 may be biased and used in the bipolar configuration 100. When the shuttle is moved to a rearward position the working arms 6 are forced together and immobilized forming a monopolar electrode and/or blade electrode.

Figure 5:
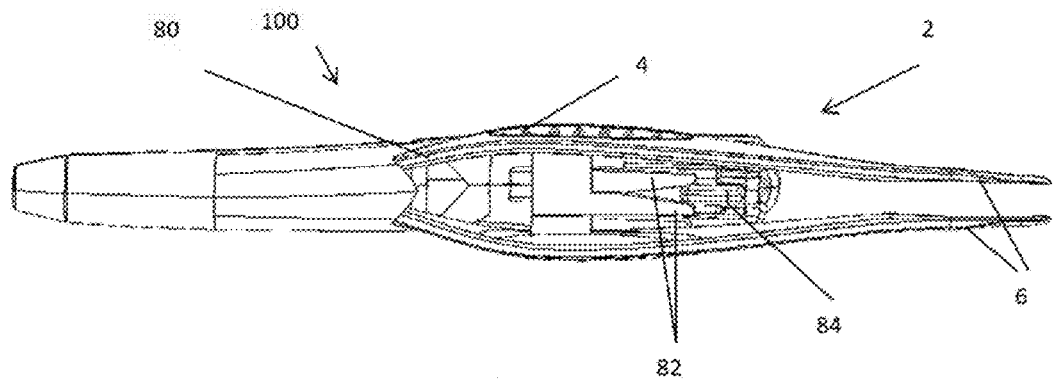
FIG. 5 illustrates a bottom view of the electrosurgical device of FIG. 4 in a bipolar configuration.

FIG. 5 is a bottom view of the electrosurgical device 2 as shown in FIG. 4. As illustrated, the electrosurgical device 2 is in the bipolar configuration 100 with the pair of working arms 6 spread apart forming forceps 4. The working arms 6 each include an immobilization arm 82 extending from the housing 80 and a wedge 84 that separates the immobilization arms 82 so that the working arms 6 are moved into contact and immobilized when transformed from the bipolar configuration 100 to the monopolar configuration 102 (not shown).

Figure 6:
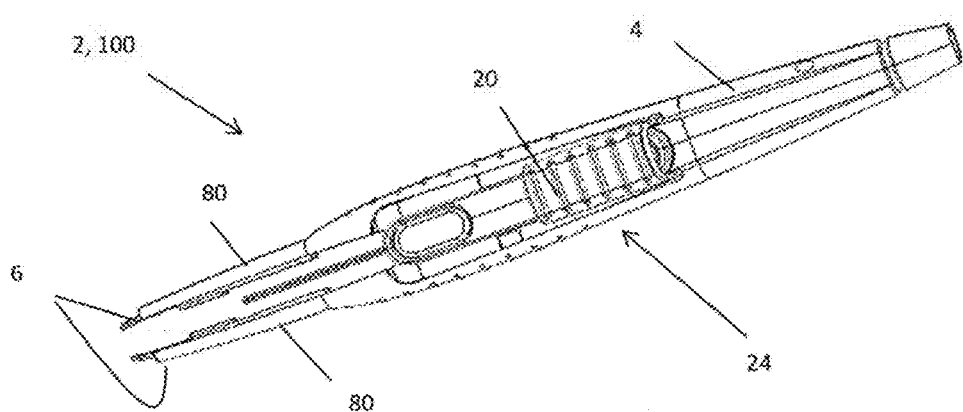
FIG. 6 illustrates a top view of an electrosurgical device.

FIG. 6 illustrates another example of an electrosurgical device 2 of the teachings herein. The electrosurgical device 2 includes a bipolar configuration 100 where the electrosurgical device is forceps 4. The forceps 4 include a housing 60 with a pair of working arms 6 that remain as forceps 4 in the bipolar configuration 100 when the shuttle 20 is in the bipolar position 24. The housing covers the active portions of the working arms 6 along at least a portion of their length so that power is not transferred through incidental contact. While the shuttle 20 remains in the bipolar position 24 (e.g., first position) the bipolar activation button 40 is exposed so that upon pressing the bipolar activation button 40 power extends between the pair of working arms 6.

Figure 7:
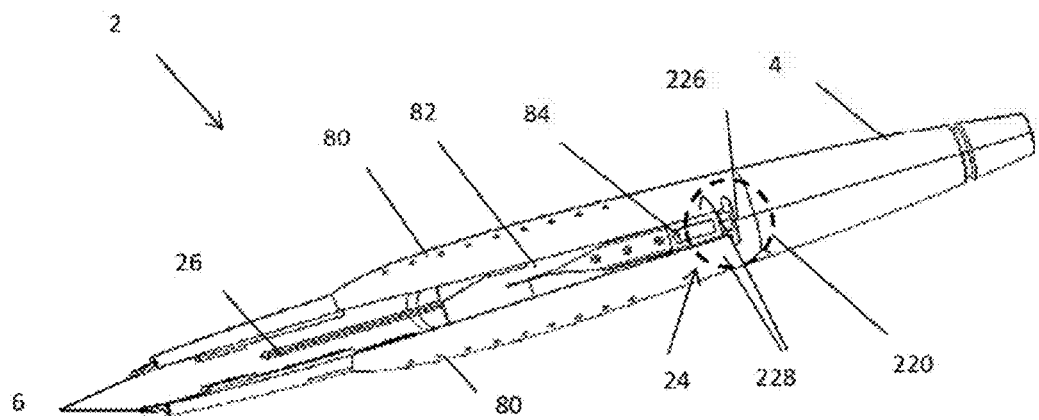
FIG. 7 illustrates configuration bottom view of the electrosurgical device of FIG. 6.

FIG. 7 illustrates a bottom view of the electrosurgical device 2 of FIG. 6 configured as forceps 4. The electrosurgical device 2 includes a housing 80 that covers a majority of the working arms 6. The housing 80 includes a pair of immobilization arms 82 that extend from the housing 80 so that when the wedge 84 advances forward the blade electrode 26 is advanced and the working arms 6 are immobilized. Proximate to the immobilization arms 82 is a hinge 220 in the housing 80. The hinge 220 includes a rigid connection 226 on a proximal side of the hinge 220 and a movable connection 228 on the distal side of the hinge 220.

Figure 8:
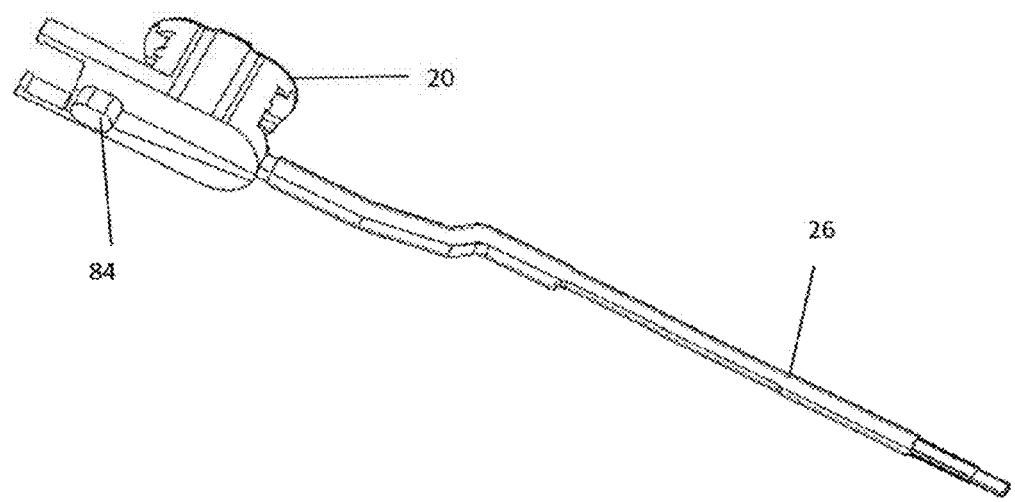
FIG. 8 illustrates a bottom perspective view of a shuttle and blade electrode.

FIG. 8 illustrates bottom perspective view of a shuttle 20 including a wedge 84. The shuttle 20 is connected to a blade electrode 26.

Figure 9:
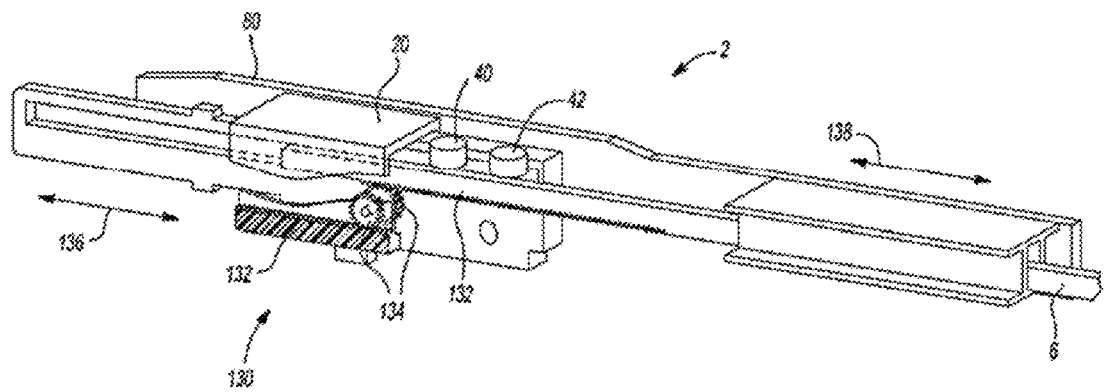
FIG. 9 illustrates an example of a slider assembly of an electrosurgical device.

FIG. 9 illustrates an example of an electrosurgical device 2 with a slider assembly 130. As illustrated, the electrosurgical device 2 has a housing 80 connected to a working arm 6. The working arm 6 is connected to a slider 30 that includes a shuttle 20. The shuttle 20 is connected to a working arm 6 and two pinions 134 that are interfitted between a pair of racks 132. Each pinion 134 contacts a rack 132 and movement of the shuttle 20 in the direction 136 moves the working arm 6 along its axis in direction 138, which is in an opposing direction as the shuttle 20. The pinions 134 have different sizes so that there is a gear reduction and the distance the working arms 6 travel is greater than the distance the shuttle 20 travels during movement. The electrosurgical device 2 includes a bipolar activation button 40 and a monopolar activation button 42.

Figure 10:
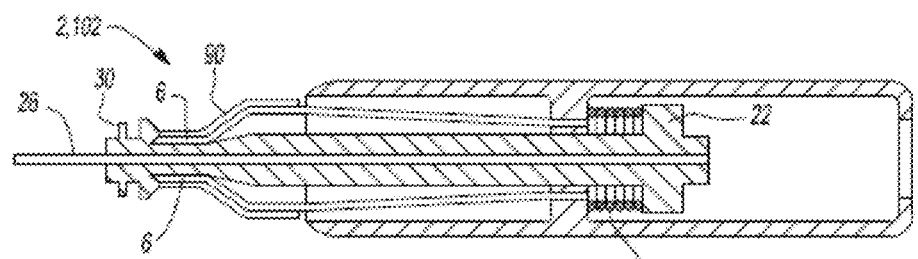
FIG. 10 illustrates another possible configuration of an electrosurgical device in a monopolar configuration.

FIG. 10 illustrates the electrosurgical device 2 in the Monopolar configuration 102. As illustrated, a blade electrode 26 is moved forward to a monopolar position 22 and the working arms 6 are in contact with a monopolar insulator 30 on the blade electrode 26 so that the monopolar insulator 30 immobilizes the working arms 6. As illustrated, the working arms 6 extend into a portion of the monopolar insulator 30 and are immobilized by the monopolar insulator 30, which also substantially prevents current from straying from the working arms 6 when the tips of the working arms 6 are covered by the monopolar insulator 30. The working arms 6 are also covered by an insulator 90 that insulates a length of the working arm 6 and the tips of the working arms 6 are covered by the monopolar insulator 30 so that substantially all of the stray current is insulated and prevented. A bias device 50 is compressed when the blade electrode is moved into the monopolar position 22 so that upon release the bias device 50 assists in retracting the blade electrode 26.

Figure 11:
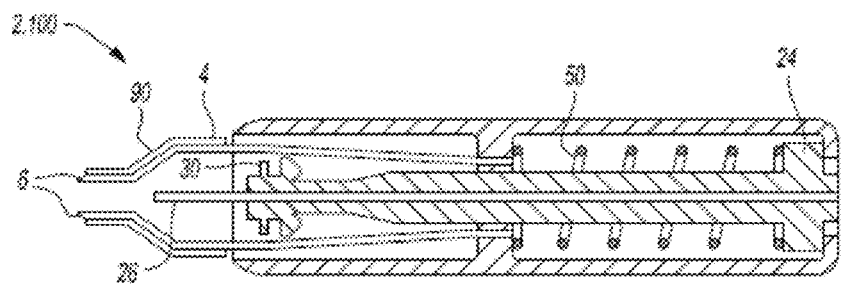
FIG. 11 illustrates an example of the electrosurgical device of FIG. 10 in a monopolar configuration.

FIG. 11 illustrates the electrosurgical device 2 of FIG. 10 in the bipolar configuration 100. As illustrated, the blade electrode 26 is retracted rearward into the bipolar position 24 so that the monopolar insulator 30 is located between the two working arms 6. When the blade electrode 26 is fully retracted the bias device 50 is fully extended. The working arms 6 are separate and can be used as forceps 4 and with bipolar power. The working arms 6 further include an insulator 90 that extends the length of the working arms 6 and a tip of each working arm 6 is exposed.

Figure 12:
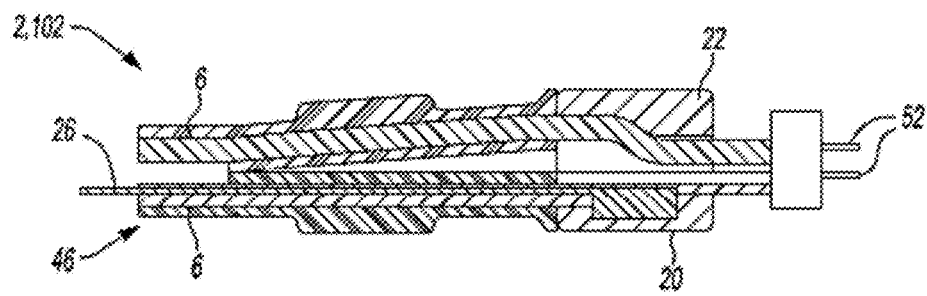
FIG. 12 illustrates en electrosurgical device with electrode extending from a working arm while in the monopolar configuration.

FIG. 12 illustrates another possible configuration of the electrosurgical device 2 in the monopolar configuration 102. As illustrated, the shuttle 20 is moved forward into the monopolar position 22 so that the blade electrode 26 is moved forward through a blade electrode channel 46 in a working arm 6. The electrosurgical device 2 includes a power connectors 52 at an end so that the electrosurgical device 2 is powered during use.

Figure 13:
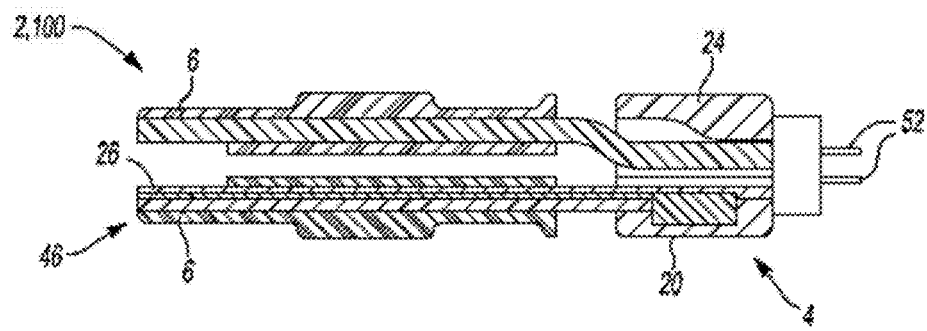
FIG. 13 illustrates the electrosurgical device of FIG. 12 in a bipolar configuration.

FIG. 13 illustrates the electrosurgical device 2 of FIG. 12 in a bipolar configuration 100. The electrosurgical device 2 has the shuttle 20 moved rearward into a bipolar position 24 so that the working arms 6 are separate and can be used as forceps 4. The blade electrode 26 is retracted by the shuttle 20 into the blade electrode channel 46 so that the blade electrode 26 is not exposed. A power connector 52 is at the end of the electrosurgical device 2 for powering the device.

Figure 14:
FIG. 14 illustrates an end view of an example of working arms with a channel for the blade electrode.

FIG. 14 illustrates an end view of the working arms of FIGS. 12 and 13. As illustrated one of the working arms 6 includes a monopolar electrode channel 46 that extends through the working arm 6.

Figure 15:
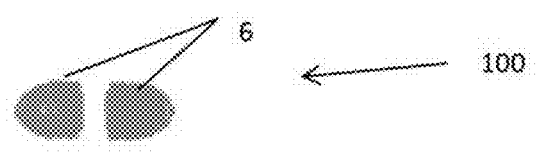
FIG. 15 illustrates an end view of an example of solid working arms.

FIG. 15 illustrates an end view of the working arms of FIGS. 1-7 and 10-1 where the working arms are solid and are free of a channel.

Figure 16:
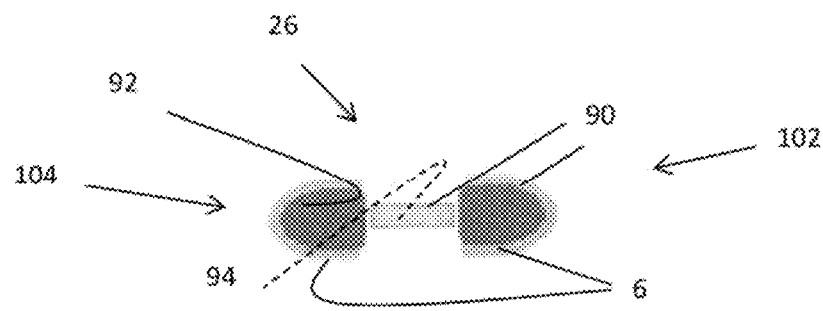
FIG. 16 illustrates the blade electrode rotated for side to side cutting.
Figure 17:
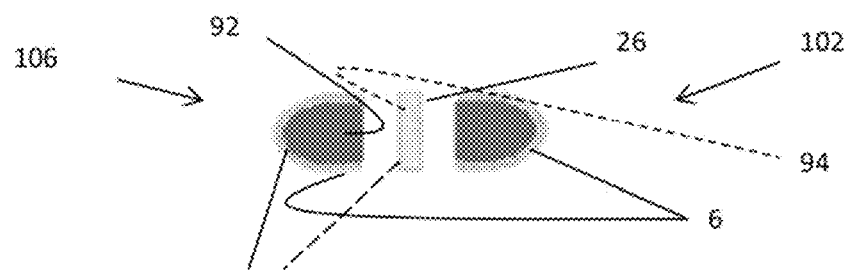
FIG. 17 illustrates the blade electrode rotated for up and down cutting.

FIGS. 16 and 17 illustrate an end view of one possible monopolar configuration 102 where the orientation of the blade electrode 26 is variable between a horizontal monopolar cutting configuration 104 (FIG. 16) and a vertical monopolar cutting configuration 106 (FIG. 17). As illustrated, the working arms 6 are made of two materials. The outer portion of the working arms 6 is made of a material with insulating thermal conductivity 90 and the inner portion is made of a material with high thermal conductivity 92. The outer portion of the blade electrode 26 has insulating conductivity 90 and the center has poor thermal conductivity 94.

Figure 18A:
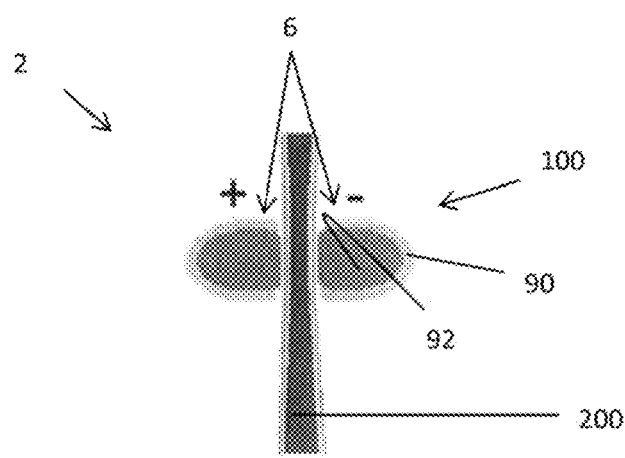
FIG. 18A illustrates a cross-sectional view of working arms gripping tissue.
Figure 18B:
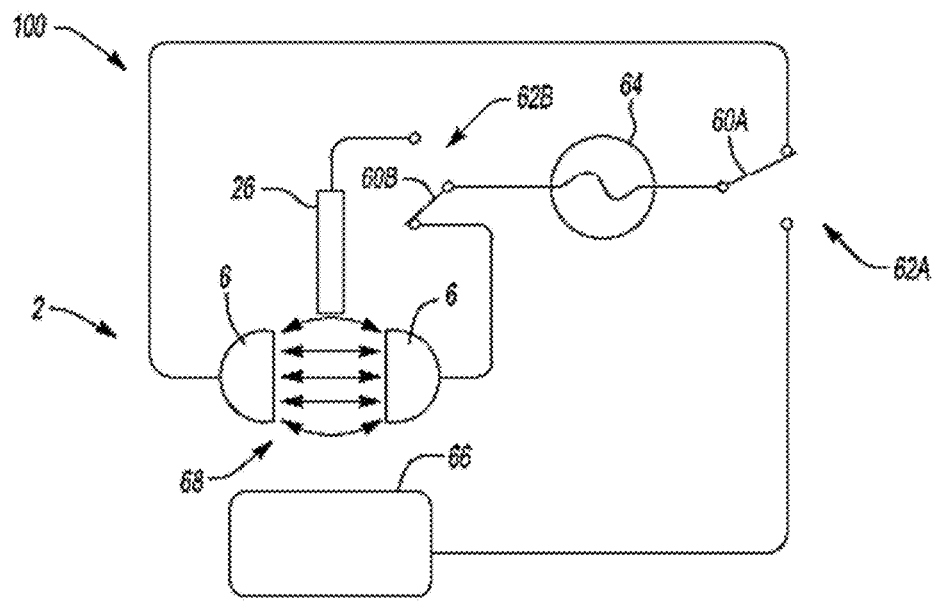
FIG. 18B illustrates the electrosurgical device in the bipolar configuration with power passing between the working arms.

FIGS. 18A and 18B illustrate the electrosurgical device 2 during use in the bipolar configuration 100. FIG. 18A illustrates the pair of working arms 6 having a material portion having insulating thermal conductivity 90 and a material having high thermal conductivity 92. The working arms 6 are in contact with tissue 200 so that power flows through the tissue 200 from one working arm 6 to the other working arm 6.

FIG. 18B is a circuit diagram illustrating one possible bipolar circuit configuration 100 of the electrosurgical device 2. The electrosurgical device 2 is connected to a voltage source 64, and power flows through a switch 60A from the voltage source 64 to one working are 6 and from the voltage source 64 through a switch 60B to the other working arm 6. When the switches 60A and 608 are moved into the bipolar configuration 100 an open circuit 62A and 628 are formed so that the monopolar portion of the circuit including the ground pad 66 is free of power. As illustrated the blade electrode 26 is retracted from between the working arms 6 so that power 68 flows between the working arms 6 and any tissue 200 (not shown) located therebetween.

Figure 19A:
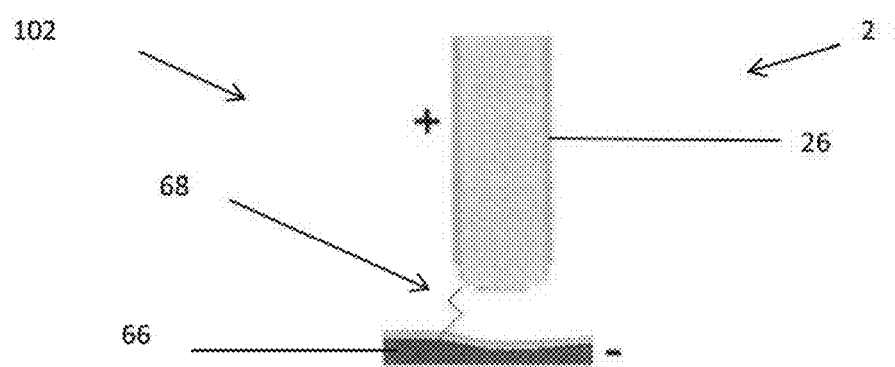
FIG. 19A illustrates a plan view of power passing between a monopolar electrode and tissue.
Figure 19B:
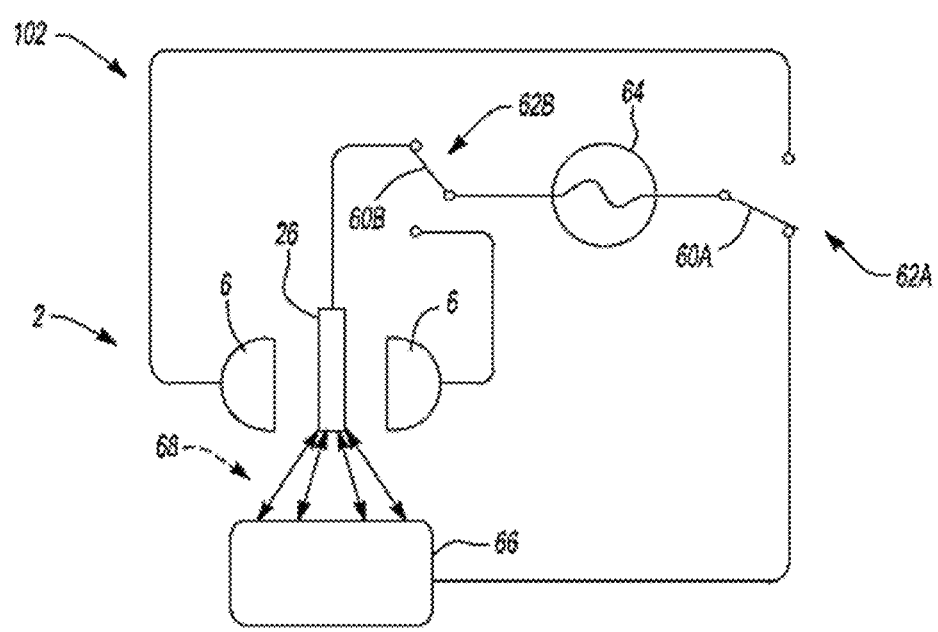
FIG. 19B illustrates the electrosurgical device in the monopolar configuration with power passing between the monopolar electrode and the ground pad.

FIGS. 19A and 19B illustrate the electrosurgical device 2 in a monopolar configuration 102. FIG. 19A illustrates the blade electrode 26 having power flow 68 to a ground pad 66. The power 68 flows through tissue 200 (not shown) from the blade electrode 26 to the ground pad 66.

FIG. 19B illustrates a circuit diagram showing one possible monopolar circuit configuration 102 of the electrosurgical device 2. The electrosurgical device 2 is connected to a voltage source 64, and power flows through a switch 60A from the voltage source 64 to the ground pad 66 and from the voltage source 64 through a switch 60B to the blade electrode 26. When the switches 60A and 608 are moved into the monopolar configuration 102 open circuits 62A and 628 are formed so that the bipolar portion of the circuit and working arms 6 are free of power. When power is applied to the blade electrode 26 power 68 flows from the blade electrode 26 to the ground pad 66.

FIGS. 20A1 through 20A3 illustrate a circuit diagram of the electrosurgical device 2 as tweezers 5 in a bipolar configuration 100. The electrosurgical device 2 is connected to a voltage source 64. FIG. 20A1 includes a switch 60 that moves between a working arm 6 and ado electrode 26 and a switch 60 that moves between a working arm 6 and a ground pad 66. As illustrated, the switch 60 is supplying power to both of the working arms 6 so that power flows 68 between the two working arms 6 and so that the blade electrode 26 and ground pad 66 are open. The two working arms 6 are electrically connected via a connector 70 having a switch 60 therebetween.

FIG. 20A2 includes a centre processing unit 74 that replaces the switching between the voltage source and the blade electrode 26 and the working arms 6. The central processing unit 74 controls the power supplied to the blade electrode 26 and/or the working arms 6 of the tweezers 5 so that as illustrated power 68 flows between the working arms. The central processing unit 74 turned off the ground pad 66 and the blade electrode 26 and turned on the working arms 6. A ground pad 66 extends from the central processing unit 74.

FIG. 20A3 illustrates an electrosurgical device 2 in a hybrid bipolar configuration 100 being configured as tweezers 5 that are gripping tissue 200. The tissue 200 electrically connects the two adjacent working arms 6 so that power flows from the blade electrode 26 through the tissue 200 to the working arms 6. The switch 60 of the connector 70 is closed so that both working arms 6 are powered and electrically connected together and the blade electrode 62 is electrically connected. There is an open 62 between one of the working arms 6 and the power source 64 so that power does not flow directly to one working arm 6 and so that the switch 60 provides power to the blade electrode 26. The switch 60 between the blade electrode 26 and the power source 64 is closed so that power flows between the working arms 6 and the blade electrode 26 through tissue 200.

Figure 20C:
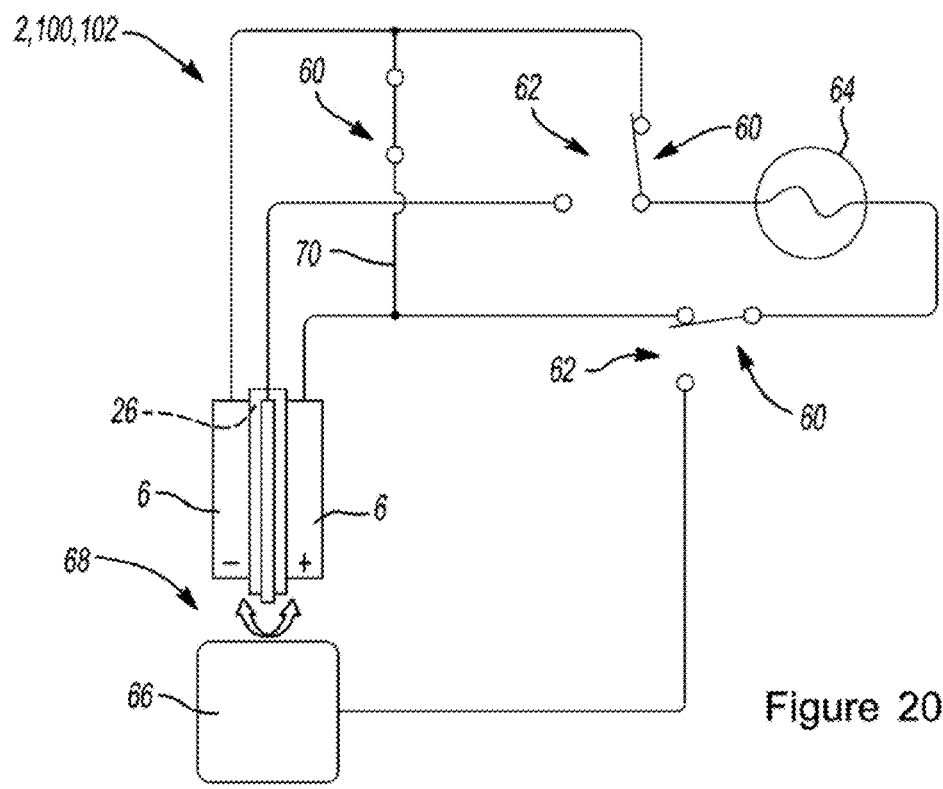
FIG. 20C illustrates a schematic of the electrosurgical device in a monopolar configuration with power extending from the working arms around the blade electrode.
Figure 20D:
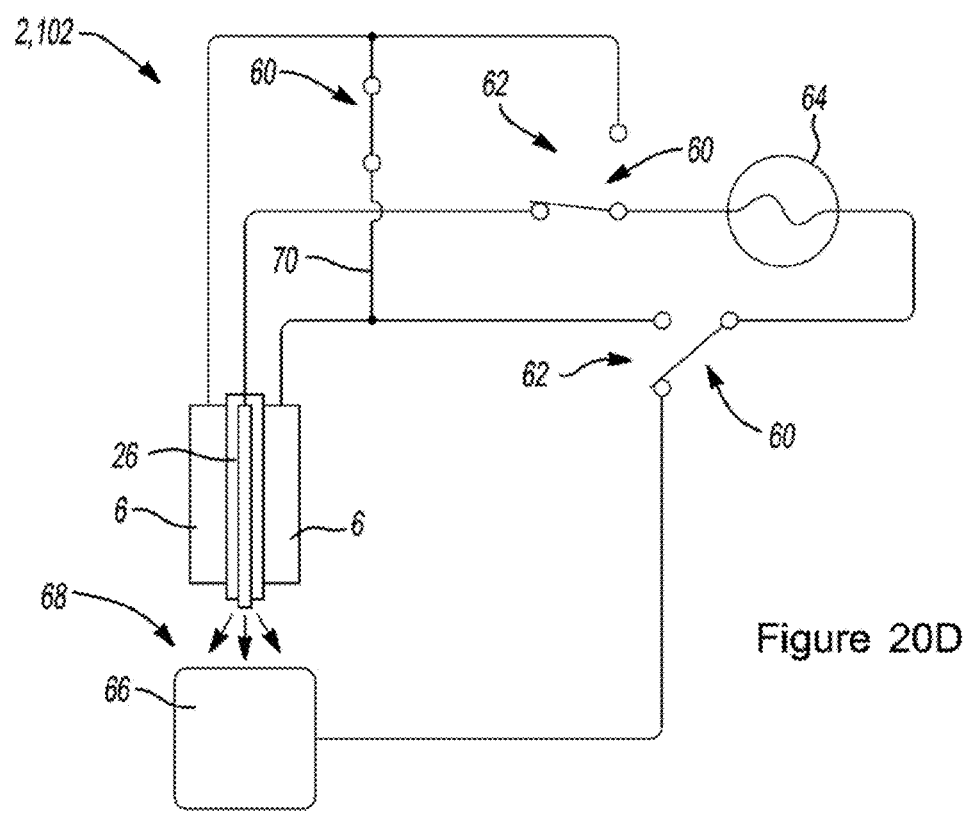
FIG. 20D illustrates a schematic including the electrosurgical device.

FIGS. 20B through 20D illustrate the electrosurgical device 2 in various monopolar configurations 102. As illustrated, the blade electrode 26 being immobilized between the working arms 6. FIG. 20B is a hybrid monopolar configuration 102 for cutting. A switch 60 is closed between the power source 64 and the blade electrode 26 so that power flows 68 from the blade electrode to the two working arms 6. One working arm 6 is connected directly to the power source 64 and the switch 60 proximate to the other working arm is open 62 due to the switch 60 being moved to power the blade electrode 26. The two working arms 6 are electrically connected via a connector 70 that includes a switch 60 so that an electrical connection between the two working arms 6 can be open and closed as the device is switched between a monopolar configuration and a bipolar configuration. The ground pad 66 is open 62 so that power does not flow through the ground pad 66.

FIG. 20C illustrates the electrosurgical device 2 in a hybrid monopolar configuration 102/bipolar configuration 100. As illustrated, both switches 60 are closed so that power is supplied from the power source 64 to both working arms 6 and an open 62 is present between both the blade electrode 26 and the ground pad 66 so that power does not flow to the blade electrode 26 or the ground pad 66. The flow of power 68 is from one working arm 6 to the other working arm 6 around the blade electrode 26. A connector 70 including a switch 60 extends between the working arms 6.

FIG. 20D illustrates the electrosurgical device 2 in a monopolar configuration 102. As illustrated, a switch 60 is located between the power source 64 and the blade electrode 26 so that power flows through the blade electrode 26 and the flow of power 68 flows to the ground pad 66 through another switch 60 so that a complete circuit is formed. When the switch 6 powers the ground pad 66 and the blade electrode 26, the working arms 6 are open 62 so that no power flows through the working arms 6, but the working arms mechanically immobilize the blade electrode 26. The two working arms 6 are electrically connected by a connector 70 that includes a switch 60.

Figure 21:
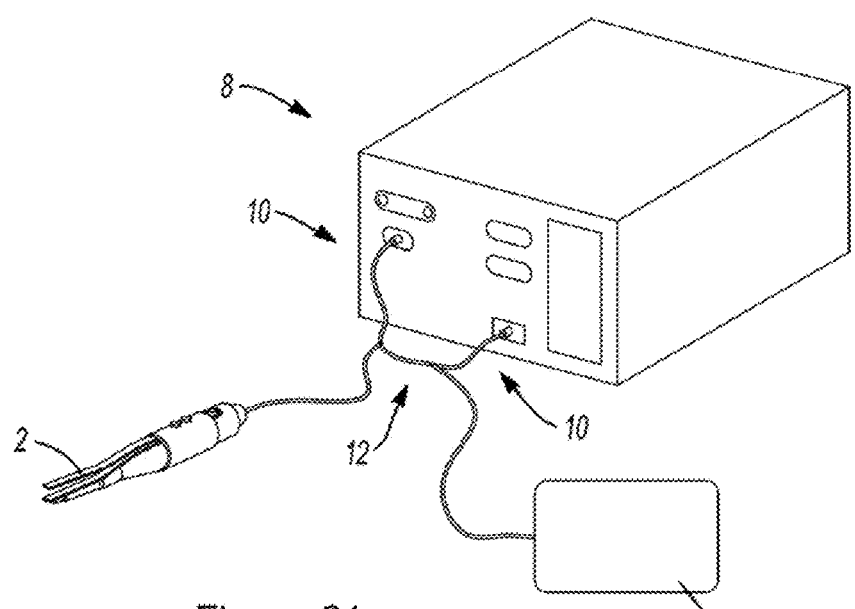
FIG. 21 illustrates one possible configuration of connecting the electrosurgical device of the teachings herein to a generator.

FIG. 21 illustrates the electrosurgical device 2 connected to a generator 8. The generator 8 as illustrated only includes two power connectors 10. The electrosurgical device 2 is connected to the generator 8 via one power connector 10 and the ground pad 66 is connected to the generator 8 via a different power connector 10 and the two power connectors 10 are electrically connected by a jumper 12.

Figure 22A:
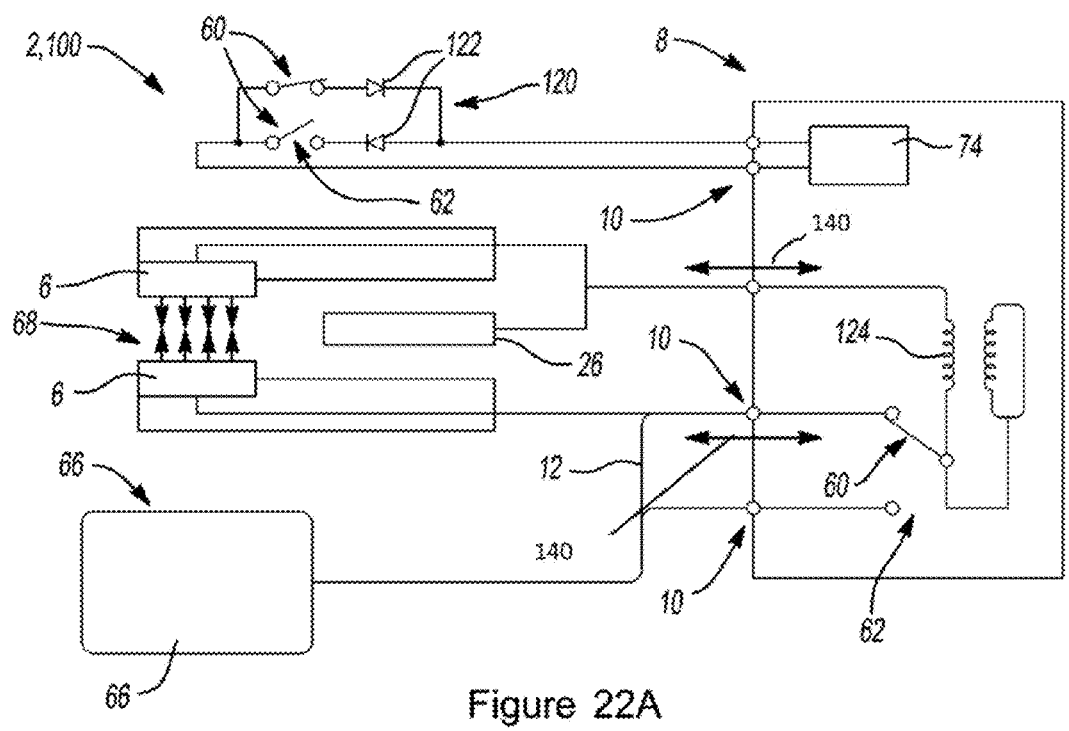
FIG. 22A illustrates an example of control circuit diagram with the working arms in a bipolar configuration.
Figure 22B:
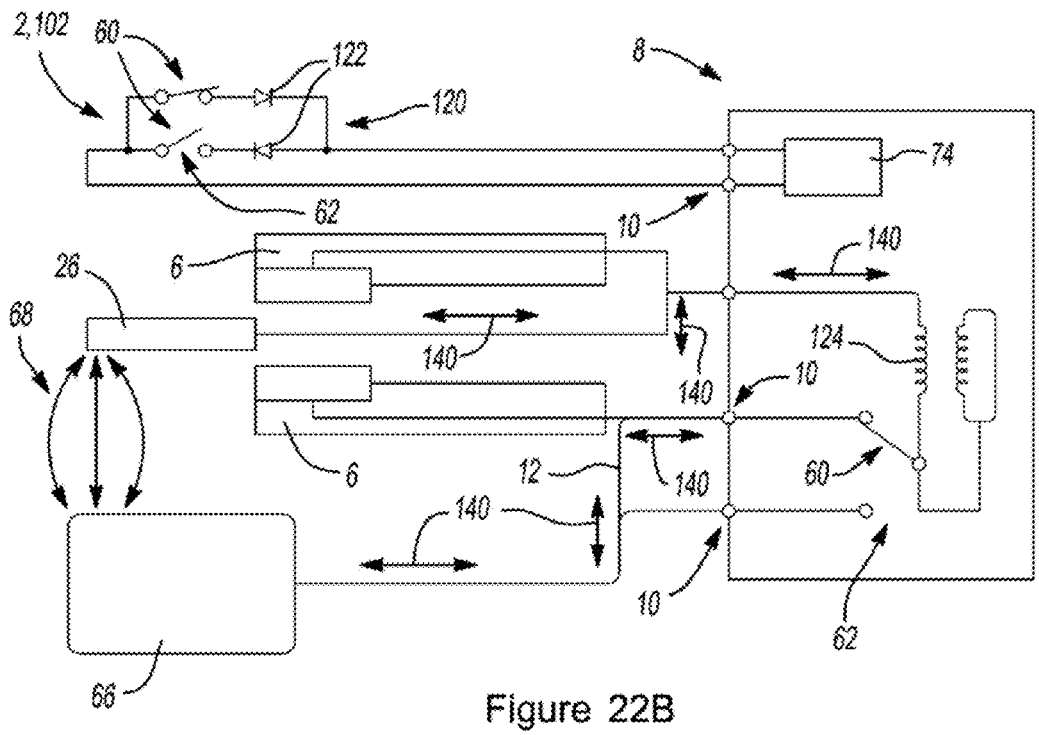
FIG. 22B illustrates an example of a control circuit diagram with the working arms in a monopolar configuration.
Figure 22C:
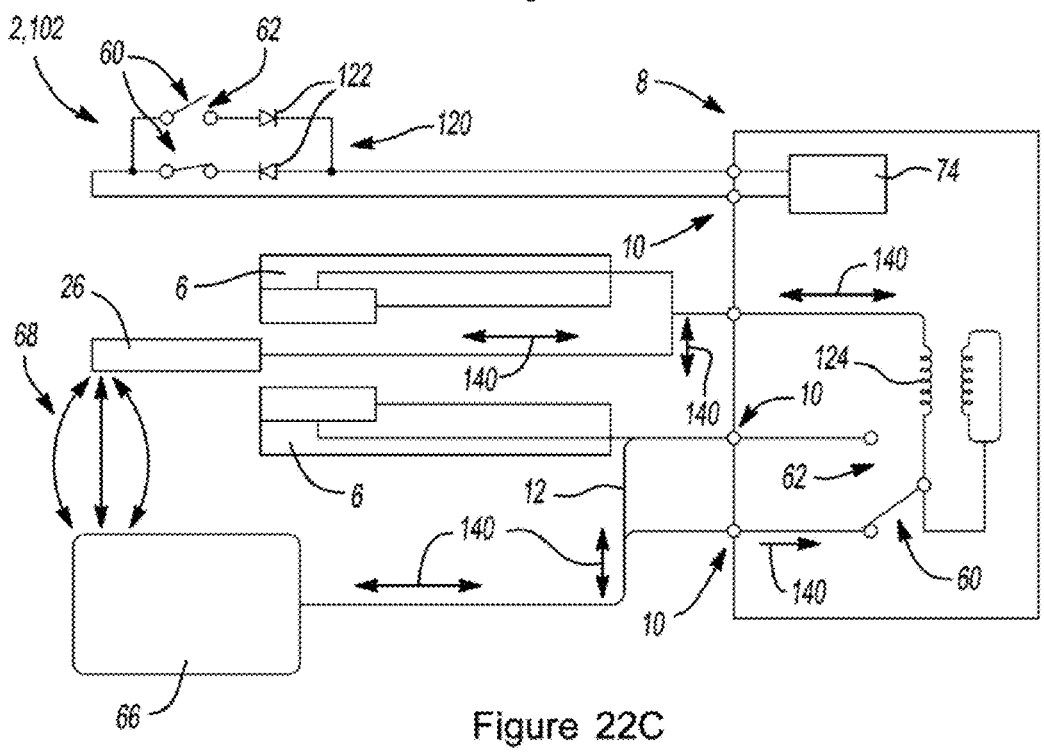
FIG. 22C illustrates example of a control circuit diagram of a monopolar configurations.

FIGS. 22A-22C illustrate various circuit configurations between the generator 8 and the electrosurgical device 2. The generator 8 including central processing unit that is connected to a handpiece 120. A user can change the electrosurgical device 2 between a bipolar configuration 100 (FIG. 22A) and a monopolar configuration 102 (FIGS. 22B and 22C) and a change in configuration to the bipolar configuration 100 will change the switches 60 so that one switch is open 62 and one switch 60 is closed. Each branch of the circuit includes a diode 122 so that when a switch 60 is closed power and/or a control signal pass through the diode 122 to control the electrosurgical device 2. The generator 8 further includes a transformer 124 electrically connected to the ground pad 66, the working arms 6, and the blade electrode 26. A juniper 12 electrically connects the ground pad 66 to one of the working arms 6. The generator 8 includes power connections 10 that extend from the electrical surgical device 2 and are plugged into the generator 8. The generator 8 includes a switch 60 that closes to electrically connect the ground pad 66 and opens 62 to disconnect the ground pad. FIG. 22A illustrates the electrosurgical device 2 in bipolar configuration 100 so that power flows between the transformer 124 and each of the working arms 6 in the direction 140 and the flow of power 68 is between to working arms 6. FIG. 22B illustrates electrosurgical device in the monopolar coagulation configuration. As illustrated, power flows from the blade electrode 26 to the ground pad 66 and power flows in the direction 140 between the transformer 124 and the blade electrode 26 and the ground pad 66. FIG. 22C illustrates the electrosurgical device 2 in monopolar cut configuration so that power flows 68 from the mono polar electrode 26 to the ground pad 66. The power then flows in the direction 140 through the closed switch 60 between the transformer 124 and the blade electrode 26 and ground pad 66.

Figure 23A:
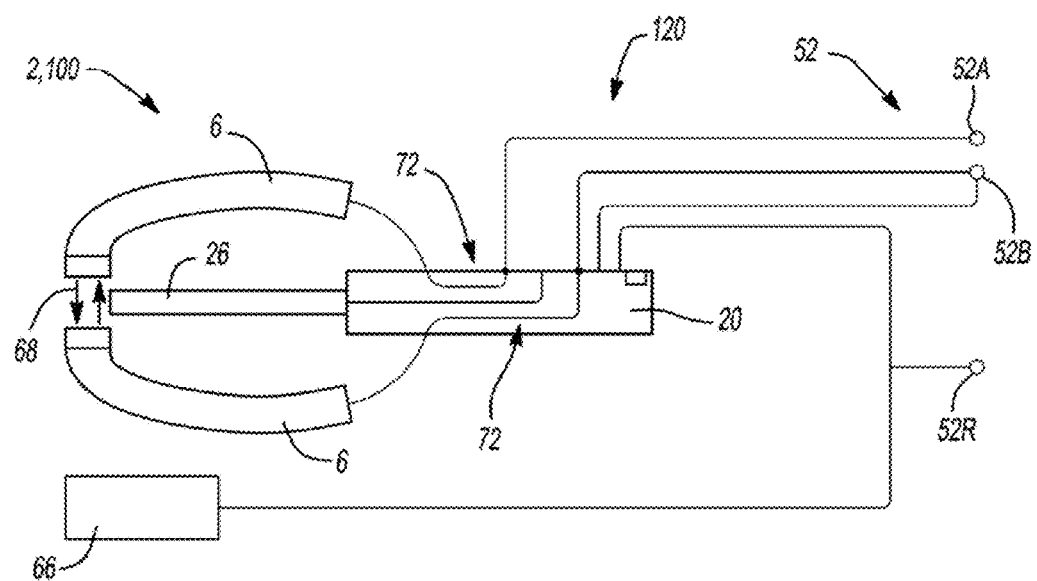
FIG. 23A illustrates a circuit diagram of one possible bipolar configuration.
Figure 23B:
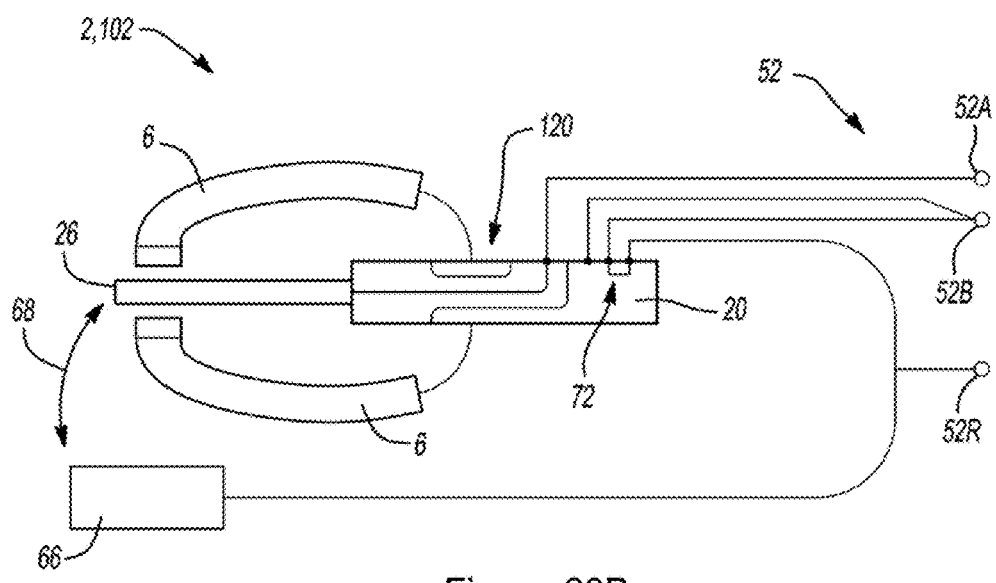
FIG. 23B illustrate a circuit diagram of one possible monopolar configuration.

FIGS. 23A and 23B illustrate the electrosurgical device 2 having three power connectors 52 extending therefrom for connecting to a generator 8 (not shown). FIG. 23A illustrates the blade electrode 26 and shuttle 20 in the retracted position so that the electrosurgical device 2 is in the bipolar configuration 100. The handpiece 120 includes a pair of working arms 6 with a blade electrode 26 therebetween. The handpiece 26 also includes a shuttle 20 with electrical connectors 72 that connect the working arms 6 to the power connectors 52. As illustrated, the positive pin 52A connects to a first end of an electrical connector 72 and the second end connects to a first working arm, and a negative pin 52B connects to a first end of a second electrical connector 72 and the second end connects to a second working arm 6 so that the working arms are powered and power 68 extends between the working arms 6. The negative pin 52B includes two wires extending therefrom so that the negative pin 52B is not electrically isolated. One wire from the negative pin 52B is connected to a working arm 6 through the electrical connector 72 in the bipolar configuration as shown, and the other wire from the negative pin 52B connects to the ground pad 66 when in the monopolar configuration as is shown in FIG. 23B. The ground pad 66 is connected to a return pin 52R and the return pin 52R is disconnected so that power does not flow through the ground pad 66.

FIG. 23B illustrates the shuttle 20 of the handpiece 120 moved forward so that the blade electrode 26 is in the monopolar configuration 102. The handpiece 120 includes working arms 6 and a blade electrode 26 in a monopolar configuration 102. The working arms 6 are disconnected so that the working arms 6 are not powered. Power 68 extends from the blade electrode 26 to ground pad 66. The ground pad 66 is electrically connected to a return pin 52R and a negative pin 52B. A wire extends from the return pin 52R through an electrical connector 72 in the shuttle 20 of the handpiece 120 and connects to a negative pin 52B. The positive pin 52A is connected to a second electrical connector 72 in the handpiece 120, but the second electrical connector 72 is free of a connection on a second side.

Figure 23C:
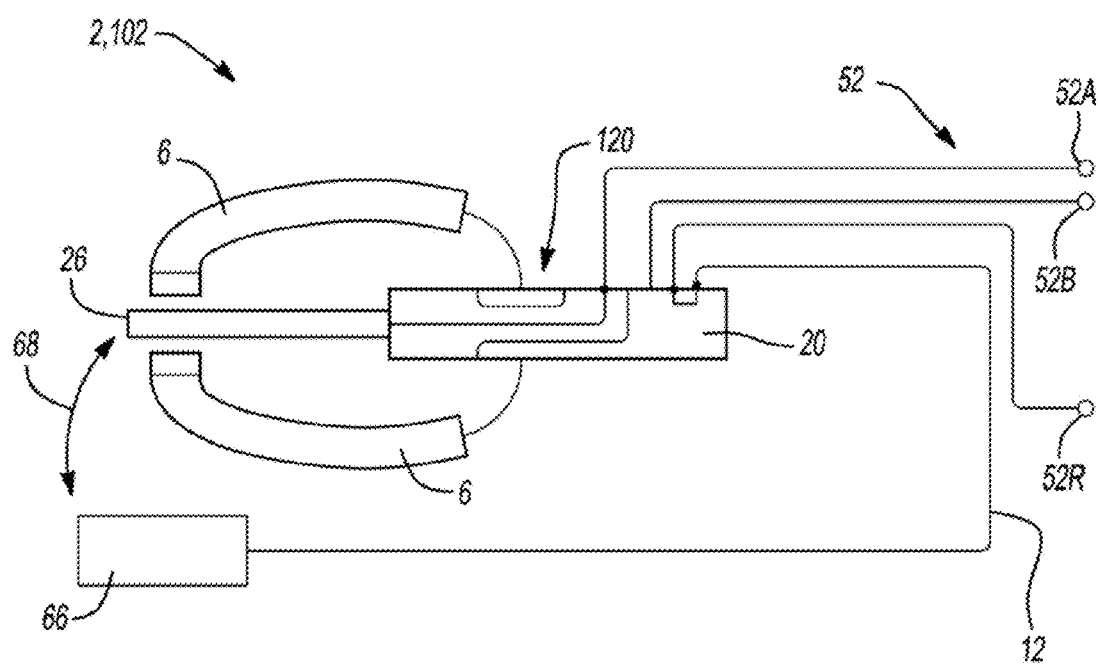
FIG. 23C illustrates an example of another circuit diagram with the electrosurgical device in the monopolar configuration.

FIG. 23C illustrates an electrosurgical device 2 in a monopolar configuration 102. The electrosurgical device 2 includes a handpiece 120 with a pair of working arms 6 and a blade electrode 26 extending therebetween. Power 68 extends from the blade electrode 26 to a ground pad 66. The ground pad 66 is electrically connected to a return pin 52R through a shuttle 20. The shuttle 20 includes electrical connectors 72 that extend through the shuttle 20 and electrically connect the ground pad 66 to a return pin 52R. A positive pin 52A connects to a blade electrode 26 through a second electrical connector 72 that extends through the shuttle 20 in the handpiece 120. The negative pin 52B and the return pin 52R are electrically isolated when compared to FIGS. 23A and 23B.

Figure 24A:
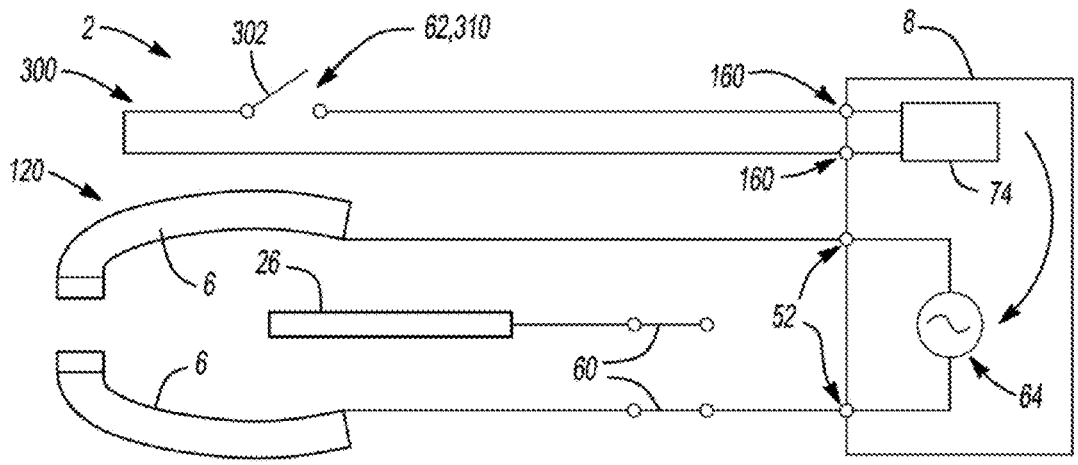
FIG. 24A illustrates a circuit diagram of the electrosurgical device in the off position and the blade electrode including a switch.
Figure 24B:
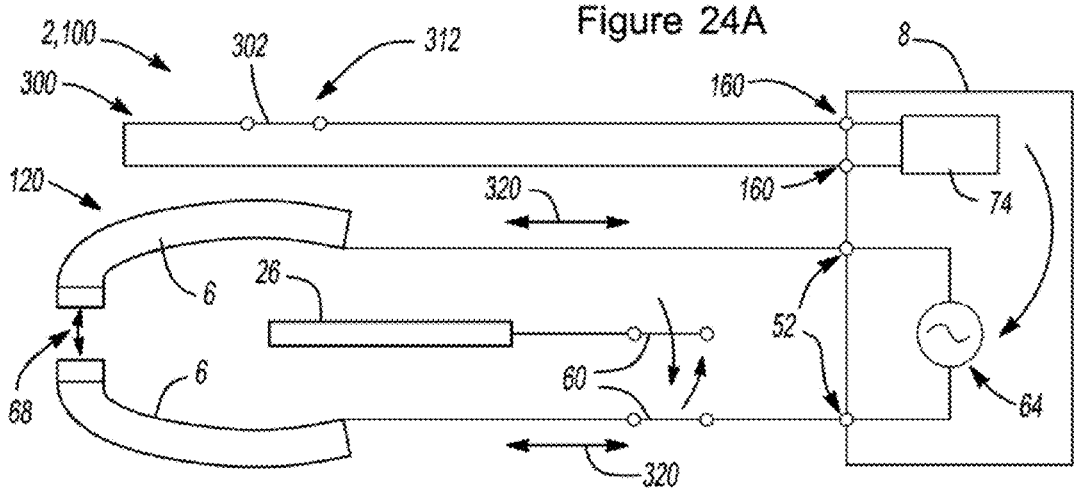
FIG. 24B illustrates a circuit diagram of the electrosurgical device in the bipolar configuration with the blade electrode including a switch.
Figure 24C:
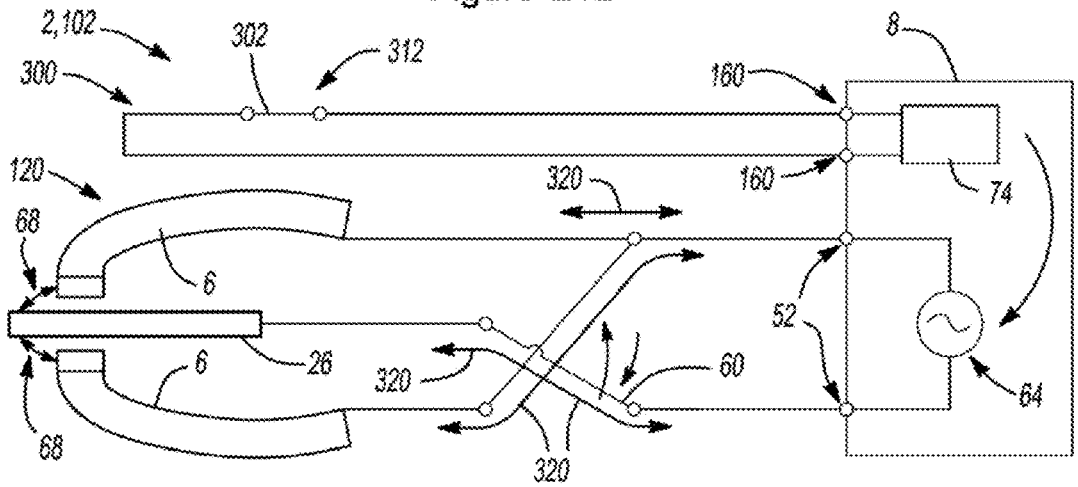
FIG. 24C illustrates a circuit diagram of the electrosurgical device in the monopolar configuration with the blade electrode including a switch.

FIGS. 24A-24C illustrate the electrosurgical device 2 having two power connectors 52 extending from the handpiece 120 for connecting the electrosurgical device to a generator 8. The electrosurgical device 2 also includes an activation circuit 300 for powering the handpiece 120. The electrosurgical device 2 as illustrated is free of a ground pad. FIG. 24A illustrates the electrosurgical device 2 in the bipolar configuration 100 where both power connectors 52 are connected to the handpiece 120. The activation circuit 300 includes an activation button 302 in a first switch state 310 so that the switch is open 62 and a signal does not flow from the activation circuit 300 through the ports 160 and to the generator 8 so that the voltage source 64 does not send power to the electrosurgical device through the power connectors 52. The blade electrode 26 includes a switch 60 that is open so that the blade electrode 26 is electrically disconnected. The switch 60 connected to the working arm is closed so that the working arm is electrically connected.

FIG. 24B illustrates the electrosurgical device 2 in the bipolar configuration 100 and power 68 extend between the working arms 6. The activation button 302 on the activation circuit 300 is in the second switch state 312 so that a signal is sent to the internal switch and/or central processing unit (CPU) 74 in the generator 8, through the ports 160. The internal switch and/or CPU 74 triggers the voltage source 64 to power the handpiece 120. Power flows through the power connectors 52 in the direction 320 through the switch 60 and powers the working arms 6 so that power 68 flows therebetween. The switch 60 of the blade electrode 26 is disconnected so that the blade electrode 26 is not powered.

Figure 25A:
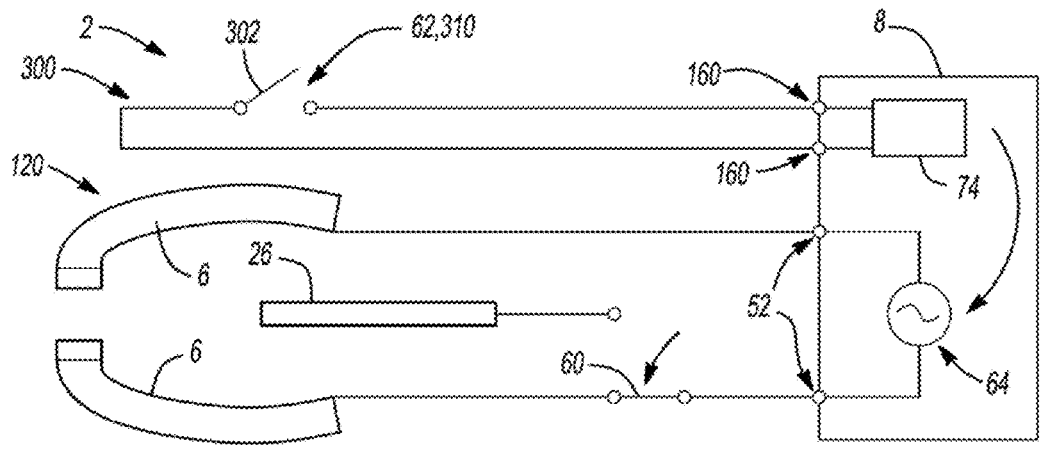
FIG. 25A illustrates a circuit diagram of the electrosurgical device in the off position where the blade electrode is free of a switch.

FIG. 24C illustrates the electrosurgical device 2 in the bipolar configuration 102 where both power connectors 52 connect to the handpiece 120 to the generator 8 and the activation circuit 300 is connected to the generator 8 by the ports 160. The activation button 42 is in the second switch state 312 so that a signal is sent to the internal switch and/or CPU 74, which triggers power to extend in the directions 320 from the voltage source 64. The blade electrode 26 is in the extended position and the switch 60 of the blade electrode 26 is connected to a working arm so that the blade electrode 26 is powered. The other switch 60 extends from one working arm to the other working arm so that both working arms are electrically connected and power can travel between the blade electrode 26 and the working arms 6. The direction arrows show the movement of the switches 60 between the bipolar configuration of FIG. 24B to the monopolar configuration of FIG. 24C FIGS. 25A-25C illustrate various electrical configurations within the handpiece 120 of the electrosurgical device 2. The handpiece 120 includes a pair of working arms 6 and a blade electrode 26 that extends between the working arms 6, and the handpiece 120 is connected to a generator 8. The handpiece 120 is controlled by an activation circuit 300 that is connected to the generator 8. The electrosurgical device 2 as illustrated is free of a ground pad and a switch connected to the blade electrode. FIG. 25A illustrates the electrosurgical device 2 off. The activation button 302 of the activation circuit 300 is in a first switch state 310 and is open 62 so that a signal does not flow to the generator 8 through the ports and into communication with the internal switch and/or CPU 74. The internal switch and/or CPU 74 controls the flower of power from the voltage source 64 through the power connectors 52 and into the working arms 6 and/or blade electrode 26. As illustrated, the switch 60 is closed so that when power is applied both working arms 6 will be powered.

Figure 25B:
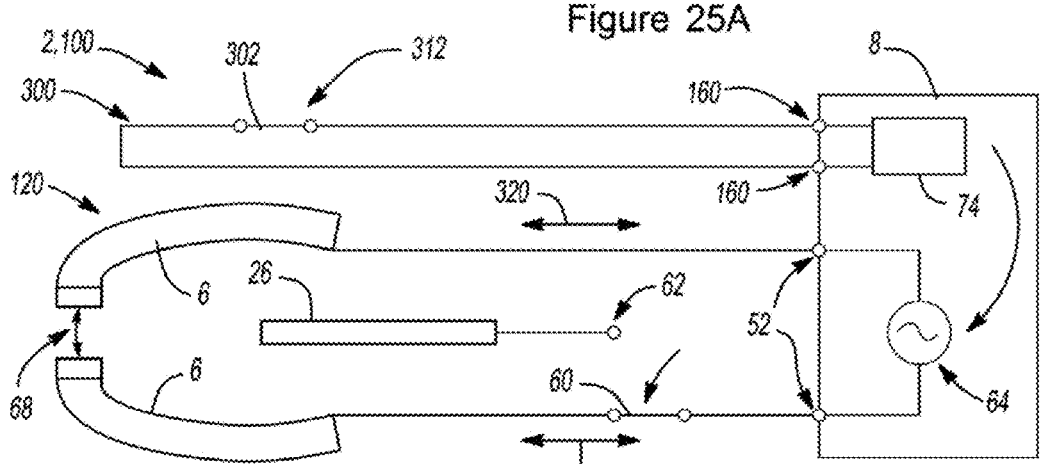
FIG. 25B illustrates a circuit diagram of the electrosurgical device in the bipolar configuration with the blade electrode free of a switch.

FIG. 25B illustrates the electrosurgical device 2 of FIG. 25A powered when the activation button 302 is moved into the second switch state 312. When the activation button 302 is closed a signal is sent from the activation circuit 300 to the internal switching and/or CPU 74 which triggers power to be sent from the voltage source 64 through the power connectors 52 and to the working arms 6 in the direction 320. The power flows in the direction 68 between the pair of working arms 6.

Figure 25C:
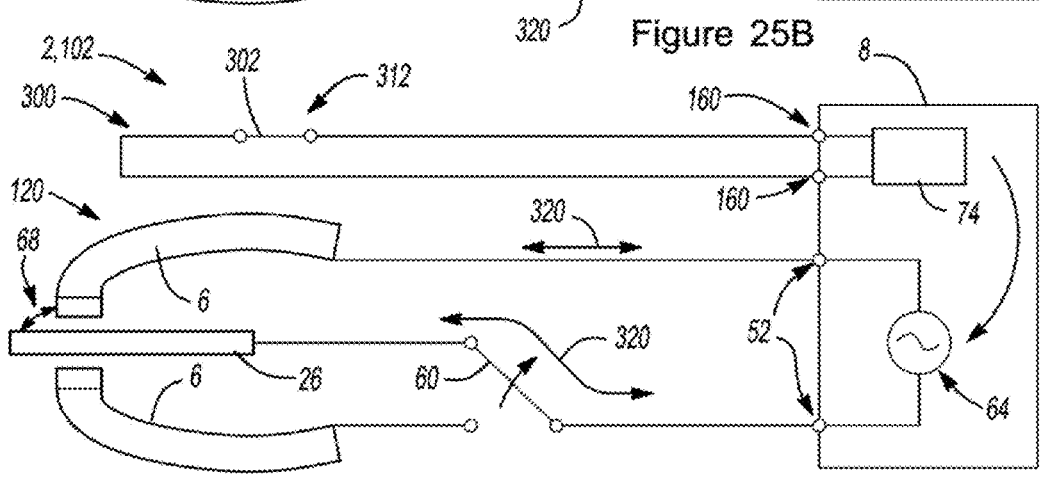
FIG. 25C illustrates a circuit diagram of the electrosurgical device in a monopolar configuration where the blade electrode is free of a switch.

FIG. 25C illustrates switch 60 being moved from the second working arm 6 to the blade electrode 26 as is indicated by the arrow so that the second working arm 6 is turned off and remains open 62 and the blade electrode 26 is powered. Power flows from the generator 8 in the direction 320 so that the blade electrode is powered and power 68 flows from the blade electrode 26 to the working arm 6.

FIG. 26A through 26C illustrate reconfiguration of the electrosurgical device 2. The electrosurgical device includes a ground pad 66, and handpiece 120, and an activation circuit 300. FIG. 26A illustrates the electrosurgical device 2 turned off. As illustrated the activation button 302 on the activation circuit 300 is in a first switch state 310 and is open 62 so that a signal is not sent to the generator 8 powering the handpiece 120. Further the blade electrode 26 and the ground pad 66 are open because the switches 60 are closed in the direction indicated by the arrow so that the working arms are connected by the closed switches 6.

FIG. 26B illustrates the electrosurgical device 2 of FIG. 26A the bipolar configuration 100 with the activation button 302 of the activation circuit 300 moved to a second switch state 312. The second switch state 312 completes the circuit so that a signal passes from the activation circuit 300 through the ports 160 in the generator 8 and into communication with the internal switching and/or CPU 74. The internal switching and/or CPU 74 triggers power to travel from the voltage source 64 into the handpiece 120 through the power connectors 52 in the direction 320 through the closed switches 60 so that both working arms 6 are powered and power 68 flows between the working arms 6.

FIG. 26C illustrates the blade electrode 26 in an extended position between the pair of working arms 6 so that a monopolar configuration 102 is formed. When the blade electrode 26 is extended the switches 60 are moved from the first working arm 6 and the second working arm 6 to the blade electrode 26 and ground pad 66 respectively so that the blade electrode 26 is powered when the activation button 302 is in the second switch state 312 as is illustrated. Power travels in the direction 320 from the power connectors, through the switched 60, and then to the blade electrode 26 and ground pad 66 respectively. Power 68 passes between the blade electrode 26 and the ground pad 66

Figure 27A:
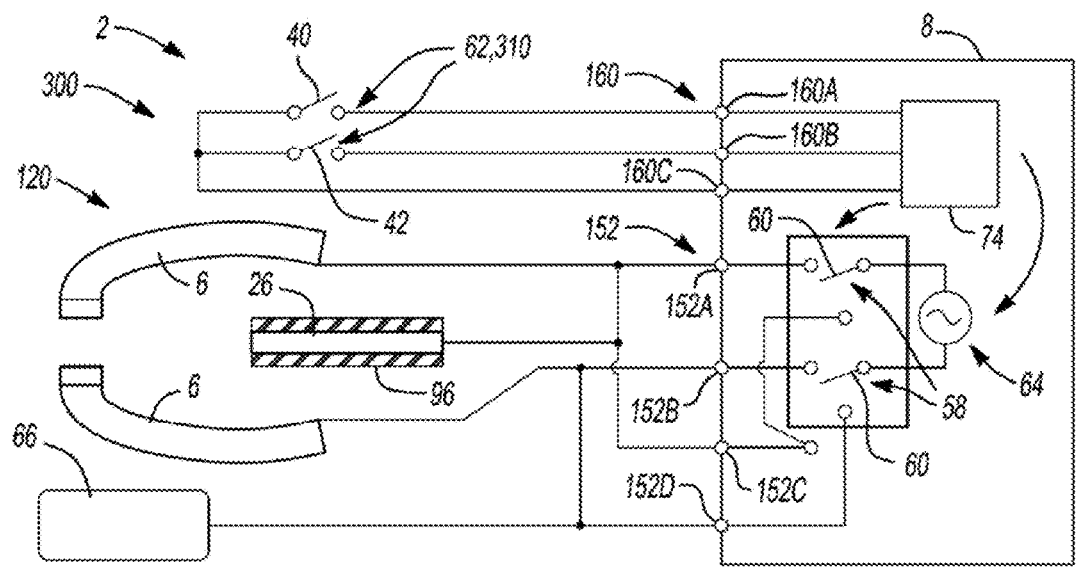
FIG. 27A illustrates an example of an electrosurgical device including an activation circuit with the activation circuit being in the off position.
Figure 27B:
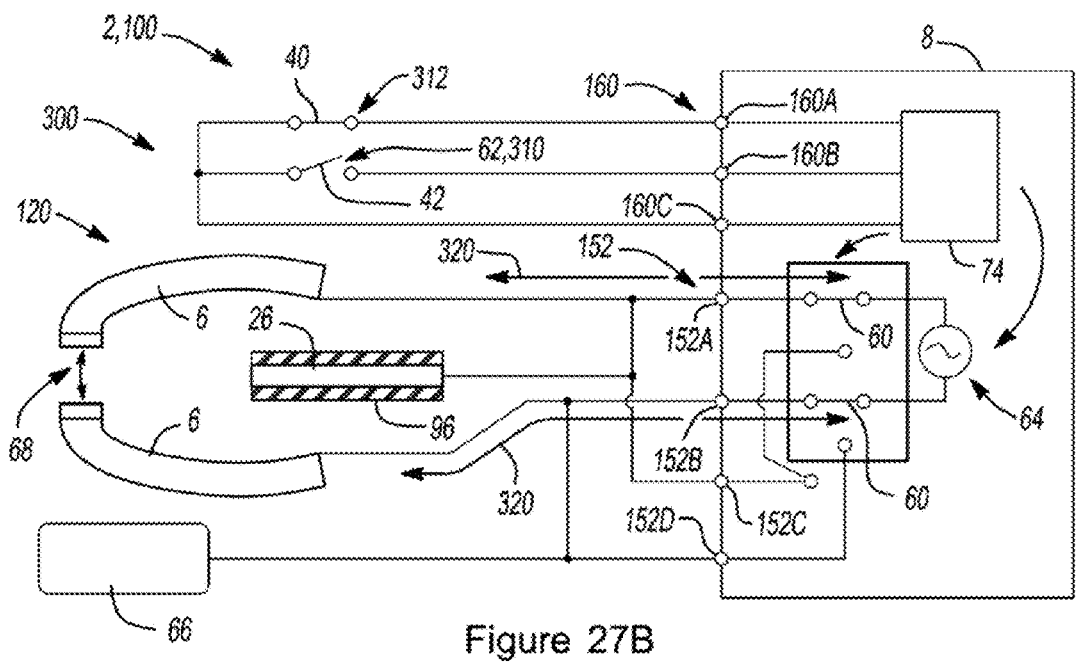
FIG. 27B illustrates an example of the electrosurgical device in the bipolar configuration.
Figure 27C:
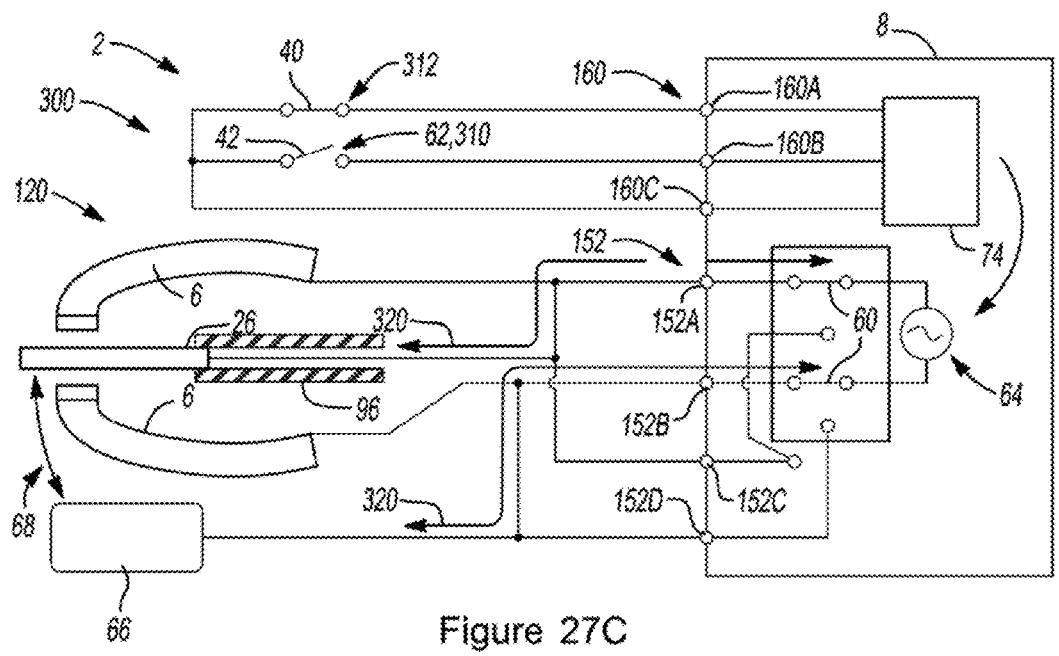
FIG. 27C illustrates an example of the electrosurgical device in the monopolar configuration and a second activation button closed.
Figure 27D:
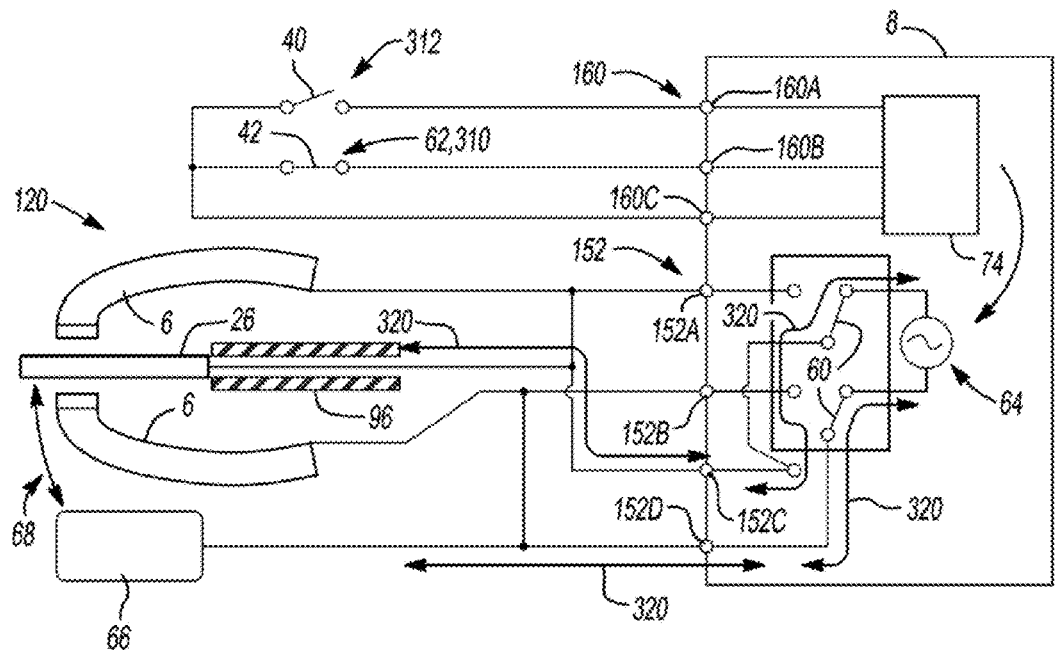
FIG. 27D illustrates an example of the electrosurgical device in the monopolar configuration and a first activation button closed.

FIGS. 27E through 27D illustrate an electrosurgical device 2 with an activation circuit 300 connected to a generator by a plurality of ports 160 and a handpiece 120 connected to the generator 8 by a plurality of pins 152. The activation circuit 300 includes activation buttons 40, 42 that when depressed power the handpiece 120. FIG. 27A illustrates the activation circuit 300 with both the bipolar activation button 40 and the monopolar activation button 42 in the first switch state 310 and open 62 so that the electrosurgical device 2 is off. The activation circuit 300 has three electrical paths wires) that connect with the generator 8 via an upper port 160A, a middle port 160B, and a lower port 160C. The ports 160 connect the activation circuit 300 with internal switching and/or a CPU 74 that when receives a signal communicates with the power source 64 powering the handpiece 120. The power source 64 directs power through a series of switches 60, which as illustrated are in a neutral position 58. The switches 60 direct the power through the plurality of pins 160. The plurality of pins are a bipolar positive pin 152A, a bipolar negative pin 152B, a monopolar active pin 152C, and a monopolar return pin 152D that power one or more parts of the headpiece 120 when the handpiece 120 is switched between a monopolar configuration and a bipolar configuration. As illustrated the blade electrode 26 is retracted and nested within an insulator housing 96.

FIG. 27B illustrates the electrosurgical device 2 of FIG. 27A in the bipolar configuration 100 with the blade electrode 26 retracted and located within the insulator housing 96 so that stray currants are prevented from transferring to and/or from the blade electrode 26, and the bipolar activation button 40 in the second switch state 312 so that a signal is generated and a circuit is completed with the upper port 160A and the lower port 160E so that a signal passes therethrough into the generator 8 and ultimately to the internal switching and/or CPU 74. The monopolar activation button 42 is in the first switch state 310 and is open 62. The internal switching and/or CPU 74 activates the voltage source 64 so that power extends through the upper switch 60 and through the bipolar positive pin 152A so that the first working arm 6 is powered by current traveling in the direction 320. Power extends through the bottom switch 60 and out the bipolar negative pin 152B so that the second working arm receives power along the direction 320. The power 68 then extends between the pair of working arms 6. The ground pad 66 and the blade electrode 26 are electrically disconnected as illustrated.

FIG. 27C illustrates the blade electrode 26 extended out from the insulator housing 96 and between the working arms 6 and power 68 extending from the blade electrode 26 to the ground pad 66. The activation circuit 300 includes the bipolar activation button 40 in the second switch state 312 so that a compete circuit is formed with the upper port 160A and the tower port 160C so that a signal is transmitted to the internal switching and/or CPU 74 of the generator 8. The monopolar activation button 42 is in the first switch state 310 and is open so that a signal is not transmitted from the monopolar activation button 42. The internal switching and/or CPU 74 communicates with the voltage source 64 so that power is directed along the paths 320 to the blade electrode 26 and ground pad 66 respectively. The switches 60 are configured so that power extends from the voltage source 64 through the bipolar positive pin 152A and the bipolar negative pin 152B so that a the power 68 between the blade electrode 26 and the ground pad 66 is a first therapy current.

Figure 28A:
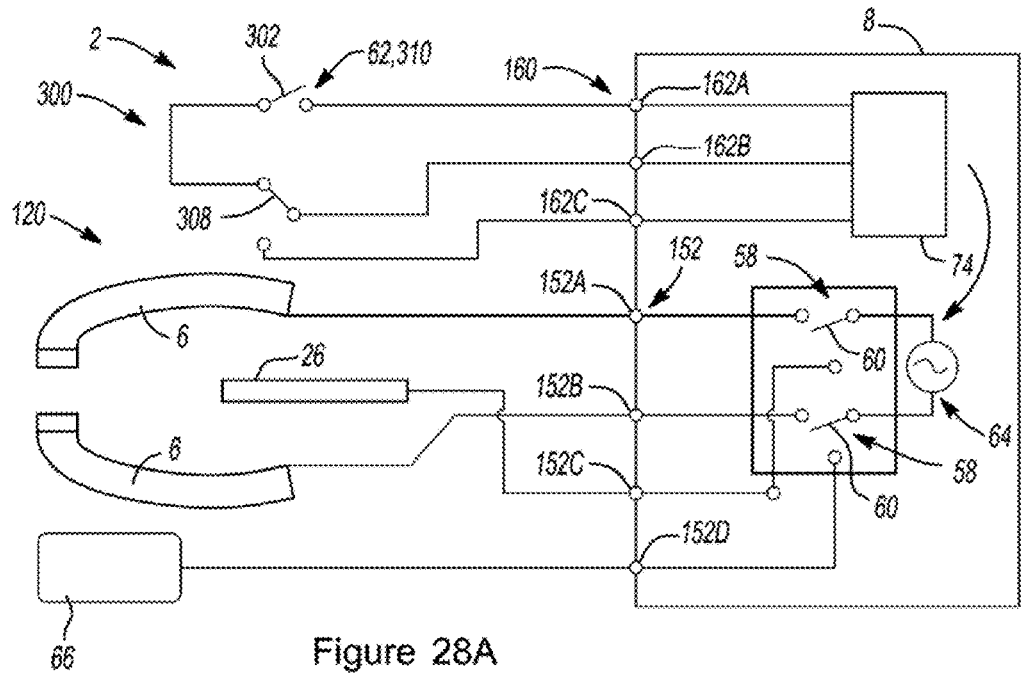
FIG. 28A illustrates an electrosurgical device including an activation including an activation button and a selector with the electrosurgical device being off.
Figure 28B:
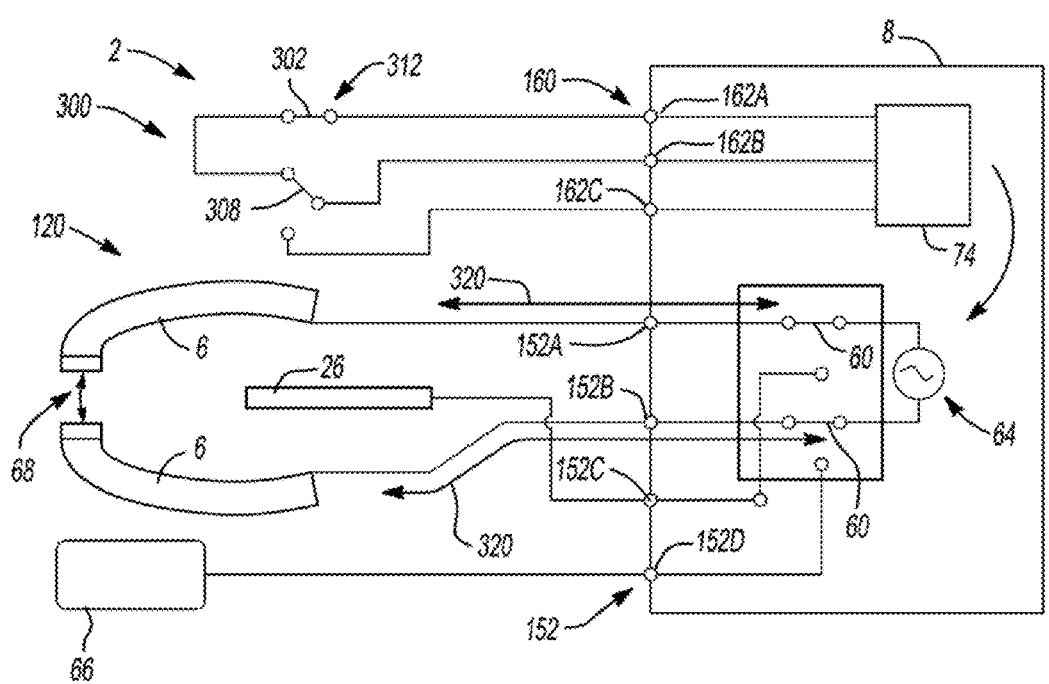
FIG. 28B illustrates the electrosurgical device of FIG. 28A in the bipolar configuration.
Figure 28C:
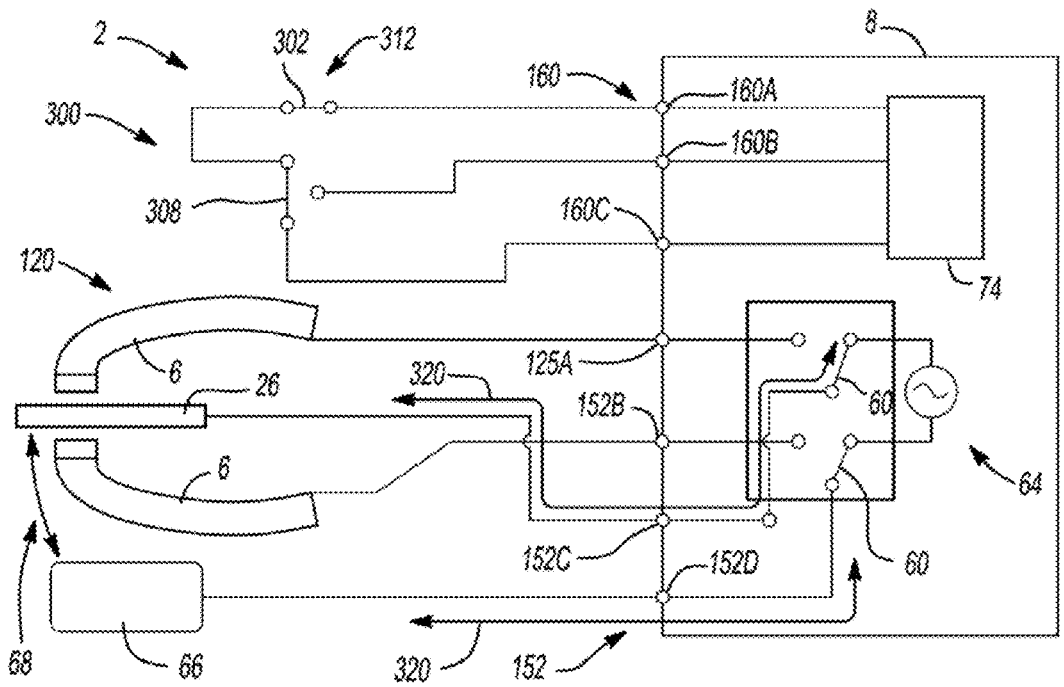
FIG. 28C illustrates the electrosurgical device of FIG. 28A in the monopolar configuration.

FIG. 27D illustrates the blade electrode 26 extended out from the insulator housing 96 and between the working arms 6 and power 68 extending from the blade electrode 26 to the ground pad 66. The activation circuit 300 includes the bipolar activation button 40 in a first switch state 310 and open 62 and the monopolar activation button 42 in a second switch state 312 so that a complete circuit is formed with the middle port 160B and the lower port 160C. A signal is transmitted through the middle port 160B and the lower port 160C to the internal switching and/or CPU 74 that communicates with the voltage source 64 so that voltage is provided through the switches 60 in the direction 320 and through the monopolar active pin 152C to the blade electrode 62 and through the monopolar return pin 152D to the ground pad 66. The power 68 that extends between the blade electrode 26 and the ground pad 66 is a second therapy current that differs from the first therapy current. FIGS. 28A through 28C illustrate an electrosurgical device 2 with an activation circuit 300 connected to a generator by a plurality of ports 180 and a handpiece 120 connected to the generator 8 by a plurality of pins 152. The activation circuit 300 includes an activation buttons 302 that when depressed powers the handpiece 120 and a selector 308 that changes the signal sent from the activation circuit 300 to the generator 8. FIG. 28A illustrates the activation circuit 300 with the activation button 302 in the first switch state 310 and open 62 so that the electrosurgical device 2 is off. The activation circuit 300 has three electrical paths (i.e., wires) that connect with the generator 8 via an upper port 160A, a middle port 160B, and a lower port 160C. The ports 160 connect the activation circuit 300 with internal switching and/or a CPU 74 that when receives a signal communicates with the power source 64 powering the handpiece 120. The power source 64 directs power through a series of switches 60, which as illustrated are in a neutral position 58. The switches 60 direct the power through the plurality of pins 160. The plurality of pins are a bipolar positive pin 152A, a bipolar negative pin 152B, a monopolar active pin 152C, and a monopolar return pin 152D that power one or more parts of the handpiece 120 when the handpiece 120 is switched between a monopolar configuration and a bipolar configuration.

FIG. 28B illustrates the activation button 302 in the second switch state 312 and the selector 308 in a first position so that a signal extends through the upper port 160A and the middle port 160B to the generator 8 and the internal switching and/or CPU 74. The internal switching and/or CPU 74 communicates with the voltage source 64 so that voltage extends in the direction 320. The switches 60 direct the voltage through the bipolar positive pin 152A into a first working arm 6 and through the bipolar negative pin 152B into the second working arm 6. Power 68 extends between the first working arm 6 and the second working arm 6.

FIG. 28B illustrates the activation button 302 in the second switch state 312 and the selector in a second position so that a signal extends through the upper port 160A and a lower port 1630 to the generator 8 and the internal switching and/or CPU 74. The internal switching and/or CPU 74 communicates with the voltage source 64 so that voltage extends in the direction 320. The switches 60 direct the voltage through the monopolar active pin 152C to the blade electrode 26 and the monopolar return pin 152D to the ground pad 66. Power 68 extends between the blade electrode 68 and the ground pad 66.

Figure 29A:
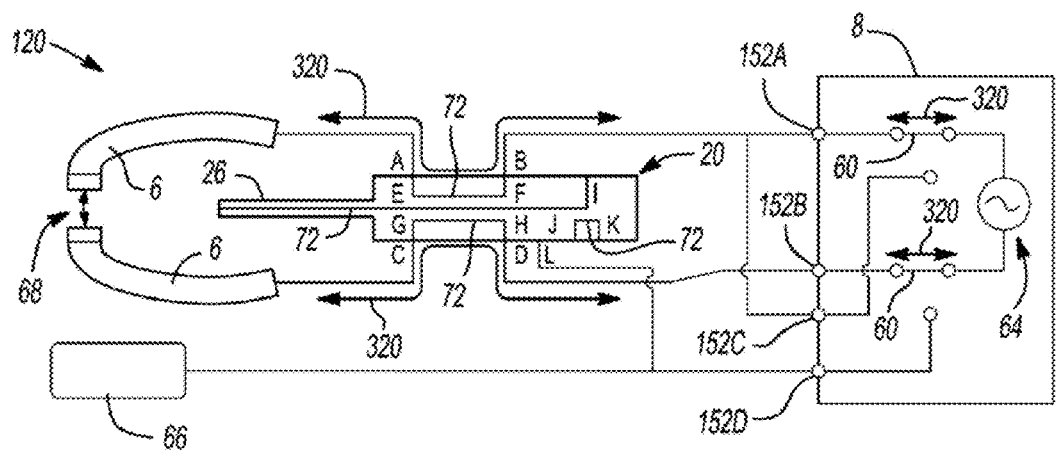
FIG. 29A illustrates an example of a shuttle including reconfigurable conductive paths and the electrosurgical device being in the bipolar configuration.
Figure 29B:
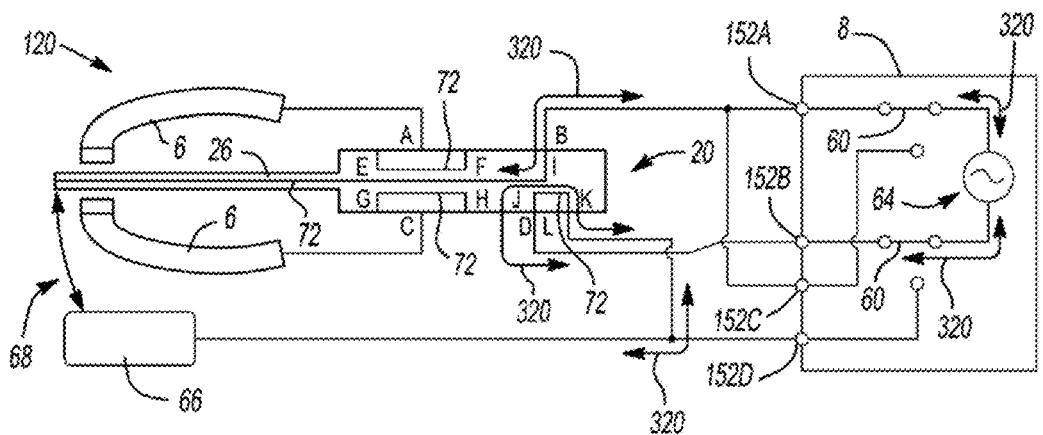
FIG. 29B illustrates an example of the shuttle being moved to a bipolar configuration and the conductive paths being reconfigured.
Figure 29C:
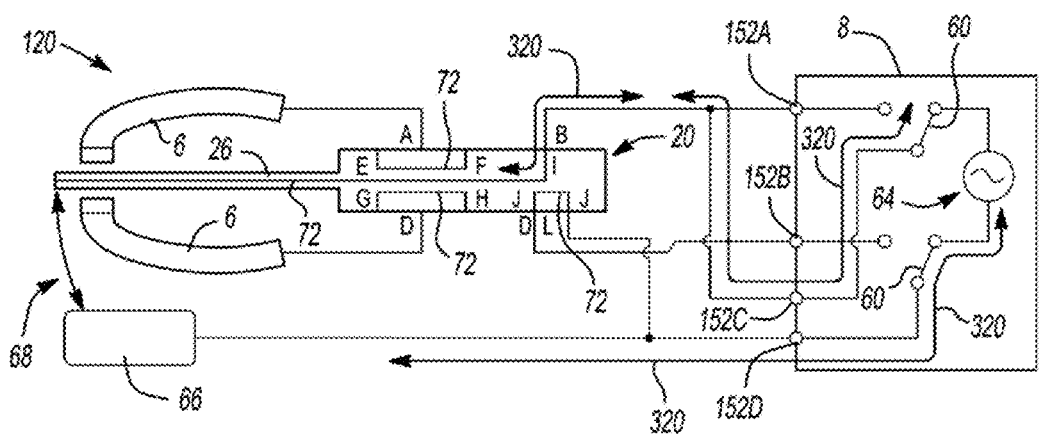
FIG. 29C illustrates and example of the shuttle in the bipolar configuration and conductive paths being reconfigured within a generator.

FIGS. 29A through 29C illustrate a close-up view of the shuttle 20 of the handpiece 120 and associated reconfiguration that occurs by movement of the shuttle 20. The handpiece 120 is connected to a generator 8 that provides voltage from a voltage source 64 that extends in the direction 320 through the switches. The power exits the generator 8 from the bipolar positive pin 152A and the bipolar negative pin 152B into the handpiece 120. The shuttle 20 is retracted so that power extends from the bipolar positive pin 152A into the electrical connectors of the handpiece 120 at points B and F and exits at points E and A so that the first working is powered. Similarly, power that extends through the bipolar negative pin 152B into the electrical connectors 72 at points D and H and exits at points G and C so that the second working arm is powered. Power 68 extends between the working arms 6 so that a therapy current is produced. As illustrated electrical connectors 72 between points E and I and points J and K are open.

FIG. 29B illustrates the blade electrode 26 extended between the working arms 6 so that the ends A and C of the working arms do not align with any electrical connectors 72 and the wires of the blade electrode 26 and the ground pad 66 are aligned as is discussed herein. Power flows in the direction 320 form the voltage source 64 to ground pad 66. The ground pad 66 is connected at points L and K and the connector exits the shuttle at points J and D and into the generator at the bipolar negative pin 152B. Power flows from the voltage source 64 to the blade electrode 26 in the direction 320 along a path through the bipolar positive pin 152A they into the electrical connector 72 at points and until the power travels between the blade electrode 26 and the ground pad 66.

FIG. 29C illustrates another way to power the blade electrode 26 and the ground pad 66. The ground pad 66 and voltage source 64 are connected through the monopolar return pin 152D where power does not pass through the shuttle 20 and passes in the direction 320. The blade electrode 26 is powered through the monopolar active pin 152C where power extends through the shuttle 20 at points B and I and then to the tip of the blade electrode 26 where power 68 flows between the blade electrode 26 and the ground pad 66.

Figure 30A:
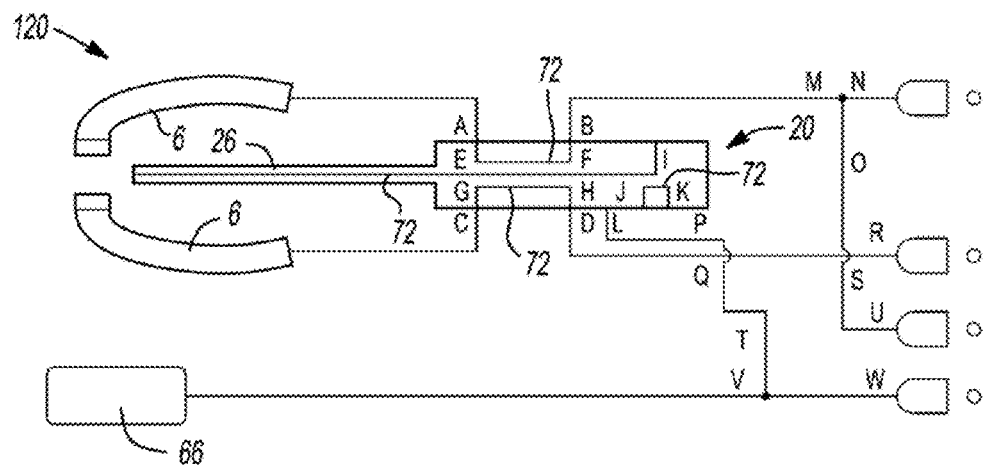
FIG. 30A illustrates an example of a shuttle with reconfigurable conductive paths and one possible plug arrangement.
Figure 30B:
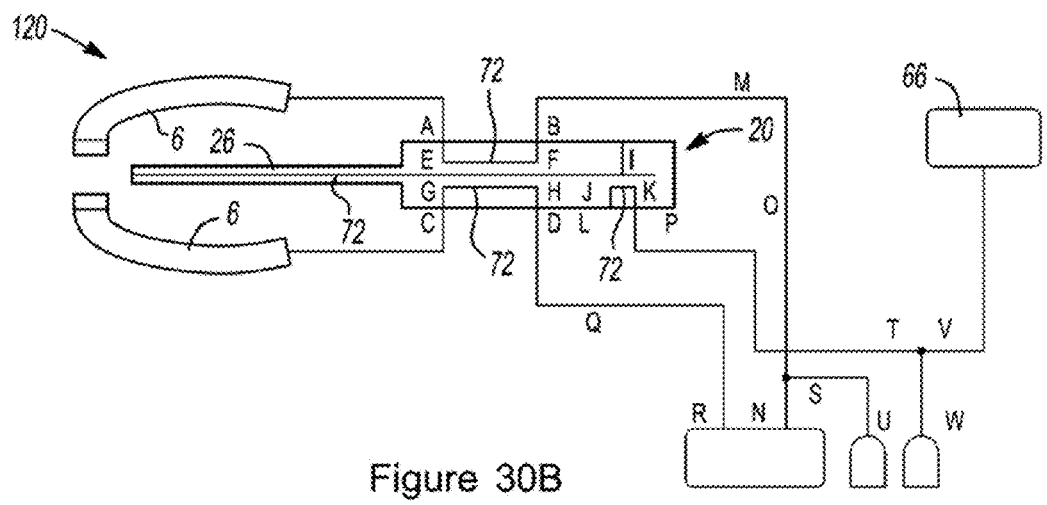
FIG. 30B illustrates another example of a shuttle with reconfigurable conductive paths and another possible plug arrangement.

FIGS. 30A and 30B illustrate two possible wiring schematics that may be used to power the handpiece 120 as is taught herein. FIG. 30A illustrates an example of a four prong connector. The ground pad 66 as illustrated is directly connected to the plug at point W and is indirectly connected to the plug at point R through the shuttle T and electrical connector at points J and K. The first working arm 6 is connected to the plug at point N through the electrical connector at points E and F. The first working arm 6 is indirectly connected to the plug at point U through a connection between points M and N so that power can also pass through points E and F of the electrical connector 74 of the shuttle 20. The second working arm is directly connected to the plug at point R when connects through points G and H.

FIG. 30B illustrates an example of a three prong connector. The ground pad 66 is directly connected to the plug at point W. The plug at point U is directly connected to the first working arm 6 through points E and F. The plug at point U also directly connects to the blade electrode 26 when extended at point I. The plug at point N is connected to the first working arm at points E and F. The plug at point R is connected to the second working arm through points G and H.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative a restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

We claim:

1. An electrosurgical device comprising:
    a. forceps including:
        i. a first working arm and
        ii. a second working arm;
    b. a blade electrode;
    c. an immobilization feature that is slidable along the electrosurgical device;
    wherein the electrosurgical device is capable of being switched between a first electrical configuration so that the electrosurgical device delivers a first therapy current through the first working arm, the second working arm, or both, and a second electrical configuration so that the electrosurgical device delivers a second therapy current through the blade electrode;
    wherein the first working arm and the second working arm of the forceps are immobilized in the second electrical configuration by the immobilization feature being moved from a first position to a second position so that both the forceps and the first therapy current are disabled, and
    wherein the blade electrode extends between and beyond the first working arm and the second working arm in the second electrical configuration;
    wherein the electrosurgical device includes a shuttle that slides along the forceps and the immobilization feature is part of the shuttle and the immobilization feature assists in disabling both the forceps and the first therapy current; and
    wherein the shuttle has a second position where the shuttle covers one or more first activation buttons for applying the first therapy current and a first position where the shuttle covers one or more second activation buttons for applying the second therapy current so that only the one or more first activation buttons or the one or more second activation buttons are exposed at one time.

2. The electrosurgical device of claim 1, wherein the first electrical configuration is deactivated by electrically disconnecting the one or more first activation buttons, electrically disconnecting the blade electrode, shorting the first working arm to the second working arm, or a combination thereof.

3. The electrosurgical device of claim 1, wherein the shuttle is connected to the blade electrode and the shuttle moves the blade electrode between the second electrical configuration and the first electrical configuration.

4. The electrosurgical device of claim 1, wherein the shuttle includes a through hole that surrounds a portion of the electrosurgical device including one or more of the one or more first activation buttons, one or more of the one or more second activation buttons, or both one or more of the one or more first activation buttons and one or more of the one or more second activation buttons.

5. An electrosurgical device comprising:
    a. forceps including:
        i. a first working arm and
        ii. a second working arm;
    b. a blade electrode;
    c. an immobilization feature that is slidable along the electrosurgical device;
    d. one or more first activation buttons; and
    e. one or more second activation buttons;
    wherein the electrosurgical device is capable of being switched between a first electrical configuration so that the electrosurgical device delivers a first therapy current through the first working arm, the second working arm, or both, and a second electrical configuration so that the electrosurgical device delivers a second therapy current through the blade electrode;
    wherein the first working arm and the second working arm of the forceps are immobilized in the second electrical configuration by the immobilization feature being moved from a first position to a second position so that both the forceps and the first therapy current are disabled, and
    wherein the blade electrode extends between and beyond the first working arm and the second working arm in the second electrical configuration;
    wherein the electrosurgical device includes a shuttle that slides along the forceps and the immobilization feature is part of the shuttle and the immobilization feature assists in disabling both the forceps and the first therapy current; and
    wherein the shuttle has a second position where the shuttle impedes movement of one or more of the one or more first activation buttons for applying the first therapy current and a first position where the shuttle impedes movement of one or more of the one or more second activation buttons for applying the second therapy current so that only the one or more first activation buttons or the one or more second activation buttons are impeded from movement at one time.

6. The electrosurgical device of claim 5, wherein the forceps include a bias device that moves the shuttle from the second electrical configuration to the first electrical configuration so that the device can be switched from the second electrical configuration to the first electrical configuration or vice versa using only one hand.

7. The electrosurgical device of claim 5, wherein the first working arm and second working arm are both in direct contact with the blade electrode when the electrosurgical device is in the second electrical configuration so that the first working arm and the second working arm immobilize the blade.

8. An electrosurgical device comprising:
   a. forceps including:
      i) a first working arm having a first contact region and
      ii) a second working arm having a second contact region;
   b. a blade electrode;
   c. an immobilization feature that is slidable along the electrosurgical device: wherein the electrosurgical device is capable of being switched between a first electrical configuration so that the electrosurgical device delivers a first therapy current through the first working arm, the second working arm, or both, and a second electrical configuration so that the electrosurgical device delivers a second therapy current through the blade electrode;
   wherein the first working arm and the second working arm of the forceps are immobilized in the second electrical configuration by the immobilization feature being moved from a first position to a second position so that both the forceps and the first therapy current are disabled, and
   wherein the blade electrode extends between and beyond the first working arm and the second working arm in the second electrical configuration;
   wherein the electrosurgical device includes a shuttle that slides along the forceps and the immobilization feature is part of the shuttle and the immobilization feature assists in disabling both the forceps and the first therapy current; and
   wherein the shuttle is connected to the first working arm and the second working arm and the shuttle moves the first working arm and second working arm between the second electrical configuration and the first electrical configuration.

9. The electrosurgical device of claim 8, wherein the first working arm and second working arm are both in direct contact with the blade electrode when the electrosurgical device is in the second electrical configuration so that the first working arm and the second working arm immobilize the blade electrode.

10. The electrosurgical device of claim 8, wherein the first working arm and the second working arm are free of a channel.

11. The electrosurgical device of claim 8, wherein the first contact region and second contact region are planar.

12. An electrosurgical device comprising:
   a. forceps including:
      i. a first working arm and
      ii. a second working arm;
   b. a blade electrode;
   c. an immobilization feature that is slidable along the electrosurgical device;
   wherein the electrosurgical device is capable of being switched between a first electrical configuration so that the electrosurgical device delivers a first therapy current through the first working arm, the second working arm, or both, and a second electrical configuration so that the electrosurgical device delivers a second therapy current through the blade electrode;
   wherein the first working arm and the second working arm of the forceps are immobilized in the second electrical configuration by the immobilization feature being moved from a first position to a second position so that both the forceps and the first therapy current are disabled,
   wherein the blade electrode extends between and beyond the first working arm and the second working arm in the second electrical configuration; and
   wherein the blade electrode is rotatable so that a length of the blade electrode is rotatable to be parallel to a contact region between the first working arm and the second, and the length of the blade electrode is rotatable to be perpendicular to the contact region between the first working arm and the second working arm.

13. An electrosurgical device comprising:
   a. forceps including:
      i. a first working arm and
      ii. a second working arm;
   b. a blade electrode;
   c. an immobilization feature that is slidable along the electrosurgical device;
   wherein the electrosurgical device is capable of being switched between a first electrical configuration so that the electrosurgical device delivers a first therapy current through the first working arm, the second working arm, or both, and a second electrical configuration so that the electrosurgical device delivers a second therapy current through the blade electrode;
   wherein the first working arm and the second working arm of the forceps are immobilized in the second electrical configuration by the immobilization feature being moved from a first position to a second position so that both the forceps and the first therapy current are disabled,
   wherein the blade electrode extends between and beyond the first working arm and the second working arm in the second electrical configuration; and
   wherein the first working arm, the second working arm, or both is in electrical contact with the blade electrode when the electrosurgical device is in the second electrical configuration.

14. The electrosurgical device of claim 13 wherein the electrosurgical device includes a shuttle that slides along the forceps and the shuttle assists in disabling both the forceps and the first therapy current.

15. An electrosurgical device comprising:
   a. forceps including:
      i. a first working arm and
      ii. a second working arm;
   b. a blade electrode;
   c. an immobilization feature that is slidable along the electrosurgical device;
   wherein the electrosurgical device is capable of being switched between a first electrical configuration so that the electrosurgical device delivers a first therapy current through the first working arm, the second working arm, or both, and a second electrical configuration so that the electrosurgical device delivers a second therapy current through the blade electrode;
   wherein the first working arm and the second working arm of the forceps are immobilized in the second electrical configuration by the immobilization feature being moved from a first position to a second position so that both the forceps and the first therapy current are disabled,
   wherein the blade electrode extends between and beyond the first working arm and the second working arm in the second electrical configuration;

wherein the electrosurgical device includes a shuttle that slides along the forceps and the immobilization feature is part of the shuttle and the immobilization feature assists in disabling both the forceps and the first therapy current; and wherein the first working arm has an immobilization arm and the second working arm has an immobilization arm and the shuttle has the immobilization feature that engages both the immobilization arm of the first working arm and the second working arm so that the first working arm and the second working arm are biased towards each other as the shuttle is moved from the first position to the second position.

* * * * *